United States Patent
Cragg

(10) Patent No.: US 8,317,867 B2
(45) Date of Patent: Nov. 27, 2012

(54) METHODS AND APPARATUS FOR PERFORMING THERAPEUTIC PROCEDURES IN THE SPINE

(75) Inventor: Andrew H. Cragg, Edina, MN (US)

(73) Assignee: TranS1 Inc., Wilmington, NC (US)

( * ) Notice: Subject to any disclaimer, the term of this patent is extended or adjusted under 35 U.S.C. 154(b) by 0 days.

(21) Appl. No.: 13/342,868

(22) Filed: Jan. 3, 2012

(65) Prior Publication Data
US 2012/0123543 A1 May 17, 2012

Related U.S. Application Data

(63) Continuation of application No. 12/856,372, filed on Aug. 13, 2010, now Pat. No. 8,105,365, which is a continuation of application No. 11/956,236, filed on Dec. 13, 2007, now Pat. No. 7,794,463, which is a continuation of application No. 10/430,841, filed on May 6, 2003, now Pat. No. 7,309,338, which is a continuation of application No. 09/782,583, filed on Feb. 13, 2001, now Pat. No. 6,558,390.

(60) Provisional application No. 60/182,748, filed on Feb. 16, 2000.

(51) Int. Cl.
*A61F 2/44* (2006.01)

(52) U.S. Cl. ................................... 623/17.11

(58) Field of Classification Search ........ 606/270, 606/250, 254, 257, 259, 261, 279, 92, 278, 606/86 A, 247; 623/17.11–17.16
See application file for complete search history.

(56) References Cited

U.S. PATENT DOCUMENTS

| | | | |
|---|---|---|---|
| 1,630,239 A | 5/1924 | Binkley et al. | |
| 2,336,338 A | 12/1943 | Zublin | |
| 3,103,926 A | 9/1963 | Cochran et al. | |
| 3,367,326 A * | 2/1968 | Frazier | 606/86 A |

(Continued)

FOREIGN PATENT DOCUMENTS

EP 0 611 116 B1 4/1994

(Continued)

OTHER PUBLICATIONS

Jeanneret, et al., "Posterior Stabilization in L5-S1 Isthmic Spondylolisthesis with Paralaminar Screw Fixation: Anatomical and Clinical Results," Journal of Spinal Disorders, vol. 9, No. 3, pp. 223-233 (1996) Lippincott-Raven Publishers, Philadelphia.

(Continued)

*Primary Examiner* — Pedro Philogene
(74) *Attorney, Agent, or Firm* — Knobbe, Martens, Olson & Bear, LLP

(57) ABSTRACT

Methods for correcting a deformity in the spine by forming a trans-sacral axial instrumentation/fusion axial bore through vertebral bodies in general alignment with a visualized, anterior axial instrumentation/fusion line in a minimally invasive, low trauma, manner and providing a therapy to the spine employing the axial bore. Curved or relatively straight anterior axial bores are formed from the anterior starting positions. The therapies performed through the axial bores include discoscopy, full and partial discectomy, vertebroplasty, balloon-assisted vertebroplasty, drug delivery, electrical stimulation and various forms of spinal disc cavity augmentation, spinal disc replacement, fusion of spinal motion segments and implantation of radioactive seeds. Axial spinal implants and bone growth materials can be placed into single or multiple parallel or diverging axial bores to fuse two or more vertebrae, or distract or shock absorb two or more vertebrae.

12 Claims, 36 Drawing Sheets

U.S. PATENT DOCUMENTS

| | | |
|---|---|---|
| 3,554,192 A | 1/1971 | Isberner |
| 3,892,232 A | 7/1975 | Neufeld |
| 4,135,506 A | 1/1979 | Ulrich |
| 4,170,990 A | 10/1979 | Baumgart et al. |
| 4,175,555 A | 11/1979 | Herbert |
| 4,265,231 A | 5/1981 | Scheller, Jr. et al. |
| 4,309,777 A | 1/1982 | Patil |
| 4,401,112 A | 8/1983 | Rezaian |
| 4,453,539 A | 6/1984 | Raftopoulos et al. |
| 4,541,423 A | 9/1985 | Barber |
| 4,545,374 A | 10/1985 | Jacobson |
| 4,553,273 A | 11/1985 | Wu |
| 4,554,914 A | 11/1985 | Kapp et al. |
| 4,573,448 A | 3/1986 | Kambin |
| 4,636,217 A | 1/1987 | Ogilvie et al. |
| 4,640,271 A | 2/1987 | Lower |
| 4,650,466 A | 3/1987 | Luther |
| 4,657,550 A | 4/1987 | Daher |
| 4,756,649 A | 7/1988 | Heule |
| 4,773,402 A | 9/1988 | Asher et al. |
| 4,815,453 A | 3/1989 | Cotrel |
| 4,844,088 A | 7/1989 | Kambin |
| 4,858,601 A | 8/1989 | Glisson |
| 4,862,891 A | 9/1989 | Smith |
| RE33,258 E | 7/1990 | Onik et al. |
| RE33,348 E | 9/1990 | Lower |
| 4,966,604 A | 10/1990 | Reiss |
| 4,969,888 A | 11/1990 | Scholten et al. |
| 5,002,546 A | 3/1991 | Romano |
| 5,015,255 A | 5/1991 | Kuslich |
| 5,019,079 A | 5/1991 | Ross |
| 5,030,201 A | 7/1991 | Palestrant |
| 5,059,193 A | 10/1991 | Kuslich |
| 5,062,850 A | 11/1991 | Macmillan et al. |
| 5,071,437 A | 12/1991 | Steffee |
| 5,147,404 A | 9/1992 | Downey |
| 5,171,279 A | 12/1992 | Mathews |
| 5,190,546 A | 3/1993 | Jervis |
| 5,192,326 A | 3/1993 | Bao et al. |
| 5,195,968 A | 3/1993 | Lundquist et al. |
| 5,231,910 A | 8/1993 | Harsch et al. |
| 5,236,460 A | 8/1993 | Barber |
| 5,242,443 A | 9/1993 | Kambin |
| 5,242,444 A | 9/1993 | MacMillan |
| 5,242,461 A | 9/1993 | Kortenbach et al. |
| 5,246,458 A | 9/1993 | Graham |
| 5,258,031 A | 11/1993 | Salib et al. |
| 5,269,785 A | 12/1993 | Bonutti |
| 5,285,795 A | 2/1994 | Ryan et al. |
| 5,290,289 A | 3/1994 | Sanders et al. |
| 5,313,962 A | 5/1994 | Obenchain |
| 5,336,223 A | 8/1994 | Rogers |
| 5,357,983 A | 10/1994 | Mathews |
| 5,360,448 A | 11/1994 | Thramann |
| 5,366,457 A | 11/1994 | McGuire et al. |
| 5,383,884 A | 1/1995 | Summers |
| 5,395,188 A | 3/1995 | Bailey et al. |
| 5,395,317 A | 3/1995 | Kambin |
| 5,396,880 A | 3/1995 | Kagan et al. |
| 5,403,276 A | 4/1995 | Schechter et al. |
| 5,415,661 A | 5/1995 | Holmes |
| 5,433,739 A | 7/1995 | Sluijter et al. |
| 5,445,140 A | 8/1995 | Tovey |
| 5,480,440 A | 1/1996 | Kambin |
| 5,484,437 A | 1/1996 | Michelson |
| 5,489,308 A | 2/1996 | Kuslich et al. |
| 5,496,322 A | 3/1996 | Mathews |
| 5,505,732 A | 4/1996 | Michelson |
| 5,514,137 A | 5/1996 | Coutts |
| 5,514,180 A | 5/1996 | Heggeness et al. |
| 5,520,688 A | 5/1996 | Lin |
| 5,534,031 A | 7/1996 | Matsuzaki et al. |
| 5,545,228 A | 8/1996 | Kambin |
| 5,549,679 A | 8/1996 | Kuslich |
| 5,554,163 A | 9/1996 | Shturman |
| 5,558,674 A | 9/1996 | Heggeness et al. |
| 5,562,736 A | 10/1996 | Ray et al. |
| 5,569,248 A | 10/1996 | Mathews |
| 5,571,189 A | 11/1996 | Kuslich |
| 5,571,190 A | 11/1996 | Ulrich et al. |
| 5,571,192 A | 11/1996 | Schonhoffer |
| 5,584,887 A | 12/1996 | Kambin |
| 5,591,170 A | 1/1997 | Spievack et al. |
| 5,591,235 A | 1/1997 | Kuslich |
| 5,593,407 A | 1/1997 | Reis |
| 5,630,816 A | 5/1997 | Kambin |
| 5,653,708 A | 8/1997 | Howland |
| 5,658,286 A | 8/1997 | Sava |
| 5,665,122 A | 9/1997 | Kambin |
| 5,669,909 A | 9/1997 | Zdeblick et al. |
| 5,700,291 A | 12/1997 | Kuslich et al. |
| 5,702,453 A | 12/1997 | Rabbe et al. |
| 5,702,454 A | 12/1997 | Baumgartner |
| 5,702,455 A | 12/1997 | Saggar |
| 5,713,904 A | 2/1998 | Errico et al. |
| 5,728,097 A | 3/1998 | Mathews |
| 5,733,284 A | 3/1998 | Martin |
| 5,735,899 A | 4/1998 | Schwartz et al. |
| 5,741,253 A | 4/1998 | Michelson |
| 5,741,261 A | 4/1998 | Moskovitz et al. |
| 5,743,912 A | 4/1998 | Lahille et al. |
| 5,762,629 A | 6/1998 | Kambin |
| 5,779,704 A | 7/1998 | Kim |
| 5,785,709 A | 7/1998 | Kummer et al. |
| 5,792,044 A | 8/1998 | Foley et al. |
| 5,792,110 A | 8/1998 | Cunningham |
| 5,807,318 A | 9/1998 | St. Goar et al. |
| 5,810,815 A | 9/1998 | Morales |
| 5,827,285 A | 10/1998 | Bramlet |
| 5,827,328 A | 10/1998 | Buttermann |
| 5,885,292 A | 3/1999 | Moskovitz et al. |
| 5,888,220 A | 3/1999 | Felt et al. |
| 5,888,223 A | 3/1999 | Bray, Jr. |
| 5,891,147 A | 4/1999 | Moskovitz et al. |
| 5,902,231 A | 5/1999 | Foley et al. |
| 5,906,616 A | 5/1999 | Pavlov et al. |
| 5,916,267 A | 6/1999 | Tienboon |
| 5,921,971 A | 7/1999 | Agro et al. |
| 5,928,239 A | 7/1999 | Mirza |
| 5,935,131 A | 8/1999 | Bonutti |
| 5,937,524 A | 8/1999 | Hornsby |
| 5,951,553 A | 9/1999 | Betz et al. |
| 5,954,635 A | 9/1999 | Foley et al. |
| 5,961,329 A | 10/1999 | Stucki-McCormick |
| 5,964,761 A | 10/1999 | Kambin |
| 5,968,062 A | 10/1999 | Thomas et al. |
| 5,972,015 A | 10/1999 | Scribner et al. |
| 5,976,146 A | 11/1999 | Ogawa et al. |
| 5,976,187 A | 11/1999 | Richelsoph |
| 5,980,504 A | 11/1999 | Sharkey et al. |
| 5,989,256 A | 11/1999 | Kuslich et al. |
| 5,989,290 A | 11/1999 | Biedermann et al. |
| 6,001,101 A | 12/1999 | Augagneur et al. |
| 6,007,487 A | 12/1999 | Foley et al. |
| 6,010,495 A | 1/2000 | Tilton, Jr. |
| 6,010,502 A | 1/2000 | Bagby |
| 6,019,792 A | 2/2000 | Cauthen |
| 6,022,362 A | 2/2000 | Lee et al. |
| 6,030,162 A | 2/2000 | Huebner |
| 6,033,406 A | 3/2000 | Mathews |
| 6,033,407 A | 3/2000 | Behrens |
| 6,036,696 A | 3/2000 | Lambrecht et al. |
| 6,053,916 A | 4/2000 | Moore |
| 6,056,749 A * | 5/2000 | Kuslich ............... 606/86 A |
| 6,063,088 A | 5/2000 | Winslow |
| 6,066,152 A | 5/2000 | Strauss et al. |
| 6,066,154 A | 5/2000 | Reiley et al. |
| 6,080,099 A | 6/2000 | Slater et al. |
| 6,086,589 A * | 7/2000 | Kuslich et al. ............... 606/247 |
| 6,093,205 A | 7/2000 | McLeod |
| 6,093,207 A | 7/2000 | Pisharodi |
| 6,095,149 A | 8/2000 | Sharkey et al. |
| RE36,857 E | 9/2000 | Euteneuer et al. |
| 6,120,502 A | 9/2000 | Michelson |
| 6,123,705 A | 9/2000 | Michelson |
| 6,127,597 A | 10/2000 | Beyar et al. |
| 6,152,871 A | 11/2000 | Foley et al. |

| Patent | Date | Inventor |
|---|---|---|
| 6,159,212 A | 12/2000 | Schoedinger, III et al. |
| 6,162,170 A | 12/2000 | Foley et al. |
| 6,175,758 B1 | 1/2001 | Kambin |
| 6,176,823 B1 | 1/2001 | Foley et al. |
| 6,187,000 B1 | 2/2001 | Davison et al. |
| 6,206,822 B1 | 3/2001 | Foley et al. |
| 6,206,826 B1 | 3/2001 | Mathews et al. |
| 6,210,412 B1 | 4/2001 | Michelson |
| 6,217,509 B1 | 4/2001 | Foley et al. |
| 6,241,735 B1 | 6/2001 | Marmulla |
| 6,264,656 B1 | 7/2001 | Michelson |
| 6,287,313 B1 | 9/2001 | Sasso |
| 6,306,140 B1 | 10/2001 | Siddiqui |
| 6,315,795 B1 | 11/2001 | Scarborough et al. |
| 6,319,254 B1 | 11/2001 | Giet et al. |
| RE37,479 E * | 12/2001 | Kuslich .................... 623/17.11 |
| 6,348,055 B1 | 2/2002 | Preissman |
| 6,371,968 B1 | 4/2002 | Kogasaka et al. |
| 6,371,990 B1 | 4/2002 | Ferree |
| 6,379,334 B1 | 4/2002 | Frassica |
| 6,383,188 B2 | 5/2002 | Kuslich et al. |
| 6,383,190 B1 | 5/2002 | Preissman |
| 6,387,130 B1 | 5/2002 | Stone et al. |
| 6,395,007 B1 | 5/2002 | Bhatnagar et al. |
| 6,395,034 B1 | 5/2002 | Suddaby |
| 6,402,750 B1 | 6/2002 | Atkinson et al. |
| 6,409,766 B1 | 6/2002 | Brett |
| 6,416,515 B1 | 7/2002 | Wagner |
| 6,419,677 B2 | 7/2002 | Zucherman et al. |
| 6,419,678 B1 | 7/2002 | Asfora |
| 6,423,095 B1 | 7/2002 | Van Hoeck et al. |
| 6,436,098 B1 | 8/2002 | Michelson |
| 6,436,102 B1 | 8/2002 | Ralph et al. |
| 6,436,140 B1 | 8/2002 | Liu et al. |
| 6,436,143 B1 | 8/2002 | Ross et al. |
| 6,440,138 B1 | 8/2002 | Reiley et al. |
| 6,447,514 B1 | 9/2002 | Stalcup et al. |
| 6,447,518 B1 | 9/2002 | Krause et al. |
| 6,447,546 B1 | 9/2002 | Bramlet et al. |
| 6,447,547 B1 | 9/2002 | Michelson |
| 6,464,713 B2 | 10/2002 | Bonutti |
| 6,468,279 B1 | 10/2002 | Reo |
| 6,485,518 B1 | 11/2002 | Cornwall et al. |
| 6,500,173 B2 | 12/2002 | Underwood et al. |
| 6,517,541 B1 | 2/2003 | Sesic |
| 6,533,791 B1 | 3/2003 | Betz et al. |
| 6,540,747 B1 | 4/2003 | Marino |
| 6,558,386 B1 | 5/2003 | Cragg |
| 6,558,390 B2 | 5/2003 | Cragg |
| 6,562,046 B2 | 5/2003 | Sasso |
| 6,575,979 B1 | 6/2003 | Cragg |
| 6,607,530 B1 | 8/2003 | Carl et al. |
| 6,610,091 B1 | 8/2003 | Reiley |
| 6,652,535 B2 | 11/2003 | Kvarnstrom et al. |
| 6,692,495 B1 | 2/2004 | Zacouto |
| 6,740,090 B1 | 5/2004 | Cragg et al. |
| 6,746,451 B2 | 6/2004 | Middleton et al. |
| 6,764,489 B2 | 7/2004 | Ferree |
| 6,790,210 B1 | 9/2004 | Cragg et al. |
| 6,805,697 B1 * | 10/2004 | Helm et al. .................... 606/92 |
| 6,875,215 B2 | 4/2005 | Taras et al. |
| 6,899,716 B2 | 5/2005 | Cragg |
| 6,921,403 B2 | 7/2005 | Cragg et al. |
| 6,991,653 B2 | 1/2006 | White et al. |
| 7,014,633 B2 * | 3/2006 | Cragg .................... 604/500 |
| 7,033,394 B2 | 4/2006 | Michelson |
| 7,037,309 B2 | 5/2006 | Weil et al. |
| 7,087,056 B2 | 8/2006 | Vaughan |
| 7,087,058 B2 | 8/2006 | Cragg |
| 7,175,626 B2 | 2/2007 | Neff |
| 7,309,338 B2 | 12/2007 | Cragg |
| 7,329,259 B2 | 2/2008 | Cragg |
| 7,473,256 B2 | 1/2009 | Assell et al. |
| 7,491,236 B2 | 2/2009 | Cragg et al. |
| 7,500,977 B2 | 3/2009 | Assell et al. |
| 7,530,993 B2 | 5/2009 | Assell et al. |
| 7,547,317 B2 | 6/2009 | Cragg |
| 7,547,324 B2 | 6/2009 | Cragg et al. |
| 7,569,056 B2 | 8/2009 | Cragg et al. |
| 7,588,574 B2 | 9/2009 | Assell et al. |
| 7,601,171 B2 | 10/2009 | Ainsworth et al. |
| 7,608,077 B2 | 10/2009 | Cragg |
| 7,632,274 B2 | 12/2009 | Assell |
| 7,641,657 B2 | 1/2010 | Cragg |
| 7,662,173 B2 | 2/2010 | Cragg et al. |
| 7,727,263 B2 | 6/2010 | Cragg |
| 7,740,633 B2 | 6/2010 | Assell et al. |
| 7,744,599 B2 | 6/2010 | Cragg |
| 7,763,025 B2 | 7/2010 | Assell et al. |
| 7,794,463 B2 | 9/2010 | Cragg |
| 7,799,032 B2 | 9/2010 | Assell et al. |
| 7,799,033 B2 | 9/2010 | Assell et al. |
| 7,914,535 B2 | 3/2011 | Assell et al. |
| 8,034,055 B2 | 10/2011 | Cragg |
| 8,052,613 B2 | 11/2011 | Assell et al. |
| 8,105,365 B2 | 1/2012 | Cragg |
| 2002/0022888 A1 | 2/2002 | Serhan et al. |
| 2002/0032444 A1 | 3/2002 | Mische |
| 2002/0038123 A1 | 3/2002 | Visotsky et al. |
| 2002/0052608 A1 | 5/2002 | Kvarnstrom et al. |
| 2002/0068939 A1 | 6/2002 | Levy et al. |
| 2002/0072801 A1 | 6/2002 | Michelson |
| 2002/0077632 A1 | 6/2002 | Tsou |
| 2002/0077700 A1 | 6/2002 | Varga et al. |
| 2002/0077702 A1 | 6/2002 | Castro |
| 2002/0082598 A1 | 6/2002 | Teitelbaum |
| 2002/0087163 A1 | 7/2002 | Dixon et al. |
| 2002/0107573 A1 | 8/2002 | Steinberg |
| 2002/0110439 A1 | 8/2002 | Craven |
| 2002/0147485 A1 | 10/2002 | Mamo et al. |
| 2002/0188292 A1 | 12/2002 | Sharkey et al. |
| 2002/0188299 A1 | 12/2002 | Reiley et al. |
| 2003/0028193 A1 | 2/2003 | Weil et al. |
| 2003/0045881 A1 | 3/2003 | Barouk et al. |
| 2003/0065394 A1 | 4/2003 | Michelson |
| 2003/0176926 A1 | 9/2003 | Boehm et al. |
| 2003/0181982 A1 | 9/2003 | Kuslich |
| 2003/0191474 A1 | 10/2003 | Cragg et al. |
| 2003/0204189 A1 | 10/2003 | Cragg |
| 2004/0138752 A1 | 7/2004 | Michelson |
| 2004/0141827 A1 | 7/2004 | Dicke |
| 2004/0151559 A1 | 8/2004 | Craven |
| 2004/0193155 A1 | 9/2004 | Castaneda |
| 2004/0230195 A1 | 11/2004 | Kaikkonen et al. |
| 2005/0038438 A1 | 2/2005 | Anderson et al. |
| 2005/0101961 A1 | 5/2005 | Huebner et al. |
| 2005/0107791 A1 | 5/2005 | Manderson |
| 2005/0113919 A1 | 5/2005 | Cragg et al. |
| 2005/0137604 A1 | 6/2005 | Assell et al. |
| 2005/0137607 A1 | 6/2005 | Assell et al. |
| 2005/0149049 A1 | 7/2005 | Assell et al. |
| 2005/0149191 A1 | 7/2005 | Cragg et al. |
| 2005/0261695 A1 | 11/2005 | Cragg et al. |
| 2006/0058800 A1 | 3/2006 | Ainsworth et al. |
| 2006/0155297 A1 | 7/2006 | Ainsworth et al. |
| 2006/0206208 A1 | 9/2006 | Michelson |
| 2006/0206209 A1 | 9/2006 | Cragg et al. |
| 2006/0229622 A1 | 10/2006 | Huebner et al. |
| 2006/0264957 A1 | 11/2006 | Cragg et al. |
| 2007/0010819 A1 | 1/2007 | Johnstone |
| 2007/0066977 A1 | 3/2007 | Assell et al. |
| 2007/0112351 A1 | 5/2007 | Assell et al. |
| 2007/0118132 A1 | 5/2007 | Culbert et al. |
| 2007/0167951 A1 | 7/2007 | Ainsworth et al. |
| 2007/0168036 A1 | 7/2007 | Ainsworth et al. |
| 2007/0260270 A1 | 11/2007 | Assell et al. |
| 2008/0004707 A1 | 1/2008 | Cragg |
| 2008/0033466 A1 | 2/2008 | Assell et al. |
| 2008/0065076 A1 | 3/2008 | Cragg |
| 2008/0065080 A1 | 3/2008 | Assell et al. |
| 2008/0065092 A1 | 3/2008 | Assell et al. |
| 2008/0071278 A1 | 3/2008 | Assell et al. |
| 2008/0097452 A1 | 4/2008 | Assell et al. |
| 2008/0154275 A1 | 6/2008 | Assell et al. |
| 2008/0188895 A1 | 8/2008 | Cragg |
| 2008/0195156 A1 | 8/2008 | Ainsworth et al. |
| 2008/0262502 A1 | 10/2008 | Ainsworth et al. |
| 2008/0262555 A1 | 10/2008 | Assell |

| | | | |
|---|---|---|---|
| 2009/0105768 A1 | 4/2009 | Cragg et al. | |
| 2009/0240293 A1 | 9/2009 | Cragg | |
| 2009/0270902 A1 | 10/2009 | Assell et al. | |
| 2009/0292287 A1 | 11/2009 | Cragg et al. | |
| 2010/0137991 A1 | 6/2010 | Ainsworth | |
| 2010/0145462 A1 | 6/2010 | Ainsworth | |
| 2011/0029019 A1 | 2/2011 | Ainsworth et al. | |
| 2011/0035005 A1 | 2/2011 | Ainsworth et al. | |
| 2011/0040329 A1 | 2/2011 | Ainsworth | |
| 2011/0082424 A1 | 4/2011 | Barnhouse | |
| 2011/0184420 A1 | 7/2011 | Barnhouse | |

FOREIGN PATENT DOCUMENTS

| | | | |
|---|---|---|---|
| EP | 0 980 677 A1 | 2/2000 | |
| EP | 1 029 519 | 8/2000 | |
| JP | 11-502437 | 3/1999 | |
| WO | WO 95/22285 | 8/1995 | |
| WO | WO 96/11639 A | 4/1996 | |
| WO | WO 96/28118 | 9/1996 | |
| WO | WO 97/40878 | 11/1997 | |
| WO | WO 98/38918 | 9/1998 | |
| WO | WO 98/49945 A | 11/1998 | |
| WO | WO 99/47055 | 9/1999 | |
| WO | WO 99/51149 | 10/1999 | |
| WO | WO 00/67650 | 11/2000 | |
| WO | WO 01/28468 A1 | 4/2001 | |
| WO | WO 01/60268 A1 | 8/2001 | |
| WO | WO 02/09801 A1 | 2/2002 | |
| WO | WO 02/13732 A2 | 2/2002 | |
| WO | WO 02/34120 A2 | 5/2002 | |
| WO | WO 02/058599 A2 | 8/2002 | |
| WO | WO 02/071921 A2 | 9/2002 | |

OTHER PUBLICATIONS

Curtis A. Dickman, M.D., et al., "Transpedicular screw-rod fixation of the lumbar spine: operative technique and outcome in 104 cases," J. Neurosurg, Dec. 1992, vol. 77, pp. 860-870.

Friedrich W. Rathke and Karl F. Schlegel, Surgery of the Spine, Atlas of Orthopaedic Operations, vol. 1, 1979, pp. 222-224.

Hallett H. Mathews, M.D., "Minimally Invasive Fusion Techniques, Percutaneous Interbody Fusions," Orthopedic Clinics of North America, Oct. 1998, vol. 29, No. 4.

Hallett H. Mathews, M.D., et al., "Perspectives on Modern Orthopaedics, Minimally Invasive Techniques for the Treatment of Intervertebral Disk Herniation," Journal of the American Academy of Orthopaedic Surgeons, Mar./Apr. 2002, vol. 10, No. 2.

J. Dove, FRCS, "The Hartshill System for the Front of the Lumbosacral Spine," Lumbosacral and Spinopelvic Fusion, Chapter 42 (pp. 539-543) Lippincott-Raven Publishers (1996).

J.J. Trambert, M.D., "Percutaneous Interventions in the Presacral Space: CT-guided Precoccygeal Approach—Early Experience," (Radiology 1999; 213:901-904).

J. W. Olgilvie, M.D., et al., "Overview of Fixation to the Sacrum & Pelvis in Spinal Surgery," Lumbosacral and Spinopelvic Fusion, Chapter 17 (pp. 191-198) Lippincott-Raven Publishers (1996).

Jason A. Smith, MD, et al., "Clinical Outcome of Trans-Sacral Interbody Fusion After Partial Reduction for High-Grade L5-S1 Spondylolisthesis," Spine, 2001, vol. 26, No. 20, pp. 2227-2234.

John L. Emmett, M.D., M.S. (Urology), David M. Witten, M.D., M.S. (Radiology)—Vol. 1, Third Edition—Clinical Urogrpahy—An Atlas and Textbook of Roentgenologic Diagnosis—1971— Phneumography (Retroperitoneal Gas [Air]Insufflation; Perirenal Insufflation; Presacral Insufflation).

M. R. Zindrick, M.D., et al., "Clinical Anatomy of the Lumbosacral Junction and Pelvix," Lumbosacral and Spinopelvic Fusion, Chapter 2 (pp. 13-25) Lippincott-Raven Publishers (1996).

Michael MacMillan, et al., Biomechanical Analysis of a New Anterior Spine Implant for Post-Corpectomy Instability, Journal of Spinal Disorders, 1995, vol. 8, No. 1, pp. 56-61.

Michael MacMillan, MD, et al., "Percutaneous Lumbosacral Fixation and Fusion," Percutaneous Spine Techniques, Jan. 1996, vol. 7, No. 1, pp. 99-106.

P. Kambin, M.D., et al., "Arthroscopic fusion of the Lumbosacral Spine," Lumbosacral and Spinopelvic Fusion, Chapter 44 (pp. 565-577) Lippincott-Raven Publishers (1996).

Parviz Kambin, M.D., "Percutaneous Spine Techniques, Diagnostic and Therapeutic Spinal Arthroscopy," Neurosurgery Clinics of North America, Jan. 1996, vol. 7, No. 1.

Parviz Kambin, M.D., et al., "Arthroscopic Discectomy of the Lumbar Spine," Clinical Orthopaedics and Related Research, Apr. 1997, No. 337.

Parviz Kambin, M.D., et al., "Arthroscopic Microdiscectomy: an Alternative to Open Disc Surgery," The Mount Sinai Journal of Medicine, Sep. 2000, vol. 67, No. 4.

R. Johnsson, et al., "Posterolateral Lumbar Fusion Using Facet Joint Fixation With Biodegradable Rods: A Pilot Study," Eur Spine J., (1997) 6:144-148.

R.P. Louis, M.D., "Anatomy, Physiology, and Biomechanics of the Lumbopelvic Junction," Lumbosacral and Spinopelvic Fusion, Chapter 1 (pp. 1-11) Lippincott-Raven Publishers (1996).

R.P. Louis, M.D., "Lumbopelvic Fusion," Lumbosacral and Spinopelvic Fusion, Chapter 38, (pp. 479-492) Lippincott-Raven Publishers (1996).

Richard M. Slone, MD, et al., "Spinal Fixation, Part 1, Basic Hardware, and Fixation Techniques for the Cervical Spine," RadioGraphics, 1993, vol. 13, No. 2, pp. 341-356.

Richard M. Slone, MD, et al., "Spinal Fixation, Part 2, Fixation Techniques and Hardware for the Thoracic and Lumbosacral Spine," RadioGraphics, 1993, vol. 13, No. 3, pp. 521-543.

S.A. Caruso, M.E., et al., "Instrumented Fusions of the Lumbosacral Spine: A Technical Overview," Lumbosacral and Spinopelvic Fusion, Chapter 18 (pp. 199-210) Lippincott-Raven Publishers (1996).

Schreiber, A. and Leu, Hj., "Percutaneous Nucleotomy: Technique with Discoscopy," Orthopedics, Apr. 1991, vol. 14, No. 4, pp. 439-446.

Schreiber, Adam et al. "Does Percutaneous Nucleotomy With Discoscopy Replace Conventional Discectomy?," Clinical Orthopaedics and Related Research, No. 238, Jan. 1989, pp. 35-42.

Translation of Japanese Office Action mailed Jul. 14, 2010 in Japanese Patent App. No. 2001-559335.

* cited by examiner

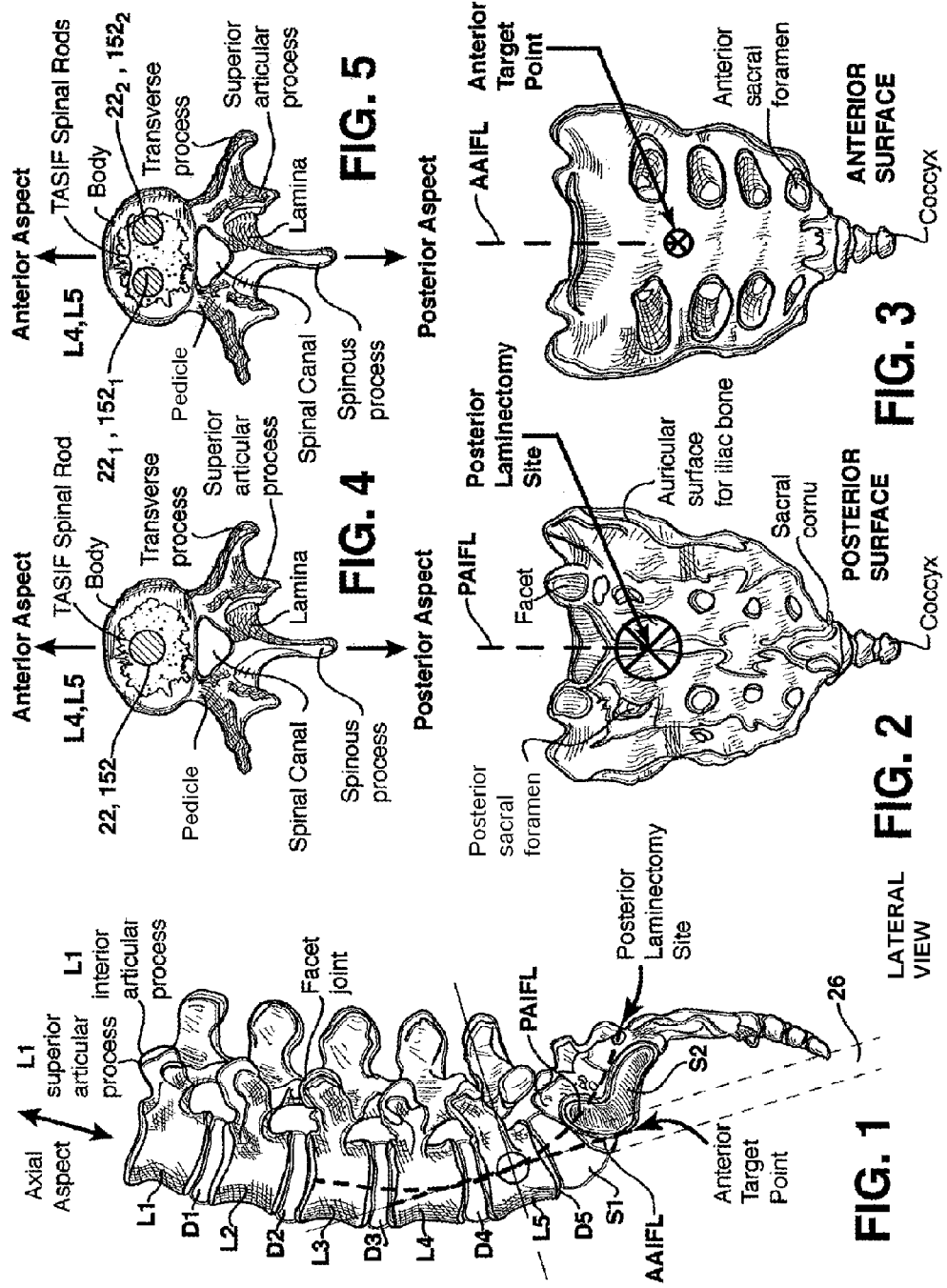

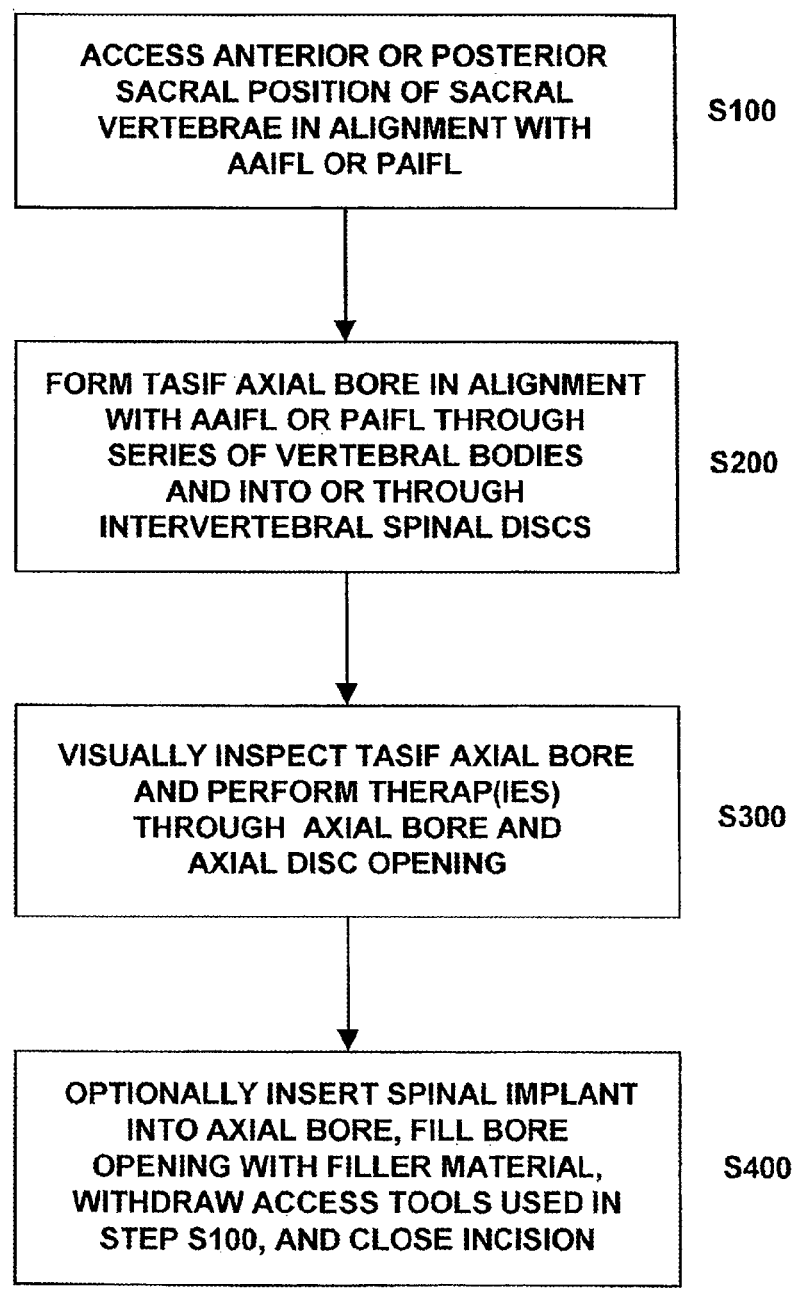

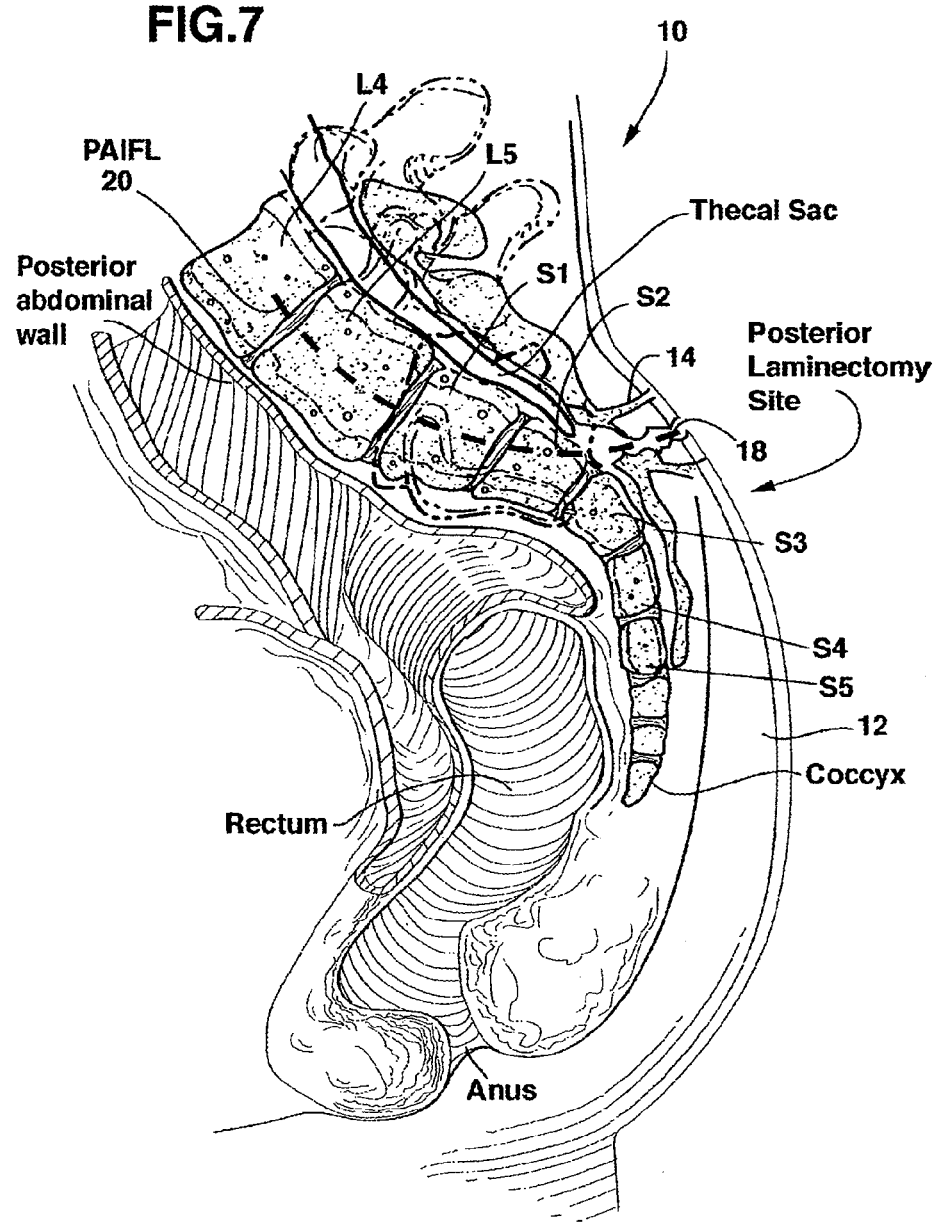

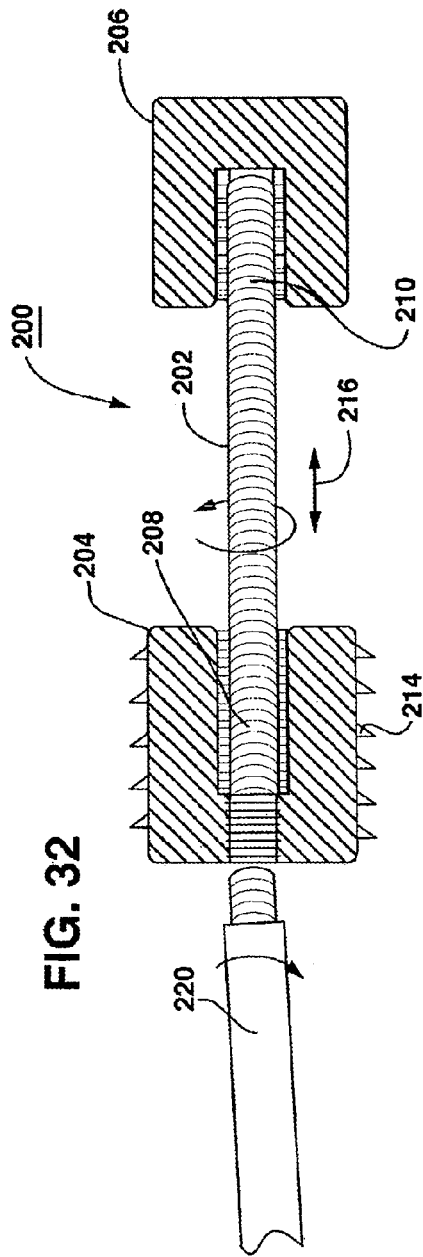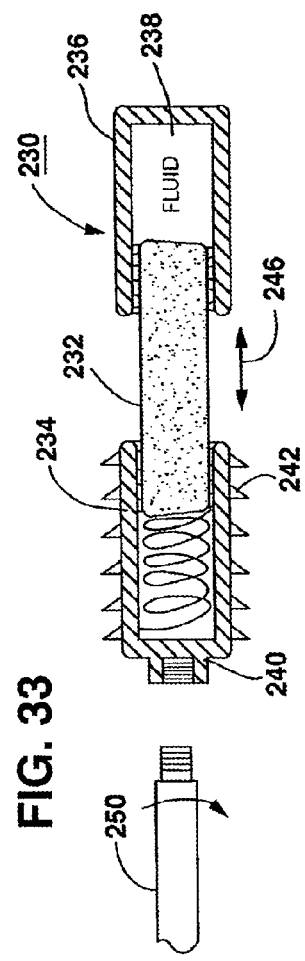

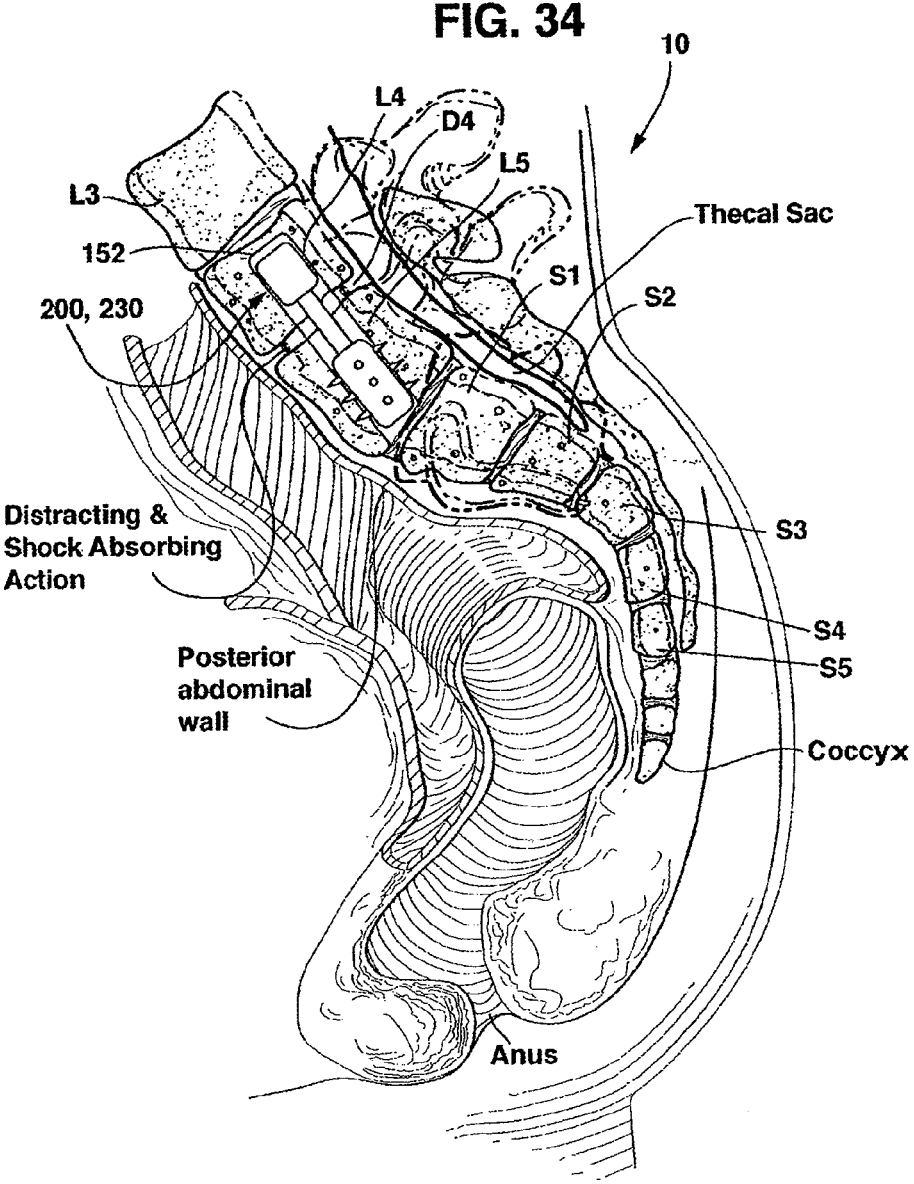

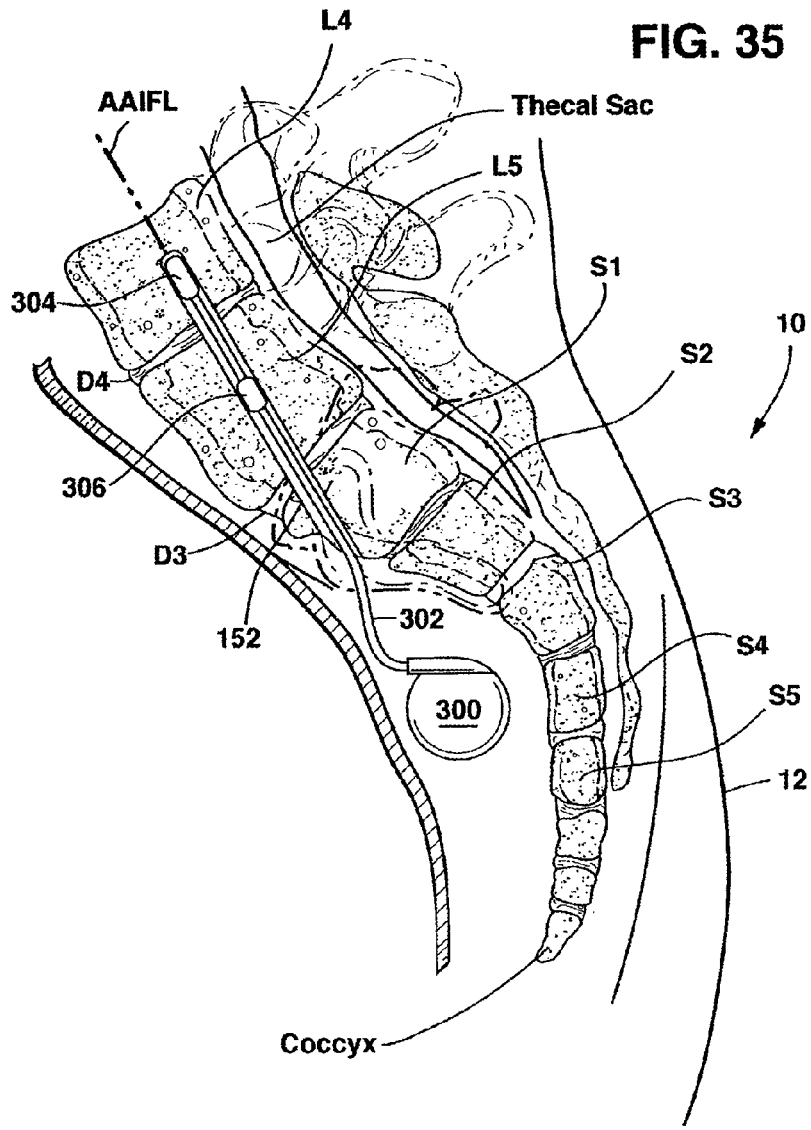

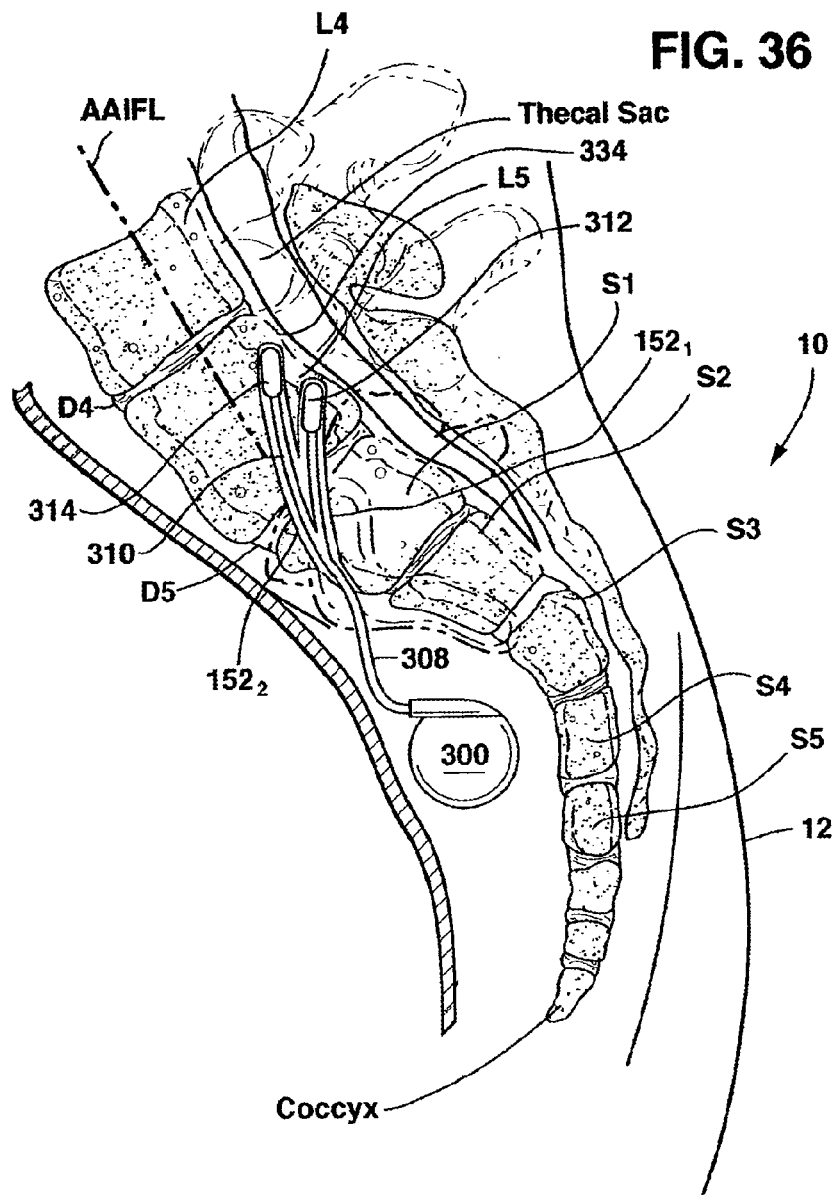

METHODS AND APPARATUS FOR PERFORMING THERAPEUTIC PROCEDURES IN THE SPINE

PRIORITY STATEMENT

This application is a continuation of U.S. patent application Ser. No. 12/856,372, filed Aug. 13, 2010, which is a continuation of U.S. patent application Ser. No. 11/956,236, filed Dec. 13, 2007, which issued as U.S. Pat. No. 7,794,463 on Sep. 14, 2010, which is a continuation of U.S. patent application Ser. No. 10/430,841, filed May 6, 2003, which issued as U.S. Pat. No. 7,309,338 on Dec. 18, 2007, which is a continuation of U.S. patent application Ser. No. 09/782,583, filed Feb. 13, 2001, which issued as U.S. Pat. No. 6,558,390 on May 6, 2003, which claims priority and benefits from Provisional Patent Application No. 60/182,748, filed Feb. 16, 2000, entitled METHOD AND APPARATUS FOR TRANS-SACRAL SPINAL FUSION.

FIELD

The present invention relates generally to spinal surgery, particularly methods and apparatus for forming one or more trans-sacral axial spinal instrumentation/fusion (TASIF) axial bore through vertebral bodies in general alignment with a visualized, trans-sacral anterior or posterior axial instrumentation/fusion line (AAIFL or PAIFL) line in a minimally invasive, low trauma, manner and providing a therapy to the spine employing the axial bore.

BACKGROUND

It has been estimated that 70% of adults have had a significant episode of back pain or chronic back pain emanating from a region of the spinal column or backbone. Many people suffering chronic back pain or an injury requiring immediate intervention resort to surgical intervention to alleviate their pain.

The spinal column or backbone encloses the spinal cord and consists of 33 vertebrae superimposed upon one another in a series which provides a flexible supporting column for the trunk and head. The vertebrae cephalad (i.e., toward the head or superior) to the sacral vertebrae are separated by fibrocartilaginous intervertebral discs and are united by articular capsules and by ligaments. The uppermost seven vertebrae are referred to as the cervical vertebrae, and the next lower twelve vertebrae are referred to as the thoracic, or dorsal, vertebrae. The next lower succeeding five vertebrae below the thoracic vertebrae are referred to as the lumbar vertebrae and are designated L1-L5 in descending order. The next lower succeeding five vertebrae below the lumbar vertebrae are referred to as the sacral vertebrae and are numbered S1-S5 in descending order. The final four vertebrae below the sacral vertebrae are referred to as the coccygeal vertebrae. In adults, the five sacral vertebrae fuse to form a single bone referred to as the sacrum, and the four rudimentary coccyx vertebrae fuse to form another bone called the coccyx or commonly the "tail bone". The number of vertebrae is sometimes increased by an additional vertebra in one region, and sometimes one may be absent in another region.

Typical lumbar, thoracic and cervical vertebrae consist of a ventral or vertebral body and a dorsal or neural arch. In the thoracic region, the ventral body bears two costal pits for reception of the head of a rib on each side. The arch which encloses the vertebral foramen is formed of two pedicles and two lamina. A pedicle is the bony process which projects backward or anteriorly from the body of a vertebra connecting with the lamina on each side. The pedicle forms the root of the vertebral arch. The vertebral arch bears seven processes: a dorsal spinous process, two lateral transverse processes, and four articular processes (two superior and two inferior). A deep concavity, inferior vertebral notch, on the inferior border of the arch provides a passageway or spinal canal for the delicate spinal cord and nerves. The successive vertebral foramina surround the spinal cord. Articulating processes of the vertebrae extend posteriorly of the spinal canal.

The bodies of successive lumbar, thoracic and cervical vertebrae articulate with one another and are separated by the intervertebral spinal discs. Each spinal disc comprises a fibrous cartilage shell enclosing a central mass, the "nucleus pulposus" (or "nucleus" herein) that provides for cushioning and dampening of compressive forces to the spinal column. The shell enclosing the nucleus comprises cartilaginous endplates adhered to the opposed cortical bone endplates of the cephalad and caudal vertebral bodies and the "annulus fibrosis" (or "annulus" herein) comprising an annular fibrosis layer of collagen fibers running circumferentially around the nucleus pulposus and connecting the cartilaginous endplates. The nucleus contains hydrophilic (water attracting) micropolysacharides and fibrous strands. The nucleus is relatively inelastic, but the annulus can bulge outward slightly to accommodate loads axially applied to the spinal motion segment.

The intervertebral discs are anterior to the spinal canal and located between the opposed end faces or endplates of a cephalad and a caudal vertebral body. The inferior articular processes articulate with the superior articular processes of the next succeeding vertebra in the caudal (i.e., toward the feet or inferior) direction. Several ligaments (supraspinous, interspinous, anterior and posterior longitudinal, and the ligamenta flava) hold the vertebrae in position yet permit a limited degree of movement. The assembly of two vertebral bodies, the interposed, intervertebral, spinal disc and the attached ligaments, muscles and facet joints is referred to as a "spinal motion segment".

The relatively large vertebral bodies located in the anterior portion of the spine and the intervertebral discs provide the majority of the weight bearing support of the vertebral column. Each vertebral body has relatively strong, cortical bone layer comprising the exposed outside surface of the body, including the endplates, and weak, cancellous bone comprising the center of the vertebral body.

A number of spinal disorders are caused by traumatic spinal injuries, disease processes, aging processes, and congenital abnormalities that cause pain, reduce the flexibility of the spine, decrease the load bearing capability of the spine, shorten the length of the spine, and/or distort the normal curvature of the spine. These spinal disorders and various treatments that have been clinically used or proposed are first described as follows.

With aging, the nucleus becomes less fluid and more viscous and sometimes even dehydrates and contracts (sometimes referred to as "isolated disc resorption") causing severe pain in many instances. In addition, the annulus tends to thicken, desiccate, and become more rigid, lessening its ability to elastically deform under load and making it susceptible to fracturing or fissuring.

One form of degeneration of the disc occurs when the annulus fissures or is rent. The fissure may or may not be accompanied by extrusion of nucleus material into and beyond the annulus. The fissure itself may be the sole morphological change, above and beyond generalized degenerative changes in the connective tissue of the disc, and disc fissures can nevertheless be painful and debilitating. Biochemicals contained within the nucleus are alleged to escape through the fissure and irritate nearby structures.

A fissure also may be associated with a herniation or rupture of the annulus causing the nucleus to bulge outward or extrude out through the fissure and impinge upon the spinal column or nerves (a "ruptured" or "slipped" disc). With a contained disc herniation, the nucleus may work its way partly through the annulus but is still contained within the annulus or beneath the posterior longitudinal ligament, and there are no free nucleus fragments in the spinal canal. Nevertheless, even a contained disc herniation is problematic because the outward protrusion can press on the spinal cord or on spinal nerves causing sciatica.

Another disc problem occurs when the disc bulges outward circumferentially in all directions and not just in one location. This occurs when over time, the disc weakens, bulges outward and takes on a "roll" shape. Mechanical stiffness of the joint is reduced and the spinal motion segment may become unstable shortening the spinal cord segment. As the disc "roll" extends beyond the normal circumference, the disc height may be compromised, and foramina with nerve roots are compressed causing pain. In addition, osteophytes may form on the outer surface of the disc roll and further encroach on the spinal canal and foramina through which nerves pass. The cephalad vertebra may eventually settle on top of the caudal vertebra. This condition is called "lumbar spondylosis".

In addition, various types of spinal column displacement disorders are known in one or more spinal motion segment that are hereditary or are caused by degenerative disease processes or trauma. Such spinal displacement disorders include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine). At times the displacement disorder is accompanied by or caused by a fracture or partial collapse of one or more vertebrae or degeneration of a disc. Patients who suffer from such conditions can experience moderate to severe distortion of the thoracic skeletal structure, diminished ability to bear loads, loss of mobility, extreme and debilitating pain, and oftentimes suffer neurologic deficit in nerve function.

Approximately 95% of spinal surgery involves the lower lumbar vertebrae designated as the fourth lumbar vertebra ("L4"), the fifth lumbar vertebra ("L5"), and the first sacral vertebra ("S1"). Persistent low back pain is attributed primarily to degeneration of the disc connecting L5 and S1. Traditional, conservative methods of treatment include bed rest, pain and muscle relaxant medication, physical therapy or steroid injection. Upon failure of conservative therapy spinal pain (assumed to be due to instability) has traditionally been treated by spinal fusion, with or without instrumentation, which causes the vertebrae above and below the disc to grow solidly together and form a single, solid piece of bone.

Highly invasive, open surgical procedures have been developed and used to perform a "complete discectomy" to surgically remove the disc, and the vertebral bodies are then fused together. The removal of the disc involves removing the nucleus, cutting away the cartilaginous endplates adhered to the opposed cortical bone endplates of the cephalad and caudal vertebral bodies, and removing at least a portion of the annulus. Fusion of the vertebral bodies involves preparation of the exposed endplate surfaces by decortication (scraping the endplate cortical bone) and the deposition of additional bone into disc space between the prepared endplate surfaces.

The complete discectomy and fusion may be performed through a posterior surgical route (from the back side of the patient) or an anterior surgical route (from the front side of the patient). The removed vertebral bone may be just the hard cortical bone or may include soft cancellous soft bone in the interior of the vertebral bodies. Controversy exists regarding the preferred method of performing these fusions for various conditions of the spine. Sometimes, non-biological materials are used to augment and support the bone grail (fixation systems). Sometimes, the fixation is performed from the posterior route (posterior fixation), or from the anterior route (anterior fixation), or even both sides (anterior-posterior fixations or circumferential fusion).

Current treatment methods other than spinal fusion for symptomatic disc rolls and herniated discs include "laminectomy" which involves the lateral surgical exposure of the annulus and surgical excision of the symptomatic portion of the herniated disc followed by a relatively lengthy recuperation period.

Various other surgical treatments that attempt to preserve the intervertebral spinal disc and to simply relieve pain include a "nucleotomy" or "disc decompression" to remove some or most of the interior nucleus thereby decompressing and decreasing outward pressure on the annulus. In less invasive microsurgical procedures known as "microlumbar discectomy" and "automated percutaneous lumbar discectomy", the nucleus is removed by suction through a needle laterally extended through the annulus. Although these procedures are less invasive than open surgery, they nevertheless suffer the possibility of injury to the nerve root and dural sac, perineural scar formation, reherniation of the site of the surgery, and instability due to excess bone removal. Moreover, they involve the perforation of the annulus.

Another method of treatment is known as "chemonucleolysis", which is carried out by injection of the enzyme chymopapain into the nucleus through the annulus. This procedure has many complications including severe pain and spasm, which may last up to several weeks following injection. Sensitivity reactions and anaphylactic shock occur in limited but significant numbers of patients.

Although damaged discs and vertebral bodies can be identified with sophisticated diagnostic imaging, the surgical procedures are so extensive that clinical outcomes are not consistently satisfactory. Furthermore, patients undergoing such fusion surgery experience significant complications and uncomfortable, prolonged convalescence. Surgical complications include disc space infection, nerve root injury, hematoma formation, and instability of adjacent vertebrae.

Many surgical techniques, instruments and spinal disc implants have been described in the medical literature and in patents that are directed to providing less invasive, percutaneous, lateral access to a degenerated intervertebral spinal disc. Then, instruments are introduced through lateral disc openings made through the annulus for performing a discectomy and implanting bone growth materials or biomaterials or spinal disc implants inside the annulus. Or, one or more laterally extending space or hole is bored through the disc to receive one or more laterally inserted spinal disc implant or bone growth material to promote fusion or to receive a preformed, artificial, functional disc replacement implant as typified by U.S. Pat. No. 5,700,291.

Percutaneous lateral procedures and instruments for performing such discectomies are disclosed in U.S. Pat. Nos. Re. 33,258, 4,573,448, 5,015,255, 5,313,962, 5,383,884, 5,702, 454, 5,762,629, 5,976,146, 6,095,149, and 6,127,597 and in PCT publication WO 99/47055, for example. A laparascopic technique and apparatus for traversing the retroperitoneal space from an abdominal skin incision to an anterior surface of the disc annulus and performing a discoscopy is disclosed in the '962 patent, for example. Percutaneous surgical disc procedures and apparatus that accesses the disc in a posterolateral approach from a skin incision in the patient's back are described in the '629 and '448 patents, for example.

The nucleus is fragmented by various mechanical cutting heads as disclosed, for example in the '258, '962, '884, and '597 patents, for example. Or, thermal or laser energy is applied to desiccate the nucleus and to stiffen the annulus as described in the '149 patent, for example. Or, the nucleus and portions of the cephalad and caudal vertebral bodies are mechanically cut away to enlarge the disc space as described in the PCT '055 publication and in the '255 patent, for example. Irrigation fluid is introduced into the disc space or cavity and the fragments or desiccation by-products of the nucleus and any bone and annulus fragments are aspirated from the disc space or cavity. The irrigation and aspiration is effected through an access cannula positioned against the opening through the annulus of the herniated disc as disclosed in the '629 patent, for example, or through a lumen of the discectomy instrument, as disclosed in the '258 patent, for example. A measure of safety and accuracy is added to these operative procedures by the artiroscopic visualization of the annulus and other important structures which lie in the path of the instruments, such as the spinal nerve.

The above-described procedures involve invasive surgery that laterally exposes the anterior or posterior (or both) portions of the vertebrae and intervertebral spinal disc. Extensive muscular stripping and bone preparation can be necessary. As a result, the spinal column can be further weakened and/or result in surgery induced pain syndromes. Thus, presently used or proposed surgical fixation and fusion techniques involving the lower lumbar vertebrae suffer from numerous disadvantages.

Methods and apparatus for accessing the discs and vertebrae by lateral surgical approaches that purportedly reduce muscular stripping (and that are similar to those disclosed in the above-referenced '629 and '888 patents) are described in U.S. Pat. No. 5,976,146. The intervening muscle groups or other tissues are spread apart by a cavity forming and securing tool set disclosed in the '146 patent to enable endoscope aided, lateral access to damaged vertebrae and discs and to perform corrective surgical procedures. However, it is preferable to avoid the lateral exposure to correct less severe spondylolisthesis and other spinal injuries or defects affecting the lumbar and sacral vertebrae and discs.

A less intrusive posterior approach for treating spondylolisthesis is disclosed in U.S. Pat. No. 6,086,589, wherein a straight bore is formed through the sacrum from the exposed posterior sacral surface and in a slightly cephalad direction into the L5 vertebral body, preferably after realigning the vertebrae. A straight, hollow, threaded shaft with side wall holes restricted to the end portions thereof and bone growth material are inserted into the bore. A discectomy of the disc between L5 and S1 is preferably performed in an unexplained manner, and bone ingrowth material is also preferably inserted into the space between the cephalad and caudal vertebral bodies. Only a limited access to and alignment of S1 and L5 can be achieved by this approach because the distal ends of the straight bore and shaft approach and threaten to perforate the anterior surface of the L5 vertebral body. This approach is essentially a posteriolateral approach that is intended to fuse S1 and L5 and cannot access more cephalad vertebral bodies or intervertebral spinal discs.

In many of these procedures, a laterally extending space is prepared by removal of the disc to receive one or more disc implant, and insertion of a bone growth material, e.g. autologous bone, or a pre-formed, artificial, functional disc replacement implant. A number of disc shaped, functional disc replacement implants and methods of insertion have been proposed as disclosed, for example, in U.S. Pat. Nos. 5,258,031 and 6,019,792, for example. Other disc shaped or vertebral body replacement implants that are designed to encourage bone growth and effect fusion are shown in U.S. Pat. Nos. 5,514,180 and 5,888,223, for example. These devices and techniques are intended to overcome the disadvantages of purely surgical techniques to mechanically immobilize areas of the spine assisting in the eventual fusion of the treated adjacent vertebrae, and to maintain the length of the treated spinal motion segment to avoid shortening spinal cord and nerve segments. However, they require relatively large lateral exposure of the disc or vertebral body to excise the disc or vertebral body, shape the adjoining caudal and cephalad vertebral bodies and effect the implantation and fixation thereto. Thus, disadvantages to the present implants and surgical implantation techniques remain concerning the implantation procedures and involving post-surgical failure necessitating re-operation.

A further type of disc implant that has been clinically employed for spinal fusion comprises a hollow, cylindrical, titanium cage that is externally threaded and is screwed laterally into place in a lateral bore formed through the disc between two adjacent vertebrae. Typically, the lateral bore involves complete discectomy of the damaged disc and removal of portions of the cortical bone of the adjoining vertebral bodies to prepare a laterally and axially extending space to receive one or more disc implant. Bone grafts from cadavers or the pelvis or substances that promote bone growth are then packed into the hollow center of the cage to encourage bone growth (or ingrowth) through the cage pores to achieve fusion of the two adjacent vertebrae. Two such cage implants and the surgical tools employed to place them are disclosed in U.S. Pat. Nos. 5,505,732 and 5,700,291, for example. The cage implants and the associated surgical tools and approaches require precise drilling of a relatively large hole for each such cage laterally between two adjacent vertebral bodies and then threading a cage into each prepared hole. The exposed ends of the cage or side by side installed cages can irritate nerves causing pain to emerge again.

These approaches involve a virtually complete discectomy of the disc achieved by instruments introduced laterally through the patient's body to the disc site and manipulated to cut away or drill lateral holes through the disc and adjoining cortical bone. The large laterally drilled hole or holes can compromise the integrity of the vertebral bodies, and the spinal cord can be injured if they are drilled too posteriorly. The endplates of the vertebral bodies, which comprise very hard cortical bone and help to give the vertebral bodies needed strength, are usually weakened or destroyed during the drilling. The cylindrical cage or cages are now harder than the remaining bone of the vertebral bodies, and the vertebral bodies tend to collapse or "telescope" together. The telescoping causes the length of the vertebral column to shorten and can cause damage to the spinal cord and nerves that pass between the two adjacent vertebrae.

Therefore, it is often necessary to also mechanically stabilize the vertebrae on either side of the spinal disc that is augmented or removed so that fusion of the vertebral bodies can occur successfully without telescoping of the vertebral bodies or movement of the disc implants out of the prepared site. One technique for spinal fixation includes the immobilization of the spine by the use of spine rods of many different configurations that run generally parallel to the spine. Typically, the posterior surface of the spine is isolated and bone screws are first fastened to the pedicles of the appropriate vertebrae or to the sacrum and act as anchor points for the spine rods. The bone screws are generally placed two per vertebra, one at each pedicle on either side of the spinous process. Clamp assemblies join the spine rods to the screws. The spine rods are generally bent to achieve the desired curvature of the spinal column. Wires may also be employed to stabilize rods to vertebrae. These techniques are described further in U.S. Pat. No. 5,415,661, for example.

These types of rod systems can be effective, but require a posterior approach and implanting screws into or clamps to each vertebra over the area to be treated. To stabilize the implanted system sufficiently, one vertebra above and one vertebra below the area to be treated are often used for implanting pedicle screws. Since the pedicles of vertebrae above the second lumbar vertebra (L2) are very small, only small bone screws can be used which sometimes do not give the needed support to stabilize the spine. These rods and screws and clamps or wires are surgically fixed to the spine from a posterior approach, and the procedure is difficult. A large bending moment is applied to such rod assemblies, and because the rods are located outside the spinal column, they depend on the holding power of the associated components which can pull out of or away from the vertebral bone.

In a further approach disclosed in U.S. Pat. Nos. 4,553,273 and 4,636,217, both described in U.S. Pat. No. 5,735,899, two of three vertebrae are joined by surgically obtaining access to the interior of the upper and lower vertebral bodies through excision of the middle vertebral body. In the '899 patent, these approaches are referred to as "intraosseous" approaches, although they are more properly referred to as "interosseous" approaches by virtue of the removal of the middle vertebral body. The removal is necessary to enable a lateral insertion of the implant into the space it occupied so that the opposite ends of the implant can be driven upward and downward into the upper and lower vertebral bodies. These approaches are criticized as failing to provide adequate medial-lateral and rotational support in the '899 patent. In the '899 patent, an anterior approach is made, slots are created in the upper and lower vertebrae, and rod ends are fitted into the slots and attached to the remaining vertebral bodies of the upper and lower vertebrae by laterally extending screws. These approaches involve considerable damage to ligaments and tissue in the anterior access to the vertebral bones.

The use of radiopaque metal cages or other metal implants also makes it difficult to image the disc space with radiographic imaging equipment to assess the degree of fusion achieved by bone growth between the vertebral bodies separated by the cages. Laterally insertable, rigid carbon fiber and more flexible polymeric disc implants are under study as replacements for metal implants.

Alternatively, the use of a deflated porous fabric bag that is laterally inserted into a prepared cavity and inflated with bone growth encouraging material is disclosed in U.S. Pat. No. 5,549,679. The prepared cavity is substantially ovaloid and includes the removed disc and a portion of the adjoining vertebral bodies. The filling of the bag under pressure tends to distract, i.e., to separate, the adjoining vertebral bodies to the physiologic separation that would be provided by the undamaged disc. The porous bag opening is closed in a number of ways to retain the material it is filled with. This porous bag is distinguished from several other artificial disc designs described in the '679 patent, including an artificial disc with an elastomeric core (U.S. Pat. No. 5,071,437) or filled with hydrogel beads (U.S. Pat. No. 5,192,326).

In a further disc augmentation approach described in U.S. Pat. No. 5,888,220, the disc is accessed laterally through the patient's body, the annulus is perforated unless it is already rent, and a partial discectomy is performed to remove most or all of the nucleus to create a space within the annulus. Then, a mass of curable biomaterials is injected into the prepared space and the material is cured in situ. In one variation, a deflated balloon is inserted into the prepared space, and the mass of curable biomaterials is injected into the prepared space and the material is cured in situ, leaving the filled balloon and solidified biomaterial in place.

A compilation of many of the above described surgical techniques and spinal implants and others that have been used clinically is set forth in certain chapters of the book entitled *Lumbosacral and Spinopelvic Fixation*, edited by Joseph Y. Margolies et al. (Lippincott-Raven Publishers, Philadelphia, 1996). Attention is directed particularly to Chapters 1, 2, 17, 18, 38, 42 and 44.

In "Lumbopelvic Fusion" (Chapter 38, by Prof. Rene P. Louis, MD) techniques for repairing a spondylolisthesis, in this case, a severe displacement of L5 with respect to S1 and the intervening disc, are described and depicted. An anterior lateral exposure of L5 and S1 is made, a discectomy is performed, and the orientation of L5 to S1 is mechanically corrected using a reduction tool, if the displacement is severe. A fibula graft or metal Judet screw is inserted as a dowel through a bore formed extending caudally through L5 and into S1. When the screw is used, bone growth material, e.g., bone harvested from the patient, is inserted into the bore alongside the screw, and the disc space is filled with bone sutured to the screw to keep it in place between the vertebral surfaces to act as a spacer implant occupying the extracted disc between L5 and S1. External bridge plates or rods are also optionally installed. The posterolateral or anterior lateral approach is necessitated to correct the severe spondylolisthesis displacement using the reduction tool and results in tissue injury. Because of this approach and need, the caudal bore and inserted the Judet screw can only traverse L5 and S1.

A similar anterior approach for treating spondylolisthesis is disclosed in U.S. Pat. No. 6,056,749. In this approach, a bore hole is formed in a cephalad vertebral body and extends through the intervening disc into a caudal vertebral body, the disc is removed, a disk cage is inserted laterally into the disc space, and an elongated, hollow threaded shaft is inserted into the bore and through a hole in the disc cage. The disk cage takes the place of the harvested bone disc inserts and its interlocking intersection with the shaft takes the place of the sutures employed to tie the harvested bone disc inserts to the screw in the technique described in the above-referenced Chapter 38 publication.

Turning to a further spinal disorder, the vertebral bodies can thin and weaken with the development and progression of osteoporosis and certain eating disorders to the point that one or more vertebral body compression fractures occur as described in U.S. Pat. Nos. 4,969,888, 5,972,015 and 6,066,154. Vertebral compression fractures of healthy vertebral bodies can also occur due to injury. In severe cases, the vertebral body tends to collapse, shortening the vertebral body and the spine and inducing an aberrant localized spinal curvature. As noted in the '888 patent, osteoporotic vertebral body compression fractures are currently treated with bed rest, analgesics, and intravenous hydration during the first week after onset of the problem. These steps are followed by the prescription of a soft or firm spinal corset, depending upon the physician's preference. In most cases, the corset is not worn because the patient suffers much discomfort and oftentimes greater discomfort than that due to the fracture of the vertebral body. The fracture pain lasts from two to eight months. In many cases, patients with osteoporotic vertebral body collapse fractures require about one week in an acute care hospital and two to three weeks in an extended care facility until they are able to move about independently and with only moderate pain. Current treatment does not substantially alter the conditions of the vertebral body.

The '888 patent describes a "balloon-assisted vertebroplasty" method of restoring the vertical height of a collapsed, compression fractured vertebral bone through a posterolateral approach from an entry point on the skin determined radiologically and is located approximately 10 cm from the midline and just inferior to a rib if present at that level. A guide pin is extended from the incision to the vertebral body and through the cortical bone and a predetermined distance into the cancellous bone. A cannula is inserted over the guide pin and its distal end is attached to the exterior cortical bone of the vertebral body. A drill is extended through the cannula and used to drill a hole into the cancellous bone to enlarge the cavity to be treated. A deflated, expandable balloon is inserted through the cannula and inflated inside the vertebral body into a disc or checker shape. The expansion of the balloon compacts the cancellous bone against the inner surface of the outer cortical wall of the vertebral body thereby further enlarging the cavity and, it is asserted, filling the fractures in the cortical bone. The balloon expansion may also restore the height of the vertebral body to some extent. The balloon is then deflated and removed, and the cavity is irrigated with saline. The cavity is simultaneously aspirated and filled with a flowable synthetic bone material or methyl methacrylate cement that is allowed to set to a hardened condition through the cannula. It is asserted that the compacted cortical bone or bone marrow will substantially prevent flow through the fracture.

The '015 and '154 patents disclose generally the same procedure steps but employ improved, irregularly shaped, balloons that approximate the inner shape of the vertebral bodies they are inflated within in order to maximally compress cancellous bone. The balloons are made of inelastic material and are kept in their defined configurations when inflated by various shape restraints. This procedure is also referred to as a "Kyphoplasty", by Kyphon, Inc., the assignee of the '015 and '154 patents.

There are other therapeutic treatments for encouraging bone growth within a vertebral body or to fuse vertebral bodies together with or without a pre-formed spinal disc replacement implant that involve injection of bone growth materials into the disc or vertebral body or the application of electrical energy to stimulate bone growth. Several natural or artificial osteoconductive, osteoinductive, osteogenic or other fusion enhancing materials are disclosed in U.S. Pat. No. 6,123,705. A system and method for delivering electrical energy to a pre-formed spinal disc replacement implant to promote bone growth and fusion about the implant and between the opposed endplates of the cephalad and caudal vertebral bodies are disclosed in U.S. Pat. No. 6,120,502.

The above-described procedures involve invasive surgery that laterally exposes the anterior or posterior (or both) portions of the vertebrae and intervertebral disc. Extensive muscular stripping and bone preparation can be necessary. As a result, the spinal column can be further weakened and/or result in surgery induced pain syndromes. Thus, presently used or proposed surgical fixation and fusion techniques involving the lower lumbar vertebrae suffer from numerous disadvantages.

Methods and apparatus for accessing the discs and vertebrae by lateral surgical approaches that purportedly reduce muscular stripping (and that are similar to those disclosed in the above-referenced '629 and '888 patents) are described in U.S. Pat. No. 5,976,146. The intervening muscle groups or other tissues are spread apart by a cavity forming and securing tool set disclosed in the '146 patent to enable endoscope aided, lateral access to damaged vertebrae and discs and to perform corrective surgical procedures. However, it is preferable to avoid the lateral exposure to correct less severe spondylolisthesis and other spinal injuries or defects affecting the lumbar and sacral vertebrae and discs.

A less intrusive posterior approach for treating spondylolisthesis is disclosed in U.S. Pat. No. 6,086,589, wherein a straight bore is formed through the sacrum from the exposed posterior sacral surface and in a slightly cephalad direction into the L5 vertebral body, preferably after realigning the vertebrae. A straight, hollow, threaded shaft with side wall holes restricted to the end portions thereof and bone growth material are inserted into the bore. A discectomy of the disc between L5 and S1 is preferably performed and bone ingrowth material is also preferably inserted into the space between the cephalad and caudal vertebral bodies. Only a limited access to and alignment of S1 and L5 can be achieved by this approach because the distal ends of the straight bore and shaft approach and threaten to perforate the anterior surface of the L5 vertebral body. This approach is essentially a posteriolateral approach that is intended to fuse S1 and L5 and cannot access more cephalad vertebral bodies or intervertebral discs.

A wide variety of orthopedic implants have also been proposed or clinically employed to stabilize broken bones or secure artificial hip, knee and finger joints. Frequently, rods or joint supports are placed longitudinally within longitudinal bores made in elongated bones, e.g., the femur. A surgical method is disclosed in U.S. Pat. No. 5,514,137 for stabilizing a broken femur or other long bones using an elongated rod and resorbable cement. To accomplish a placement of a rod into any single bone, an end of a bone is exposed and a channel is drilled from the exposed end to the other end. Thereafter, a hollow rod is inserted, and resorbable cement is injected through the hollow rod, so as to provide fixation between the distal end of the rod and the cancellous tissue that surrounds the rod. A cement introducer device can also be used for the injection of cement. A brief reference is made in the '137 patent to the possibility of placing rods in or adjacent to the spine in the same manner, but no particular approach or devices are described.

Drilling tools are employed in many of the above described surgical procedures to bore straight holes into the vertebral bones. The boring of curved bores in other bones is described in U.S. Pat. Nos. 4,265,231, 4,541,423, and 5,002,546, for example. The '231 patent describes an elongated drill drive shaft enclosed within a pre-curved outer sheath that is employed to drill curved suture holding open ended bores into bones so that the suture passes through both open ends of the bore. The '423 patent describes an elongated flexible drill drive shaft enclosed within a malleable outer sheath that can be manually shaped into a curve before the bore is formed. The '546 patent describes a complex curve drilling tool employing a pivotal rocker arm and curved guide for a drill bit for drilling a fixed curve path through bone. All of these approaches dictate that the curved bore that is formed follow the predetermined and fixed curvature of the outer sheath or guide. The sheath or guide is advanced through the bore as the bore is made, making it not possible for the user to adjust the curvature of the bore to track physiologic features of the bone that it traverses.

All of the above-described patents and other patents referenced herein that access a single spinal disc or vertebra to perform the above-described therapies, do so from a lateral approach that involves weakening of the spinal fusion segment. There remains a need for methods and apparatus for performing therapeutic procedures in the spine in a minimally invasive, low trauma, manner.

SUMMARY

The preferred embodiments of the invention involve methods and apparatus for performing such therapeutic procedures of one or more of a series of vertebral bodies or any spinal discs or other spinal structures to be treated of the human spine having an anterior aspect, a posterior aspect and an axial aspect, in a minimally invasive, low trauma, manner. The present invention is practiced employing methods of and corresponding apparatus for:

accessing an anterior or posterior sacral position of a sacral vertebra in alignment with a visualized, trans-sacral AAIFL or PAIFL extending cephalad through the series of adjacent vertebral bodies and any intervertebral discs;

from the accessed sacral position, forming a TASIF axial bore in alignment with the AAIFL or PAIFL cephalad and axially through the vertebral bodies of at least the sacral vertebrae and into or through at least one lumbar vertebral body and into or through any intervertebral spinal discs thereby forming an axial disc opening; and performing a therapeutic procedure of one or more of the series of adjacent vertebral bodies or intact or damaged intervertebral spinal discs.

The accessing of the anterior sacral position is preferably performed by forming an anterior access tract from a skin incision through presacral space to the anterior target point. The accessing of the posterior sacral position is preferably performed by surgically exposing the posterior target point.

One or more posterior TASIF axial bore is formed starting from the exposed posterior target point and extending in the cephalad direction in alignment with the visualized, trans-sacral PAIFL. The posterior TASIF axial bore(s) has a curvature aligned with the anatomical curvature of the sacral and lumbar vertebrae cephalad to the posterior target point so that the posterior trans-sacral axial bore(s) can extend in the cephalad direction to a cephalad bore end in one of the lumbar vertebral bodies or discs.

One or more anterior TASIF axial bore is formed starting from the accessed anterior target point and extending axially (that is in the axial direction of the spinal column) in the cephalad direction in alignment with the visualized trans-sacral AAIFL. The anterior TASIF axial bore(s) is either straight or is curved to follow the anatomical curvature of the sacral and lumbar vertebrae cephalad to the accessed anterior target point and extend in the cephalad direction to a cephalad bore end in one of the lumbar vertebral bodies or discs.

In either case, the "alignment" of a single anterior or posterior TASIF axial bore is either co-axial or parallel alignment with the visualized AAIFL or PAIFL, respectively. The alignment of a plurality of anterior or posterior TASIF axial bores is either parallel or diverging alignment with the visualized AAIFL or PAIFL, respectively. All such alignments are defined herein as axial.

The therapeutic procedures comprise one or more of: (1) performing a vertebroplasty or balloon-assisted vertebroplasty to a fractured vertebral body accessed through a TASIF axial bore; (2) performing a partial discectomy or complete discectomy of a disc accessed through a TASIF axial bore; (3) inserting bone growth material into the disc space following a complete discectomy of a disc accessed through a TASIF axial bore to effect fusion; (4) inserting an artificial disc implant into the disc space to replace the disc accessed and removed through a TASIF axial bore; (5) following a partial discectomy, inserting an artificial disc implant or other disc implant or a biomaterial into the space within the annulus to augment the disc accessed through a TASIF axial bore; (6) inserting axial spinal implants into the TASIF axial bore(s), including axial spinal implants providing distraction of two or more vertebrae across one or more intervertebral disc and/or shock absorption due to loads applied axially to the spine; (7) providing electrical stimulation of a spinal structure of interest through a TASIF axial bore to encourage bone growth or to counter pain or in operative relation to the spinal column or nerves to counter pain; (8) providing drug delivery to a spinal structure of interest through a TASIF axial bore to encourage bone growth or to counter pain or in operative relation to the spinal column or nerves to counter pain; (9) implanting radioactive seeds within vertebral bodies to treat metastatic disease in the spine or adenopathy in the retroperitoneum; and (10) performing a diagnostic procedure, e.g. directly inspecting the spine through the bore.

In the context of the present invention, a "partial discectomy" involves removal or desiccation of any portion of the nucleus through the axial disc opening, whereas a "complete discectomy" involves perforation or removal of at least some of the annulus of the intervertebral spinal disc.

The anterior or posterior TASIF axial bore(s) can therefore be employed to remove vertebral bone and/or spinal disc material, to introduce bone growth materials, other biomaterials, devices and instruments for completing the steps of each therapy procedure. When the procedure is completed, the TASIF axial bore(s) are preferably filled to seal the vertebral body(s) and disc(s), to retain the implanted devices and materials in place and/or to align, to fuse and/or to reinforce a fusion zone or the spinal motion segment. The TASIF axial bores can be filled completely or plugged in a section thereof with bone growth materials or pre-formed axial spinal implants or plugs that engage vertebral bone.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIGS. 1-3 are lateral, posterior and anterior views of the lumbar and sacral portion of the spinal column depicting the visualized PAIFL and AAIFL extending cephalad and axially from the posterior laminectomy site and the anterior target point, respectively;

FIG. 4 is a sagittal caudal view of lumbar vertebrae depicting a TASIF axial spinal implant or rod within a TASIF axial bore formed following the visualized PAIFL or AAIFL of FIGS. 1-3;

FIG. 5 is a sagittal caudal view of lumbar vertebrae depicting a plurality, e.g., 2, TASIF axial spinal implants or rods within a like plurality of TASIF axial bores formed in parallel with the visualized PAIFL or AAIFL of FIGS. 1-3;

FIG. 6 is a simplified flow chart showing the principal surgical preparation steps of percutaneously accessing a posterior or anterior target point of the sacrum and forming a percutaneous tract following the visualized PAIFL or AAIFL of FIGS. 1-3, as well as subsequent steps of forming the TASIF bore(s) for treatment of accessed vertebral bodies and intervening discs and of implanting axial spinal implants therein;

FIG. 7 illustrates, in a partial cross-section side view, one manner of obtaining access to a posterior target point for forming a posterior TASIF axial bore through sacral and lumbar vertebrae and intervening discs axially aligned with the visualized PAIFL of FIGS. 1 and 2;

FIG. 32 is a side view of an elongated axial spinal implant providing a distraction function;

FIG. 33 is a side view of an elongated axial spinal implant providing a shock absorbing function;

FIG. 34 illustrates, in a partial cross-section side view, the insertion of an axial spinal implant providing distraction or shock absorbing of two or more vertebrae across one or more intervertebral disc into a TASIF axial bore;

FIGS. 35-37 illustrate, in partial cross-section side views, extending an electrical lead from an implanted or external electrical stimulator through a TASIF axial bore to locate one or more electrical stimulation electrode of the lead within or between or outside adjoining vertebral bodies to apply electrical stimulation to encourage bone growth or to counter pain or outside adjoining vertebral bodies to counter pain;

DETAILED DESCRIPTION

Figure 8:
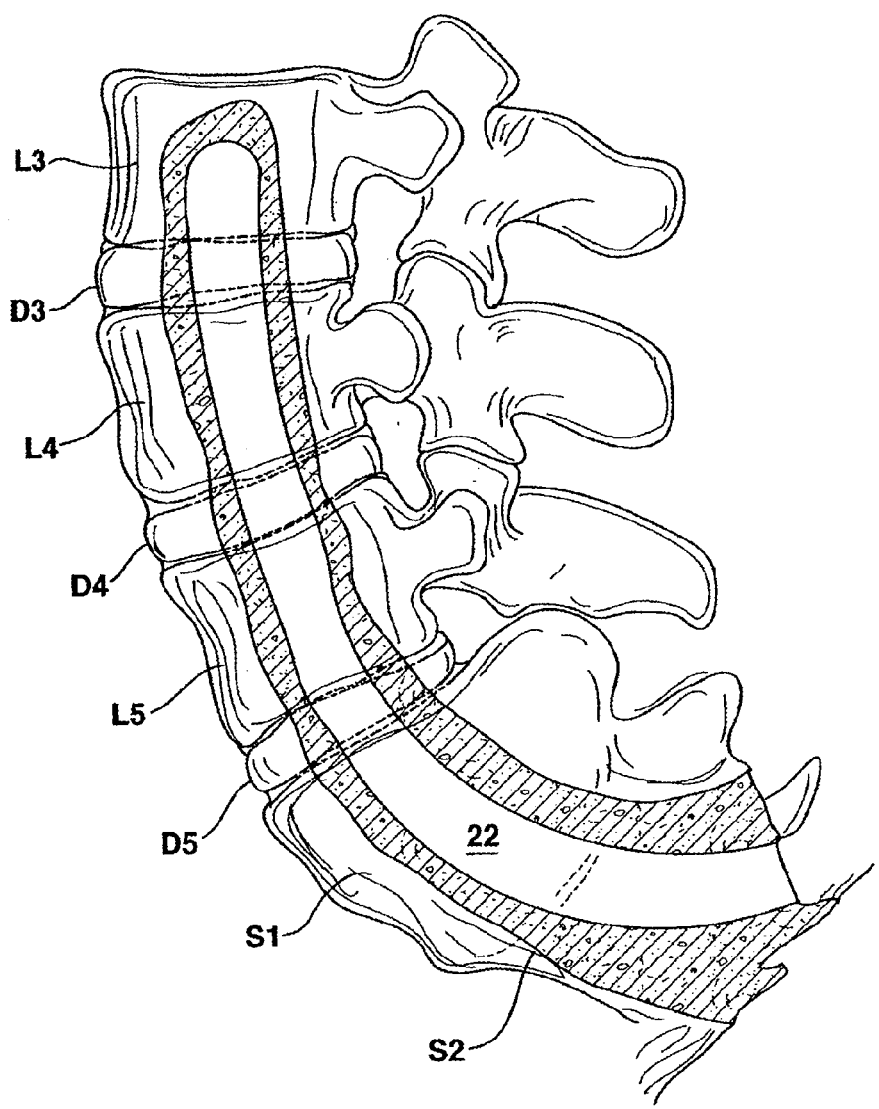
FIG. 8 is an enlarged partial cross section view illustrating a posterior TASIF axial bore through sacral and lumbar vertebrae and intervening discs axially aligned with the visualized PAIFL of FIGS. 1 and 2.

The methods and surgical instrumentation and axial spinal implants disclosed in the above-referenced provisional application No. 60/182,748 and in the above-referenced co-pending, commonly assigned, related patent applications can be employed in the practice of the present invention.

Attention is first directed to the following description of FIGS. 1-6 is taken from the above-referenced parent provisional application No. 60/182,748. The acronyms TASF, AAFL, and PAFL used in the '748 application are changed to TASIF, AAIFL and PAIFL in this application to explicitly acknowledge that instruments can be introduced for inspection or treatments in addition to the fusion and fixation provided by axial spinal implants that may be inserted into the axial bores or pilot holes.

FIGS. 1-3 schematically illustrate the anterior and posterior TASIF surgical approaches in relation to the lumbar region of the spinal column, and FIGS. 4-5 illustrate the location of the TASIF implant or pair of TASIF implants within a corresponding posterior TASIF axial bore 22 or anterior TASIF axial bore 152 or pair of TASIF axial bores 22$_1$, 22$_2$ or 152$_1$, 152$_2$. Two TASIF axial bores and axial spinal implants or rods are shown in FIG. 5 to illustrate that a plurality, that is two or more, of the same may be formed and/or employed in side by side relation in parallel alignment with the AAIFL or PAIFL or diverging from the AAIFL or PAIFL in the cephalad direction. Preferred TASIF surgical approaches for providing anterior and posterior trans-sacral access depicted in FIGS. 1-3 and preparing the TASIF axial bores 22 or 152 or 22$_1$, 22$_2$, or 152$_1$, 152$_2$ shown in FIGS. 4 and 5 are illustrated in the above-referenced '105 and '748 applications.

The lower regions of the spinal column comprising the coccyx, fused sacral vertebrae S1-S5 forming the sacrum, and the lumbar vertebrae L1-L5 described above are depicted in a lateral view in FIG. 1. The series of adjacent vertebrae located within the human lumbar and sacral spine have an anterior aspect, a posterior aspect and an axial aspect, and the lumbar vertebrae are separated by intact or damaged intervertebral spinal discs labeled D1-D5 in FIG. 1. FIGS. 2 and 3 depict the posterior and anterior views of the sacrum and coccyx.

The method and apparatus for forming an anterior or posterior TASIF axial bore initially involves accessing an anterior sacral position, e.g. an anterior target point at the junction of S1 and S2 depicted in FIGS. 1 and 3, or a posterior sacral position, e.g. a posterior laminectomy site of S2 depicted in FIGS. 1 and 2. One (or more) visualized, imaginary, axial instrumentation/fusion line extends cephalad and axially in the axial aspect through the series of adjacent vertebral bodies, L4 and L5 in this illustrated example. The visualized AAIFL through L4, D4, L5 and D5 extends relatively straight from the anterior target point along S1 depicted in FIGS. 1 and 3, but may be curved as to follow the curvature of the spinal column in the cephalad direction. The visualized PAIFL extends in the cephalad direction with more pronounced curvature from the posterior laminectomy site of S2 depicted in FIGS. 1 and 2. A preoperative CT scan or magnetic resonance imaging (MRI) study of the patient's spine is conducted to visualize and map the AAIFL or PAIFL.

FIG. 6 depicts, in general terms, the surgical steps of accessing the anterior or posterior sacral positions illustrated in FIGS. 1-3 (S100) forming posterior and anterior TASIF axial bores (S200), optionally inspecting the discs and vertebral bodies, performing discectomy or discoscopy, disc augmentation, and vertebral bone reinforcement balloon-assisted vertebroplasty or vertebroplasty (S300), and implanting posterior and anterior axial spinal implants and rods or plugs into the axial bore(s) (S400) in a simplified manner. In step S100, access to the anterior or posterior sacral position, that is the anterior target point of FIG. 3 or the posterior laminectomy site of FIG. 2 is obtained, and the anterior or posterior sacral position is penetrated to provide a starting point for each axial bore that is to be created. Then, one or more axial bore is bored from each point of penetration extending in alignment with either the PAIFL or AAIFL cephalad and axially through the vertebral bodies of the series of adjacent vertebrae and any intervertebral spinal discs (S200). The axial bore(s) can traverse one or more vertebral body cephalad to the sacral vertebral bodies S1, S2 and any intervertebral disc and can terminate at a cephalad end within a particular vertebral body or spinal disc. The axial bore may be visually inspected using an endoscope to determine if the procedures of step S300 should be performed.

The performance of step S100 in the anterior and/or posterior TASIF procedures may involve drilling a pilot hole, smaller in diameter than the TASIF axial bore, in the prescribed alignment with the AAIFL and/or PAIFL in order to complete the formation of the anterior and/or posterior percutaneous tracts. Certain of the therapeutic procedures of steps S300 and S400 may optionally be completed through the AAIFL/PAIFL pilot hole following step S100, rather than following the enlargement of the pilot hole to form the TASIF axial bore in step S200.

Step S100 preferably involves creation of an anterior or posterior percutaneous pathway that enables introduction of further tools and instruments for forming an anterior or posterior percutaneous tract extending from the skin incision to the respective anterior or posterior target point of the sacral surface or, in some embodiments, the cephalad end of a pilot hole over which or through which further instruments are introduced as described in the above-referenced '222 application. An "anterior, presacral, percutaneous tract" 26 (FIG. 1) extends through the "presacral space" anterior to the sacrum. The posterior percutaneous tract or the anterior, presacral, percutaneous tract is preferably used to bore one or more respective posterior or anterior TASIF bore in the cephalad direction through one or more lumbar vertebral bodies and intervening discs, if present. "Percutaneous" in this context simply means through the skin and to the posterior or anterior target point, as in transcutaneous or transdermal, without implying any particular procedure from other medical arts. The percutaneous pathway is generally axially aligned with the AAIFL or the PAIFL extending from the respective anterior or posterior target point through at least one sacral vertebral body and one or more lumbar vertebral body in the cephalad direction as visualized by radiographic or fluoroscopic equipment.

It should be noted that the formation of the anterior tract 26 shown in FIG. 1 through presacral space under visualization described above is clinically feasible as evidenced by clinical techniques described by J. J. Trambert, MD, in "Percutaneous Interventions in the Presacral Space: CT-guided Precoccygeal Approach—Early Experience (*Radiology*; 213:901-904).

Certain of the therapeutic procedures of the present invention are conducted through relatively straight or curved anterior TASIF bores or curved posterior TASIF bores or pilot holes. Introduction of axial spinal implants and instruments for performing discoscopy to inspect the accessed discs, discectomies and/or disc augmentation/replacement and/or vertebroplasty, balloon-assisted vertebroplasty, fusion, alignment, drug delivery, electrical stimulation, or other therapies, is enabled by the provision of the percutaneous pathway and formation of the anterior or posterior TASIF bore(s).

The bore forming tool sets comprise elongated drill shaft assemblies supporting distal boring tools, e.g., mechanical rotating drill bits, burrs, augurs, abraders, or the like (collectively referred to as boring heads or drill bits for convenience), that can be manipulated in use to bore a straight or curved axial bore. Suitable bore forming tools are disclosed in the above-referenced provisional application No. 60/182,748 and the '105 application. However, the TASIF axial bores can be formed by other tools that mechanically puncture or penetrate vetebral bodies and intervertebral discs or otherwise form TASIF axial bores in any diameter or cross-section and that follow any alignment with the axis of the spine as visualized by the AAIFL or PAIFL. For convenience, the posterior and anterior TASIF axial bores are referred to as being formed or bored herein.

Posterior TASIF Axial Bore Formation:

FIGS. 7 and 8 illustrate step S100 for forming the posterior percutaneous tract and the posterior TASIF axial bore 22 formed in step S200 and extending through sacral and lumbar vertebrae and intervening discs axially aligned with the visualized PAIFL of FIGS. 1 and 2 using a boring tool of the type described in more detail in the above-referenced '105 and '748 applications. The same steps can be employed to form a pilot hole of step S100 that can be enlarged in step S200. In this case, a small diameter bore forming tool (e.g. 3.0 mm diameter) is used to first bore a small diameter curved pilot hole following the imaginary, visualized PAIFL 20 through S1, L5 and L4 in step S100. Then, the boring tool is removed, and a guidewire having a threaded distal screw-in tip is advanced through the pilot hole and screwed into to the caudal end of the pilot hole and into cephalad portion of the L4 body. An over-the-wire bore enlarging tool having a flexible body capable of tracking the curved guidewire is fitted over the proximal end of the guidewire and manually or mechanically rotated and advanced along it in step S200. In this way, the small pilot hole diameter is enlarged to form the anterior TASIF axial bore 22 having a diameter e.g. a 10.0 mm diameter, and the enlarging tool is then removed.

It will be understood that the illustrated diameter of the posterior TASIF axial bore hole 22 relative to sizes of the vertebral bodies is merely exemplary, and that it is contemplated that the pilot hole and bore hole diameters can range from about 1-10 mm and 3-30 mm, respectively. Moreover, it will be understood that a plurality of such posterior TASIF axial bores $22_1 \ldots 22_n$ can be formed in side by side or diverging relation generally aligned with the PAIFL.

In FIG. 7, the posterior surface of the sacrum is exposed in step S100 as described in the above-referenced '222 and '748 applications. The area of the patient's skin surrounding the incision site is surgically prepped, and the anus is excluded from the surgical field using adhesive drapes. The actual dermal entry site may be determined by the prone, preoperative CT scan or magnetic resonance imaging (MRI) study that maps the PAIFL. In step S100, an incision is made in the patient's skin over the posterior sacral surface of S2, and the subcutaneous tissue is separated to expose the posteriorly extending, bony ridge of the posterior sacral surface. A small laminectomy 14 is performed through the posterior ridge of the sacrum inferior. The thecal sac and nerve roots that are exposed by the laminectomy are gently retracted, and the terminal portion of the spinal canal is exposed.

An elongated drill shaft assembly (not shown) is axially aligned with the PAIFL at the posterior target point so that the initial penetration of the sacrum is substantially at right angles to the exposed sacral surface. A drill guide for receiving the drill drive shaft assembly for drilling or boring a posterior TASIF axial bore 22 from S2 along the visualized PAIFL may optionally be attached to S2 and extended posteriorly through the exposed spinal canal and skin incision.

The progress of the drill bit is observed using conventional imaging equipment. As the elongated drill shaft assembly is extended anteriorly in the cephalad direction, a curvature is introduced in the cephalad segment of the posterior TASIF axial bore 22 as shown in FIG. 8. It is necessary to maintain the plane of curvature of the distal segment aligned to the curvature of the spine. In this way, the drill bit advances through the sacral vertebrae in the cephalad direction and toward the lumbar vertebral bodies while staying within the spongy, cancellous bone of each vertebral body. Theoretically, any number of vertebral bodies of the spine can be bored through in the cephalad axial direction. The cephalad end of the posterior TASIF axial bore 22 can terminate within a vertebral body or within a disc or disc space.

Figure 9:
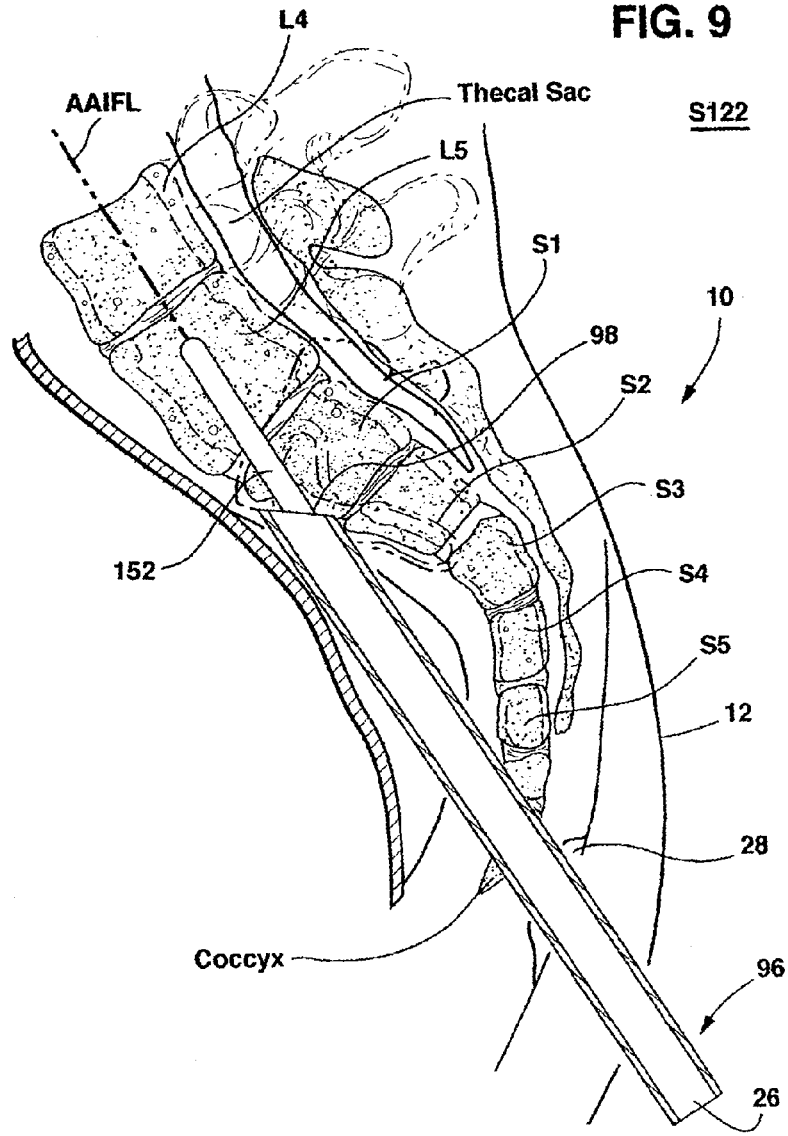
FIG. 9 illustrates, in a partial cross-section side view, one manner of obtaining access to an anterior target point for forming an anterior TASIF axial bore through sacral and lumbar vertebrae and intervening discs axially aligned with the visualized AAIFL of FIGS. 1 and 2.
Figure 10:
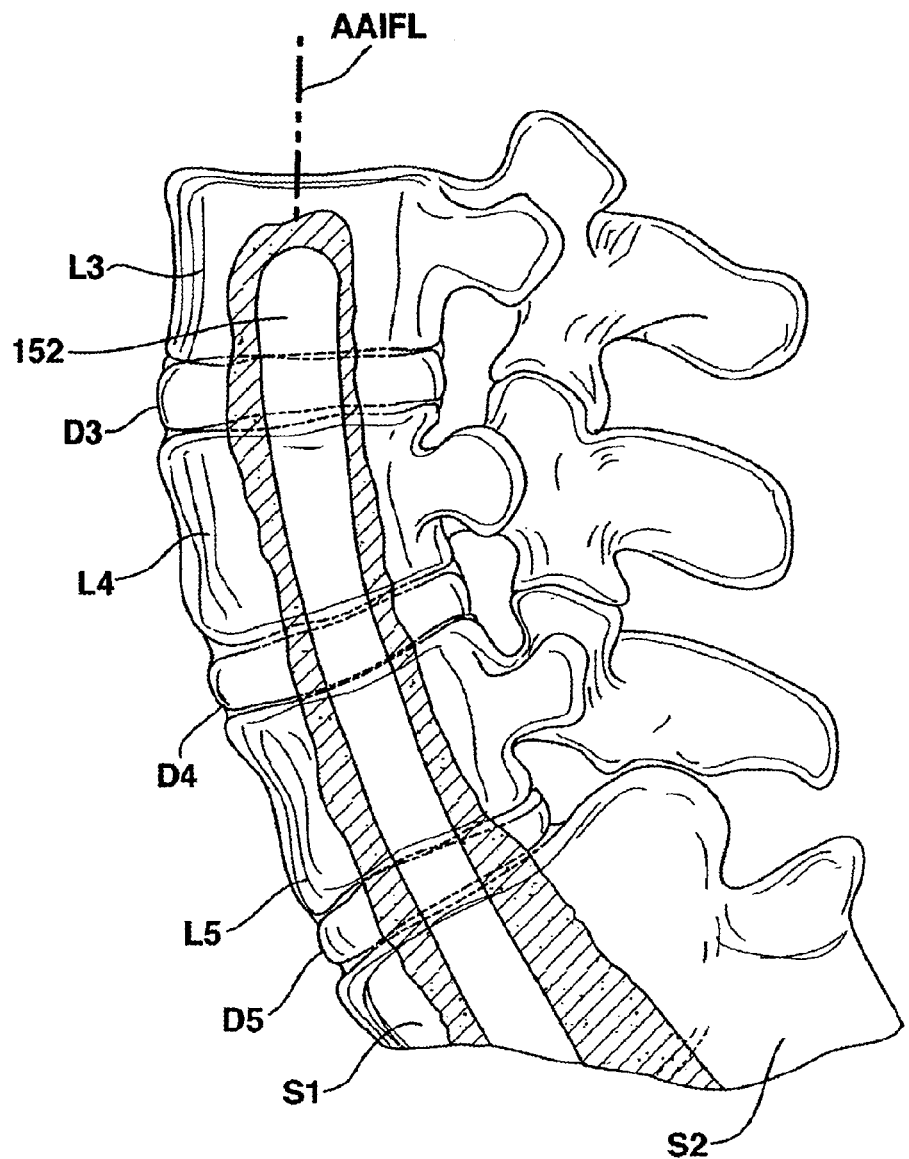
FIG. 10 is an enlarged partial cross-section view illustrating an anterior TASIF axial bore through sacral and lumbar vertebrae and intervening discs axially aligned with the visualized AAIFL of FIGS. 1 and 2.

Anterior TASIF Axial Bore Formation:

FIGS. 9 and 10 illustrate the anterior percutaneous tract formed in step S100 and the anterior TASIF axial bore 22 formed in step S200 and extending through sacral and lumbar vertebrae and intervening discs axially aligned with the visualized AAIFL of FIGS. 1 and 2 using a boring tool of the type described in more detail in the above-referenced '105 and '748 applications. The same steps can be employed to form a pilot hole of step S100 that can be enlarged in step S200 as described above. It will be understood that the illustrated diameter of the anterior TASIF axial bore hole 152 relative to sizes of the vertebral bodies is merely exemplary, and that it is contemplated that the pilot holes and bore hole diameters can range from about 1-10 mm and 3-30 mm, respectively. Moreover, it will be understood that a plurality of such anterior TASIF axial bores $152_1 \ldots 152_n$ can be formed in side by side or diverging relation generally aligned with the AAIFL.

The anterior TASIF axial bore(s) can be relatively straight from the anterior target point into or through at least the caudal lumbar vertebrae and intervertebral discs. But, it may be desirable or necessary to form a curved anterior TASIF axial bore(s) particularly as the bore(s) is extended in the cephalad direction to maintain the plane of curvature of the cephalad segment of the TASIF axial bore(s) aligned to the curvature of the spine. In this way, the drill bit advances through the sacral vertebrae in the cephalad direction while staying within the spongy, cancellous bone of each vertebral body. Theoretically, any number of vertebral bodies of the spine can be bored through in the cephalad direction. The cephalad end of the posterior TASIF axial bore(s) 152 can terminate within a vertebral body or within a disc or disc space.

Diver in TASIF Axial Bores:

If a single anterior or posterior TASIF axial bore is to be made, it preferably is axially aligned with the respective visualized AAIFL or PAIFL as shown by TASIF axial bores 22 or 152 shown in FIG. 4. Plural anterior or posterior TASIF bores $22_1 \ldots 22_n$, or $152_1 \ldots 152_n$ shown in FIG. 5 are in parallel or diverging alignment with the visualized AAIFL and PAIFL. Multiple anterior or posterior TASIF axial bores can be formed all commencing at an anterior or posterior target point of FIGS. 1-3 and extending in the cephalad direction with each TASIF axial bore diverging apart from the other and away from the visualized axial AAIFL and PAIFL. The diverging TASIF axial bores terminate as spaced apart locations in a cephalad vertebral body or in separate cephalad vertebral bodies or spinal discs.

Figure 11:
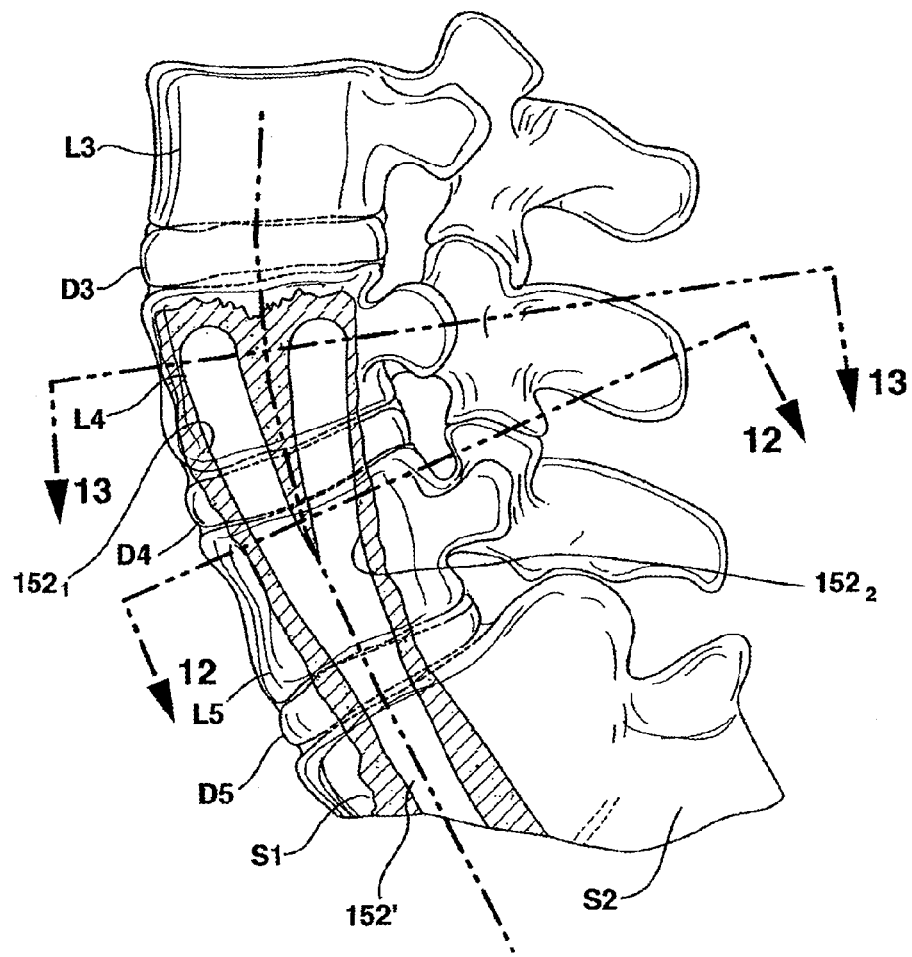
FIG. 11 depicts, in a partial cross-section side view, the formation of a plurality of curved TASIF axial bores that diverge apart from a common caudal section in the cephalad direction.
Figure 12:
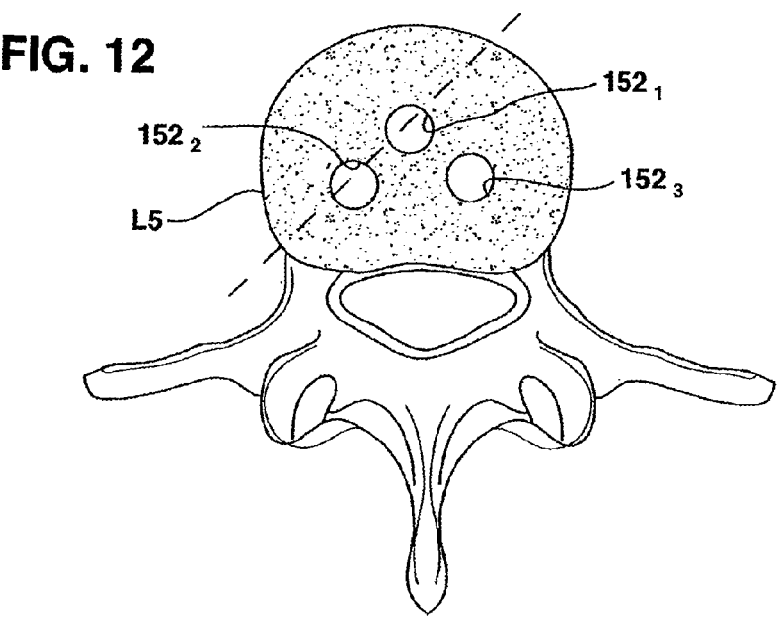
FIGS. 12 and 13 depict, in partial cross-section end views taken along lines 12-12 and 13-13, respectively, of FIG. 7, the divergence of the plurality of curved TASIF axial bores.
Figure 13:
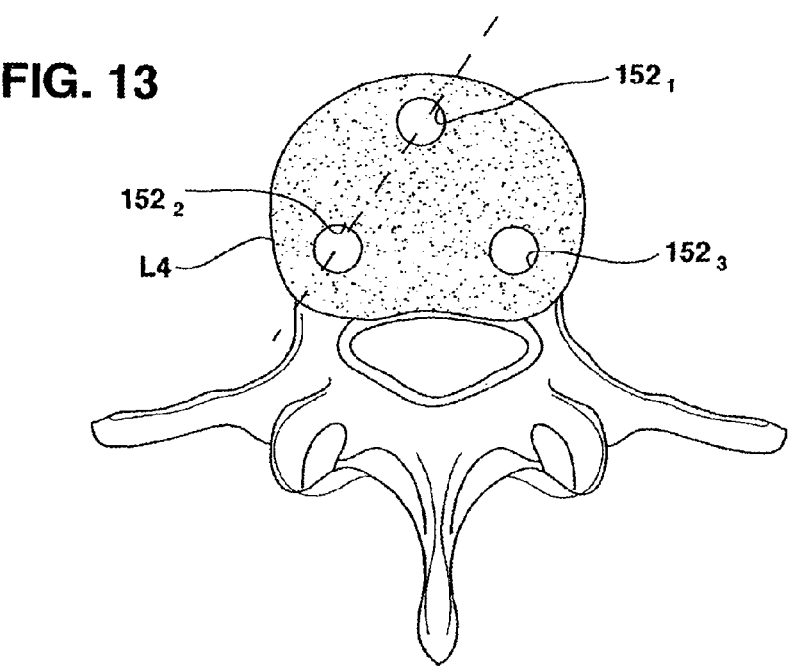

For example, FIGS. 11-13 depict a group of three anterior TASIF axial bores $152_1$, $152_2$, $152_3$ that are bored from a common caudal entrance bore section 152' starting at the anterior target point. The three anterior TASIF axial bores $152_1$, $152_2$, $152_3$ extend in the cephalad direction generally following the curvature of the AAIFL but diverging outwardly to form a "tripod" of the diverging TASIF axial bores $152_1$, $152_2$, $152_3$. The divergence from the common entry bore section can start in the sacral vertebra or in L5 or in L4 or in any other cephalad vertebral body that the bore extends into or through. The common caudal entrance bore section 152' through S1, and traversing disc D5 and part of L4 can be larger in diameter than the diverging TASIF axial bores $152_1$, $152_2$, $152_3$ to accommodate the insertion of three elongated axial spinal implants therein or to facilitate performing a therapy as described further below. It is believed that the insertion of elongated axial spinal implants within the "tripod" of the diverging TASIF axial bores $152_1$, $152_2$, $152_3$ can substantially strengthen and enhance fusion of L4, L5 and S1. The diverging TASIF axial bores $152_1$, $152_2$, $152_3$ can be extended further than shown in FIGS. 11-13. Diverging posterior TASIF axial bores can be formed in the same manner.

Therapeutic Procedures:

In accordance with the present invention, a variety of therapeutic procedures can be performed in step S300 or step S400 after the curved posterior or curved or straight anterior TASIF axial bore(s) is formed employing instruments, axial spinal implants, spinal disc implants and materials. Certain of the therapies or therapeutic procedures can be completed in step S300 without an axial spinal implant also being implanted in step S400. Step S400 may also be performed in certain cases without a therapeutic procedure being performed in step S300. The therapeutic procedures that are performed using such instruments, axial spinal implants, spinal disc implants and materials of the present invention comprise one or more of: (1) performing a discoscopy by inserting an endoscope and inspecting the condition of the vertebral bodies and spinal discs; (2) performing a simple fusion by inserting bone growth materials into the TASIF axial bore(s) in step S400; (3) performing a partial discectomy or complete discectomy of a disc accessed through a TASIF axial bore in step S300; (4) performing a vertebroplasty or balloon-assisted vertebroplasty to a fractured vertebral body accessed through a TASIF axial bore in step S300; (5) inserting an artificial disc implant or autologous/homologous bone or bone growth material into the disc space following a complete discectomy of a disc accessed through a TASIF axial bore in step S400 to encourage fusion or to function as a functional disc replacement; (6) following a partial discectomy removing at least a portion of the nucleus, inserting an inflatable envelope or other disc implant or a material into the disc space to augment a disc accessed through a TASIF axial bore in step S300 to encourage fusion or to function as a functional disc replacement; (7) inserting axial spinal implants into the bore(s) as a single therapy or in conjunction with any of the preceding listed therapies (1)-(6) in step S400; (8) inserting axial spinal implants providing distraction of two or more vertebrae across one or more intervertebral disc and/or shock absorption due to loads applied axially to the spine in step S400; (9) extending an electrical lead from an implanted or external electrical stimulator through a TASIF axial bore to locate one or more electrical stimulation electrode of the lead or incorporated with an elongated axial spinal implant or spinal disc implant within or between adjoining vertebral bodies to apply electrical stimulation to encourage bone growth or to counter pain in step S300; (10) extending a catheter from an implanted or external drug dispenser through a TASIF axial bore to a drug delivery port of the catheter or incorporated with an elongated axial spinal implant or spinal disc implant to dispense a drug within or between adjoining vertebral bodies or outside vertebral bodies to encourage bone growth or to counter pain in step S300; and (11) performing a brachytherapy of a vertebral body through an axial bore to treat metastatic disease in the spine or adenopathy in the retroperitoneum. The TASIF axial bore openings at the anterior or posterior sacral positions are preferably backfilled, plugged or closed following each such therapeutic procedure with a bone growth material or bone cement.

For convenience of illustration, the therapeutic procedures are illustrated in the drawings and described as follows as being performed through an anterior percutaneous tract formed using an anterior tract sheath 96 and TASIF axial bore 152. But, it will be understood that the procedures may be performed through a posterior percutaneous tract and TASIF axial bore 22 and that certain of the procedures may be advantageously performed using parallel or diverging TASIF axial bores.

In each of the following procedures to deliver a therapy, the anterior TASIF axial bore 152 is formed, as described above, through the use of anterior tract sheath 96 that inserted earlier through the presacral space 24 from a skin incision 28 to the anterior target point of the anterior surface of sacral vertebra S1 that defines the percutaneous tract 26. The shaped end 98 of the anterior tract sheath 96 is aligned with the anterior surface of the sacral vertebra S1 during step S100. The shaped end 98 may be formed with attachment teeth or threads to fix it to the sacral bone. It will be understood that the therapeutic procedures of the present invention may be performed through the lumen of such a tract sheath 96 or simply through a defined anterior tract 26 extending through the pre-sacral space 24 to axially access the vertebrae.

It will be understood that each of the following therapies to the spinal discs or the vertebral bodies can be conducted on more than one spinal disc or vertebral body or on one or more spinal disc and one or more vertebral body traversed by at least one TASIF axial bore. For example, two spinal discs may be accessed by a single TASIF axial bore, and treated in one of the following ways, starting with the cephalad spinal disc. Then, the portion of the TASIF axial bore between the cephalad and caudal spinal disc is closed by an artificial axial spinal implant or bone growth material as appropriate. The caudal spinal disc is then treated, and the portion of the TASIF axial bore between the caudal spinal disc and the anterior or posterior sacral bore entry point is closed by an artificial axial spinal implant or bone growth material as appropriate. Similarly, cephalad and caudal vertebral bodies may be treated by vertebroplasty or balloon-assisted vertebroplasty, and the intervertebral disc may also be treated by one of the following described therapies. For convenience, the treatment of only a single spinal disc or vertebral body is described and illustrated in the drawings.

Thus, the following therapeutic procedures of the present invention are understood to involve accessing an anterior or posterior sacral position of a sacral vertebra in alignment with the visualized, AAIFL or PAIFL extending in said axial aspect cephalad through a series of adjacent vertebral bodies of adjacent vertebrae. Then, from the accessed anterior sacral position, at least one anterior or posterior TASIF axial bore is bored in alignment (as defined herein) with the AAIFL or PAIFL axially through at least the caudal sacral vertebra and through or into one or more cephalad vertebral bodies of the series of adjacent vertebral bodies and any interposed, intervertebral, spinal discs. The delivery of the therapies is followed by the withdrawal of any tract forming tools and a simple surgical closure of the incision site. The therapies can be delivered or therapeutic procedures can be performed as follows.

Simple Fusion:

The prior art provides no convenient and relatively atraumatic way to promote fusion between adjacent vertebral bodies where the intervertebral disc has degenerated. One therapeutic procedure of the present invention simply involves filling the anterior or posterior TASIF axial bore(s) with a bone growth material which bridges the spinal disc and will effect bone growth across the spinal disc. The cancellous bone is typically porous with fissures and cavities, so that the bone growth material is also forced into such cancellous bone cavities and fissures. In this embodiment, it may be desirable to bore and fill a plurality of parallel or diverging anterior or posterior TASIF axial bores to provide a number of bridges of bone growth material through the intervertebral spinal disc.

For purposes of this therapy and other fusion therapies described herein, a "bone growth material" can be one or more of the following, or any other biocompatible material judged to have the desired physiologic response, including any natural or artificial osteoconductive, osteoinductive, osteogenic, or other fusion encouraging material. Particularly, morselized cortical, cancellous, or cortico-cancellous bone graft, including autograft, allograft, or xenograft might be employed. Or any bone graft substitute or combination of bone graft substitutes, or combinations of bone graft and bone graft substitutes, or bone inducing substances, could be employed. Such bone graft substitutes or bone inducing substances include, but not limited to, hydroxyapatite, hydroxyapatite tricalcium phosphate; bone morphogenic protein (BMP) and calcified or decalcified bone derivative and resorbable bone cements. The resorbable cement material can be a calcium derivative generally composed of hydroxyapatite, orthophosphoric acid, calcium carbonate, and calcium hydroxide formed into a semi-liquid paste with an alkaline solution of sodium hydroxide and water or a composition comprising polypropylene fumarate or a mixture of calcium phosphates. Other compositions that may be employed comprise calcium salt filler, N-vinyl-2-pyrrolidone, and a peroxide or free radical initiator. The bone graft material may be mixed with a radiographic material to enable its visualization during delivery to assure proper disposition and filling of bores, cavities and spaces described herein.

In certain cases, e.g. correcting spondylolisthesis, it is necessary to realign the vertebral bodies before boring the anterior or posterior TASIF axial bore(s) and to reinforce or stabilize the vertebrae pending fusion. In this case, and in other cases where reinforcement is deemed necessary, a pre-formed elongated axial spinal implant can be inserted into at least one of the anterior or posterior TASIF axial bore(s) along with bone growth material. The axial spinal implant can be a surface roughened metal rod or porous tube of the type described in the above-referenced '620 application that is configured to the particular bore curvature and size and surface treated bite into vertebral bone and to promote bone ingrowth.

This therapy provides a simple and relatively atraumatic approach to the vertebrae of interest where there is no need to treat or remove the intervertebral disc. Fusion may be effected in other ways described as follows using the bone growth materials and optionally using an elongated axial spinal implant.

Complete Discectomy:

As described above, the complete discectomy procedures conducted in the past have been done through lateral exposure of the disc that presents a number of problems that are eliminated by the present invention.

Figure 14:
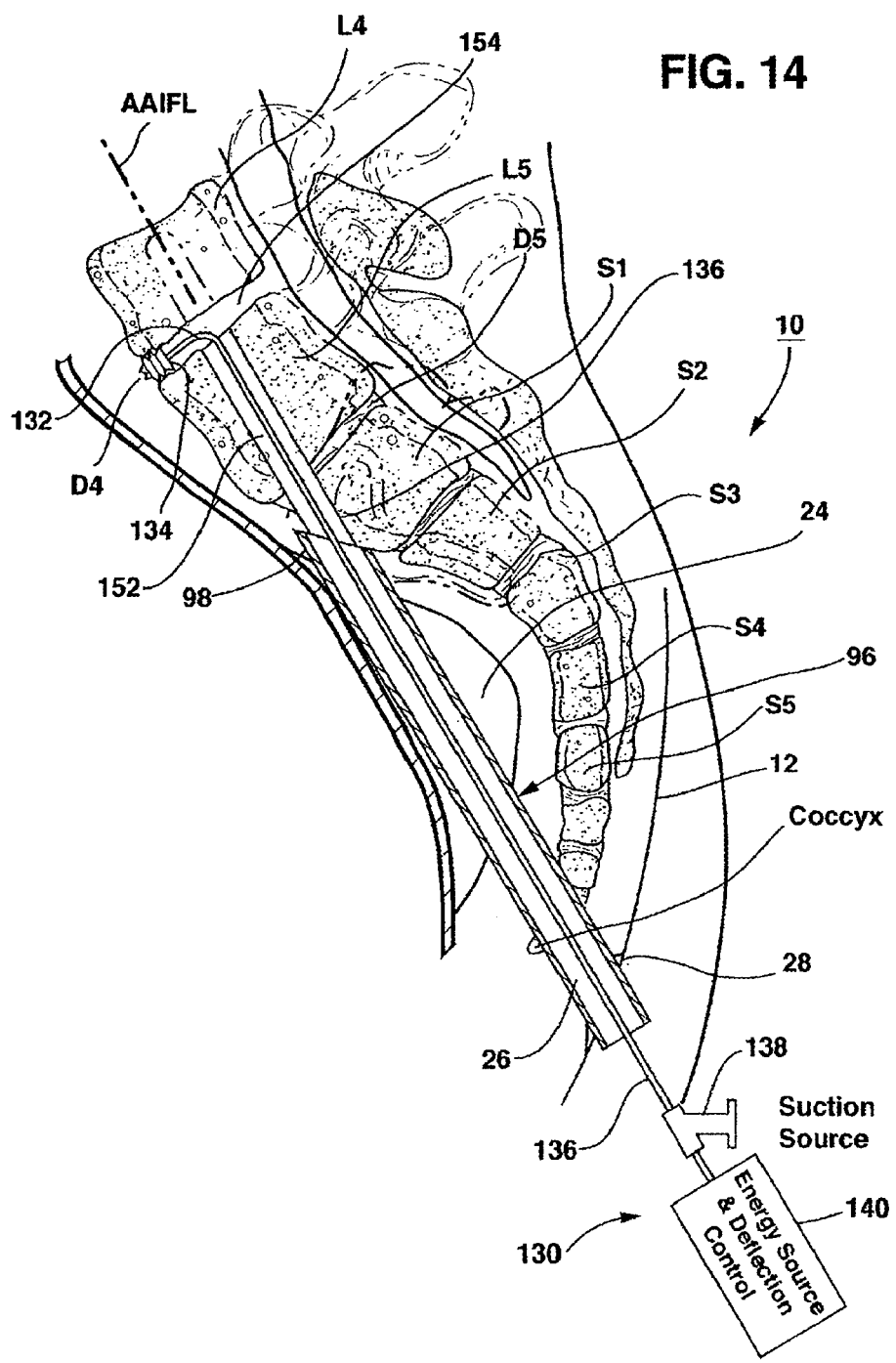
FIG. 14 illustrates, in a partial cross-section side view, one manner of performing a complete discectomy of a disc effected through a TASIF axial bore to enable insertion of bone growth materials for fusion of the vertebral bodies or a pre-formed disc implant or for performance of other therapies to the spinal column and nerves.

FIG. 14 illustrates, in a partial cross-section side view, one manner of performing a complete discectomy of a spinal disc, e.g., D4, effected through a TASIF axial bore 152 to enable fusion of the vertebral body endplates of lumbar vertebrae L4 and L5 directly together or to provide a disc space for receipt of a pre-formed artificial disc implant that mimics the function of a patent spinal disc. The complete discectomy procedure involves more or less complete excision of the intervertebral disc D4 including the nucleus, the annulus, the cartilaginous endplates adhered to the opposed cortical bone endplates of the cephalad and caudal vertebral bodies, and, optionally, the vertebral periosteum, cortical endplate bone and cancellous bone to a desired depth and shape. Distraction is applied to the lumbar vertebrae L4 and L5 by suitably supporting the patient's body to maintain the disc space for fusion and/or implantation of an artificial disc implant. The excised materials are withdrawn from the disc space and the fusion materials or artificial disc implant is introduced to the disc space through the TASIF axial bore 152.

The TASIF axial bore 152 either terminates within the spinal disc to be removed or extends into a vertebral body cephalad to that spinal disc in the event that an axial spinal implant or bone growth material is to be inserted into the TASIF axial bore bridging the excised disc space. FIG. 14 depicts the TASIF axial bore 152 in solid lines terminating in the disc D4 and in broken lines extending into vertebral body L4.

Then, a discectomy tool 130 is inserted through the axially aligned anterior tract 26 defined by the lumen of the anterior tract sheath 96. The discectomy tool 130 is formed like a flexible atherectomy catheter for fragmenting and removing obstructions in blood vessels using a cutting head 134 to fragment the disc material and to scrape away cortical and cancellous bone and aspiration with saline flushing to remove the fragments from the disc space. The cutting head 134 is mounted into a deflectable or steerable distal end section 132 of discectomy tool shaft 136 extending through the TASIF axial bore 152 and anterior tract 26 from an externally disposed energy source and deflection control 140. The distal end section may be angularly deflected using a deflection mechanism, e.g., a pull wire within a pull wire lumen of the elongated, flexible, discectomy tool shaft 136 and a proximal pull wire control of the proximal guiding and cutting mechanism 140 coupled thereto. The cutting head 134 may be pulled back and forth laterally and/or swept in a 360° arc about the axial bore 152 to traverse and excise selected symptomatic portions of or the entire spinal disc D4 and to cut away layers of bone from the endplates of vertebral bodies L4 and L5 by manipulation of the proximal end portion of the discectomy tool shaft 136 extending from the skin incision 28.

The complete discectomy cutting head 134 and tool shaft 136 are shown schematically and not necessarily to scale to one another or to the TASIF axial bore 152.

The cutting head 134 may comprise any of the known types, e.g. mechanical cutters including rotating wire brushes, cutting blades, scissors, screws, bits, extendable/retractable rotating wires, or the like, or energy application heads, e.g., resistive heating, laser energy or ultrasonic energy heads, or fluid jets or the like. The bore expanding cutting tools disclosed in the above-referenced '369 application could also be modified to reach the disc annulus and excise it. Various forms of cutting heads are disclosed in the above-referenced '146, '962 and '629 patents and in further U.S. Pat. Nos. 6,095,149, 6,127,597, 5,383,884, and RE 33,258, for example. However, the tool shafts of the prior art discectomy tools are designed for the lateral access into the spinal disc and are not disclosed as being introduced axially and then into the space between the vertebral body endplates.

The cutting head 134 in this example is a mechanical screw thread that can be selectively covered in whole or part by a sheath (not shown) for exposing the end or a lateral portion of the cutting screw thread in the manner of the augur disclosed in the above-referenced '884 patent for example. The cutting head 134 is attached to a drive shaft extending through a drive shaft lumen of the tool shaft 136 to a drive motor for rotating the drive shaft and cutting head 134 and a deflection control for operating the pull wire or the like for deflecting the distal section 132, both included in energy source and deflection control 140. Preferably an aspiration lumen is included within the discectomy tool body 136 with a distal opening adjacent to the cutting head 134 and terminating proximally at a side suction port 138 adapted to be coupled to a source of suction to aspirate the fragments of the disc from disc space 154. A saline flush lumen and supply can also be incorporated within to flush blood and excised fragments for aspiration.

The operation and movement of the cutting head about the spinal disc D4 is preferably observed employing fluoroscopy or other radiographic visualization techniques. An endoscopic visualization or the disc space 154 could also be employed using a separate or incorporated deflectable tip endoscope for illumination and observation of the site.

The resulting disc space 154 can either be substantially disc-shaped with more or less planar opposed sides having a height in the range of about 8 mm to about 14 mm, a lateral width of from about 26 mm to about 32 mm, and an anterior-posterior width of from about 22 mm to about 30 mm. However, the disc space 154 can be selectively enlarged into a convex disc shape extending caudally into the cancellous bone of caudal vertebral body L5 and/or in the cephalad direction into the cancellous bone of cephalad vertebral body L4. This disc space shaping forms a pocket that helps to confine a spinal disc implant inserted into the prepared disc space 154 or bone growth materials dispensed into the prepared disc space 154.

A fusion of vertebral bodies D4 and D5 or the implantation of an artificial spinal disc into the disc space 154 through the anterior TASIF axial bore 152 and percutaneous tract 26 may be undertaken after the disc space is cleared of debris.

Moreover, the TASIF axial bore can be filled with an axial spinal implant that provides internal stabilization, alignment, and reinforcement of the spinal motion segment. This therapeutic procedure of the present invention can be advantageously conducted without any injury to any ligaments, muscles and facet joints of the spinal motion segment.

Fusion Across Excised Disc Space:

As described above, the complete and partial discectomy procedures followed by introduction of fusion materials and devices conducted in the past have been done through lateral exposure of the disc that presents a number of problems that are eliminated by the present invention.

Figure 15:
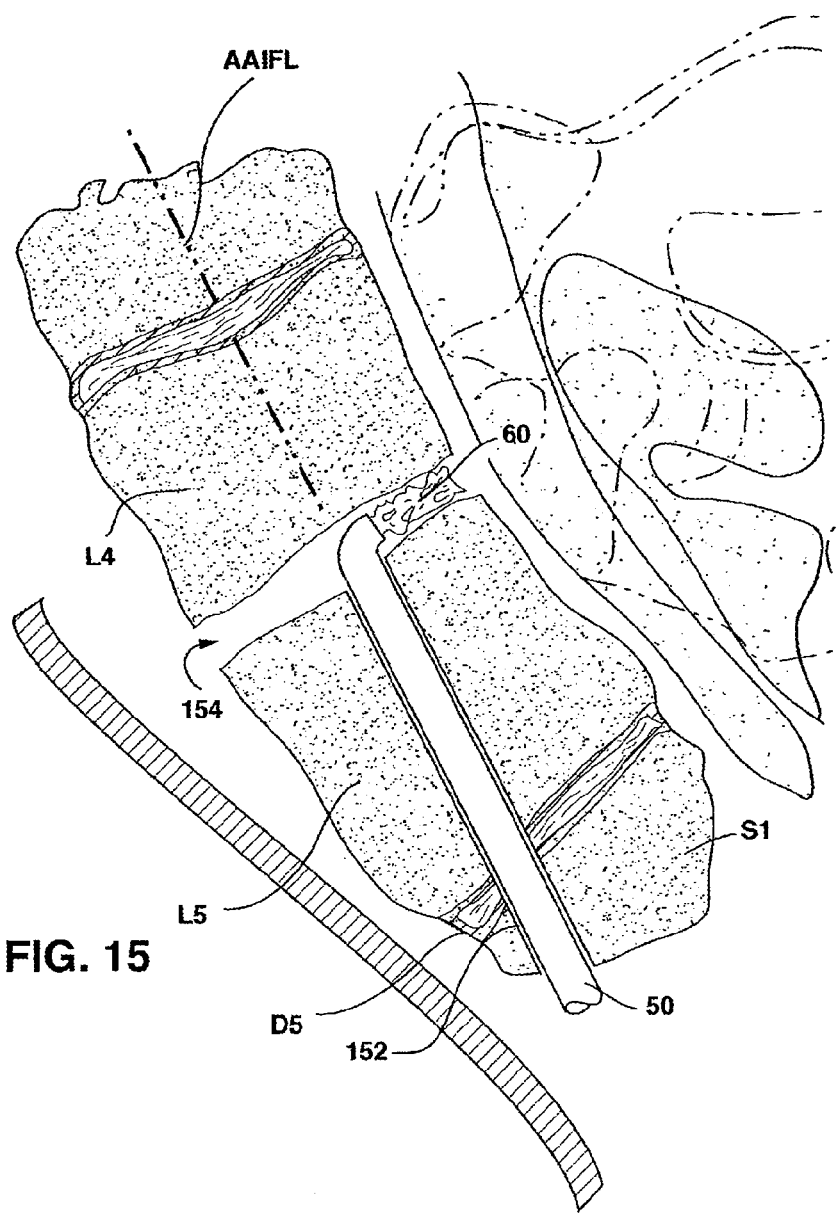
FIG. 15 illustrates, in a partial cross-section side view, one manner of filling a disc space formed by a complete discectomy with bone growth materials to effect fusion.

In its simplest form of this aspect of the present invention, fusion of the prepared endplates of L4 and L5 can be effected by pumping a bone growth material slurry into the disc space 154 through the TASIF axial bore 152 and percutaneous tract 26 as shown in FIG. 15. A catheter 50 having a straight or flexible tip section as shown can be employed that is extended through the axially aligned anterior tract 26 and the TASIF axial bore 152 to dispense the bone growth material 60 in the disc space 154. A plunger can also be employed that is extended through the axially aligned anterior tract 26 and the TASIF axial bore 152 to pack the dispensed material from the TASIF axial bore 152 into the disc space 154. Then, the caudal end opening or the full length of the TASIF axial bore 152 is plugged with an artificial plug or bone growth material, and the sheath 96 is withdrawn. The incision 28 is closed and the patient rests for a time until bone growth takes place.

This procedure illustrated in FIG. 15 may suffer from the inability to adequately fill the disc space 154 or to confine the dispensed bone growth material within the disc space during the procedure and may require prolonged bed rest recuperation to avoid later settling and ejection of the bone growth material.

Figure 16:
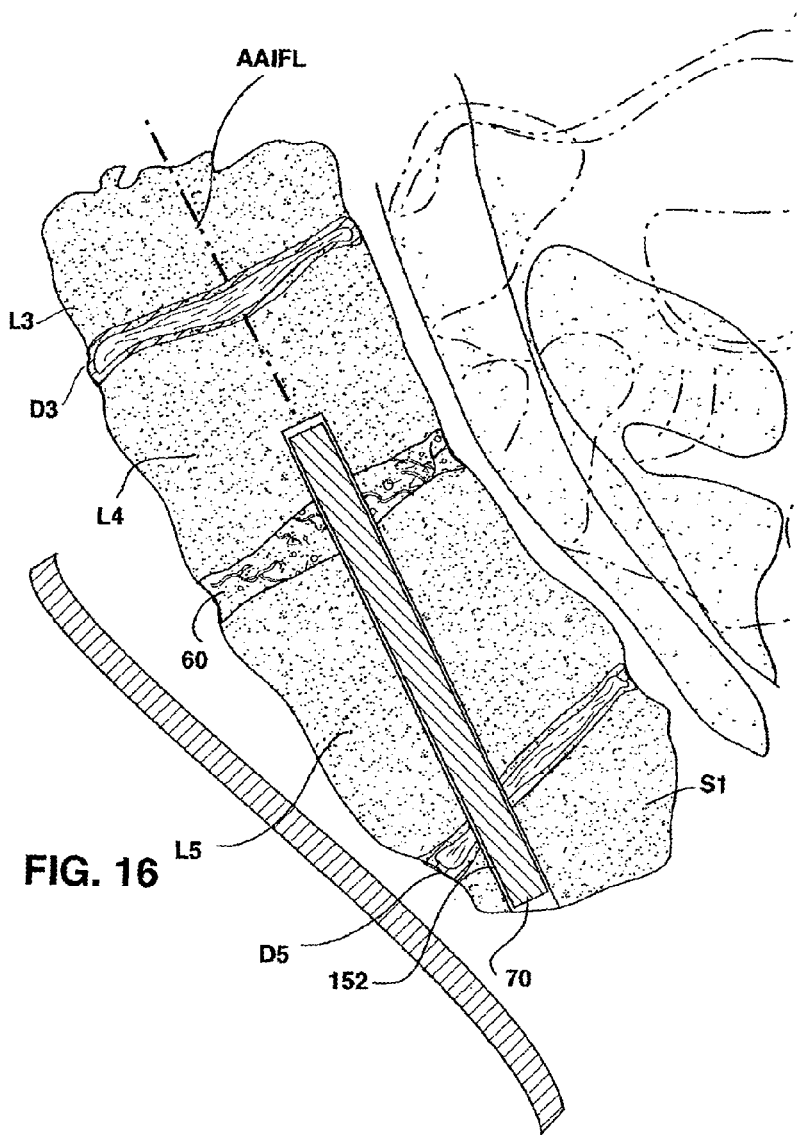
FIG. 16 illustrates, in a partial cross-section side view, one manner of strengthening the fusion of the vertebral bodies by implantation of an elongated axial spinal implant into the TASIF axial bore bridging the filled disc space.

A pre-formed, rod shaped, artificial axial spinal implant 70 can be inserted into the TASIF axial bore 152 to fill all or part of it in order to help maintain the distraction of the vertebral bodies as shown in FIG. 16. The pre-formed axial spinal implant 70 can extend into the cephalad vertebral body L4 if the TASIF axial bore 154 extends into it as shown in FIG. 16 and may include the distraction and shock absorbing characteristics of the particular axial spinal implants described below. In this case, it may be desirable to form parallel or diverging TASIF axial bores and implant an axial spinal implant in each bore. The pre-formed, rod shaped, artificial axial spinal implant 70 may employ a fixation mechanism and/or be fixed in place using one of the above described bone growth materials.

Figure 17:
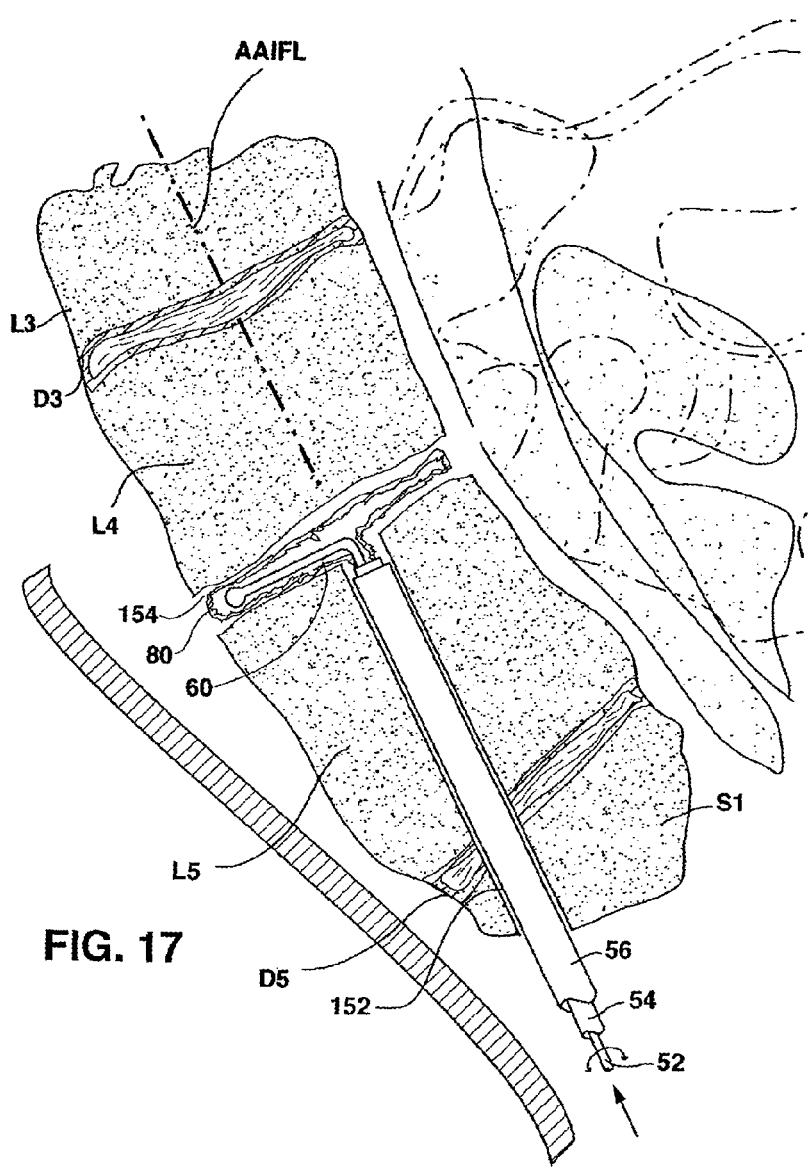
FIG. 17 illustrates, in a partial cross-section side view, one manner of implanting a spinal disc implant following complete discectomy of a disc effected through the delivery of a porous envelope in a deflated condition through a TASIF axial bore and into the disc space.

Alternatively, fusion of the vertebral bodies can be effected according to a further aspect of the present invention using spinal disc implants that are dispensed into the disc space through the TASIF axial bore 152 and percutaneous tract 26 and maintained there in a variety of ways. One approach, shown in FIG. 17, is to dispense a porous, deflated, shaped bag or balloon or sack or other envelope 80 of a type described in the above-referenced '679 patent into the disc space 154 formed in FIG. 14 and to then fill and inflate the envelope 80 with a bone growth material 60 of one of the types described above as shown in FIG. 18, and to close the opening into the envelope 80. The porous fabric has pores that are small enough to confine the bone growth material within the envelope while allowing passage of fluids and bone growth therethrough. The envelope 80 could be formed of a tightly woven, high molecular weight, high tenacity, flexible polymeric fabric e.g., high molecular weight polyethylene, polyester, polyolefine, polyethylene terephthalate, polytetrafluoroethylene, polysulfone, nylons, or any other high molecular weight, and other high tenacity materials including carbon fiber yarns, ceramic fibers, metallic fibers, etc.

The envelope 80 can be inserted into the prepared disc space 154 in a variety of ways, one of which is shown in FIG. 17. The envelope 80 is folded against a blunt tip flexible push wire 52 which extends through the lumen of a fill tube 54 that extends into the balloon opening. The folded envelope 80, push wire 52 and fill tube 54 are in turn inserted into the lumen of a tubular catheter or sheath 56 that is advanced through the percutaneous tract 26 and TASIF axial bore 152. Then, the envelope 80 is advanced into the prepared, distracted disc space 154 and spread out by pushing and torqueing the push wire 52. Air or liquid inflation of the shaped envelope 80 can also be used to spread the envelope out in the disc space instead of the push wire 52.

Figure 18:
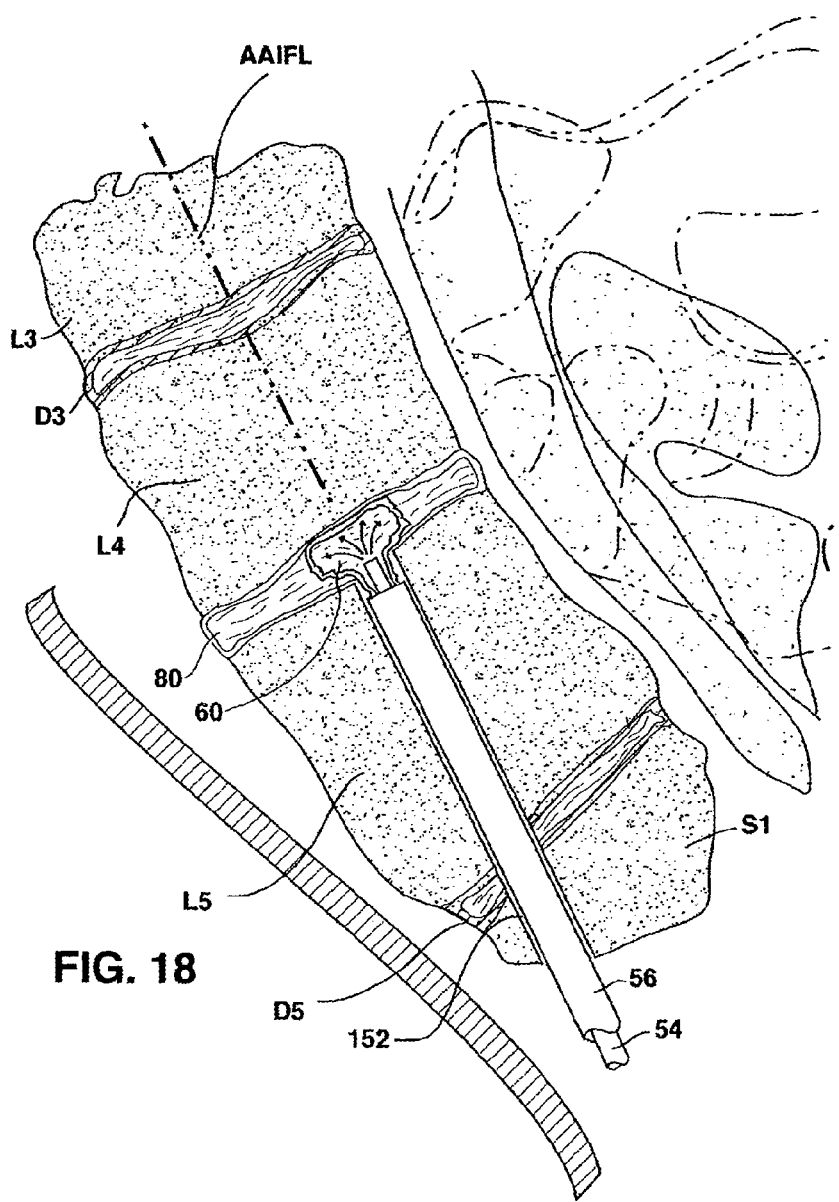
FIG. 18 illustrates the filling of the porous envelope of FIG. 16 with a material selected from bone growth materials for fusion or other biomaterials forming an artificial spinal disc implant.

The push wire 52 is withdrawn, air is evacuated from the envelope interior trough the lumen of the fill tube 54, and bone growth material 60 is then injected through the lumen of the fill tube 54 as shown in FIG. 18. The filled envelope 80 conforms with the prepared disc space 154, and the dispensed bone growth material 60 is confined therein to maintain the spacing between the vertebral body end plates when the envelope opening is closed. The envelope opening can be closed by drawing a purse-string suture sewn around the opening tight and tying it through the TASIF axial bore 152 and percutaneous tract 26 or in other manners described in the above-referenced '679 and '736 patents and in U.S. Pat. No. 5,702,454. The bone growth material confined within the envelope 80 maintains the distraction spacing between the prepared vertebral body endplates.

One manner of maintaining the filled envelope 80 in place would be to advance an elongated axial spinal implant 70 in the caudal direction into the opening of the filled envelope 80 to abut a section of the envelope fabric against the cephalad vertebral endplate, thereby both sealing the envelope opening and locking it into place.

Another way to maintain the filled envelope 80 in place would be to form the disc space 154 with concave, prepared vertebral body endplates during the complete discectomy and to form the envelope 80 with convex sides that fit within the concave surfaces when the envelope 80 is filled with bone growth material.

Figure 19:
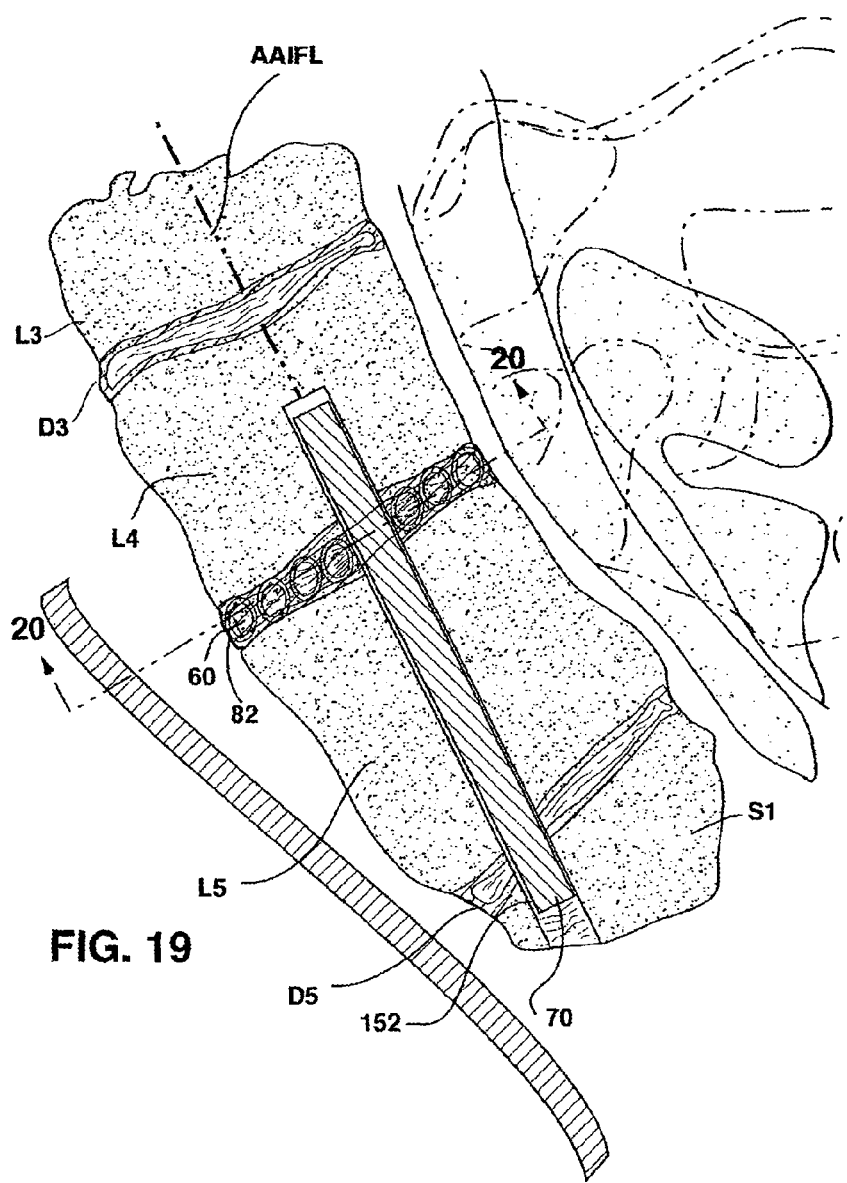
FIG. 19 illustrates, in a partial cross-section side view, an alternative planar spiral configuration of a spinal disc implant delivered through a TASIF axial bore into the disc space and the retention of the spinal disc implant by implantation of an elongated axial spinal implant into the TASIF axial bore bridging the filled disc space.

A further manner of keeping the filled envelope 80 in place is to form it to expand upon filling with bone growth material into a toroidal or tire shape providing a hole aligned with the TASIF axial bore 152 that an elongated axial spinal implant 70 can be fitted through. Or the envelope can be formed as an elongated tube 82 that is shaped to assume a toroidal member shape or a spiral member shape having a number of spiral turns in a common plane upon filling and inflation with bone growth material as shown in FIGS. 19 and 20.

Figure 20:
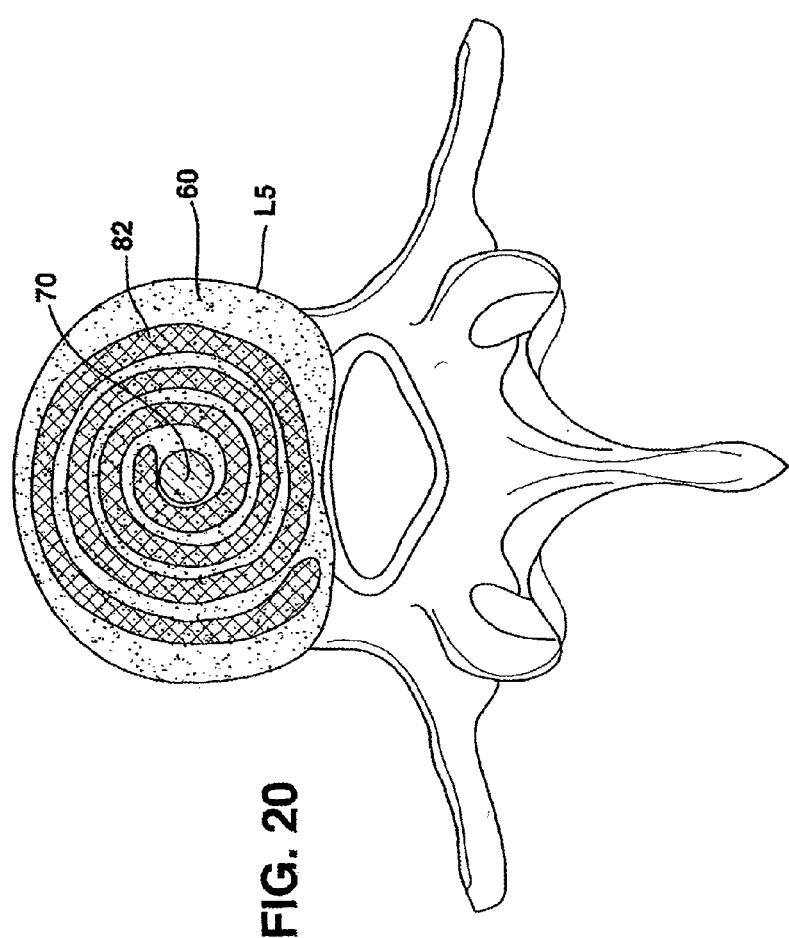
FIG. 20 is an axial view, taken along lines 20-20 of FIG. 19 illustrating the spiral configuration of the spinal disc implant.

Another form of axial spinal implant that promotes fusion while maintaining the distraction spacing can comprise one or more a spring tension, spiral spinal disc implants (spiral members) that can be straightened and introduced into the spinal disc space through an introducer tube lumen or directly through the TASIF axial bore 152 and that return to the spiral form shown in FIG. 20 upon ejection into the spinal disc space 154. The spiral member cross-section of the spiral member can be circular or rectangular or any other suitable shape, and the spiral height is selected to fit within the disc space 154 and extend between the distracted vertebral body endplates. For example, a rectangular cross section strip of nickel-titanium alloy (Nitinol) having a spiral shape memory can be straightened, advanced through the lumen of an introducer tube lumen, and released o assume the planar spiral shape within the disc space 154.

In all of these cases, additional bone growth material may be dispensed in the disc space 154 to fill gaps as shown in FIG. 20. In addition, each of these spinal disc implants can be pinned in the disc space 154 by bone growth material or a pre-formed, rod shaped, axial spinal implant 70 extending through the TASIF axial bore 152 and the central hole of the toroidal or tire shaped or spirally arranged spinal disc implant tube 82 as shown in FIGS. 19 and 20. This therapeutic procedure of the present invention can be advantageously conducted without any injury to any ligaments, muscles and facet joints of the spinal motion segment.

Functional Disc Replacement Implant:

As described above, the complete and partial discectomy procedures followed by a functional disc replacement implant conducted in the past have been done through lateral exposure of the disc that presents a number of problems that are eliminated by the present invention.

In this aspect of the present invention, various forms of spinal disc implants that mimic the function and characteristics of a natural disc without promoting fusion of the cephalad and caudal vertebral bodies can be inserted into the disc space through the TASIF axial bore 152 and percutaneous tract 26 and maintained there in a variety of ways. One approach is to dispense a deflated, shaped bag or balloon or sack or other envelope of a type described in the above-referenced '326 and '454 patents and in U.S. Pat. Nos. 5,888,220 and 5,562,736 into the disc space 154 formed in FIG. 14. Then, the envelope 80 is filled and inflated with a curable biomaterial that does not necessarily encourage bone growth and preferably is resilient. The '326, '220 and '736 patents describe performing a discectomy through lateral approaches to remove the nucleus while retaining as much of the annulus as possible, given the lateral penetration through it. In accordance with this aspect of the present invention, the annulus is removed in the complete discectomy described above, and the deflated envelope 80 is inserted and inflated through the TASIF axial bore 152 and percutaneous tract 26 as shown in FIG. 17 and described above. The envelope 80 conforms with the prepared disc space, and the dispensed biomaterial is confined therein to maintain the spacing between the vertebral body end plates when the envelope opening is closed as described above and depicted in FIGS. 18-20. The dispensed biomaterial confined within the envelope maintains the distraction spacing between the prepared vertebral body endplates but does not necessarily encourage fusion.

The preparation of the disc space 154, the form of the spinal disc implant, and the manner of inserting, filling, closing and locking the spinal disc implant in place can be the same as described in the above section related to spinal fusion with respect to FIGS. 17-20.

In this case, the biomaterial filling the envelope 80 is a material that is capable of being introduced to the site of a joint by minimally invasive means, and be hydrated or cured in place to provide desired physical-chemical properties as described, for example, in the above-referenced '326, '454, '220 and '736 patents. A hydrogel can be injected into the envelope 80 in a liquid or dry particulate form or in microspheres or beads in the manner shown in FIG. 18. A preferred hydrogel is formulated as a mixture of hydrogel polyacrylonitrile or any hydrophilic acrylate derivative with a unique multiblock copolymer structure or any other hydrogel material having the ability to imbibe and expel fluids while maintaining its structure under various stresses. For example, the hydrogel can be formulated as a mixture of polyvinyl alcohol and water. The hydrogel core formed within the envelope 80 will swell as it absorbs fluids through the porous fabric wall of the envelope 80 much like a native nucleus. The hydrogel core has a time constant of swelling which is highly similar to that of the natural nucleus and will thus experience a 5-30% and preferably a 15-20% volume change depending on load over the course of 2-8 (preferably 4-8) hours. When fully hydrated, the hydrogel core will have a water content of between 25-65%. The hydrogel material of the preferred embodiment is manufactured under the trade name Hypan® by Hymedix International, Inc. In addition, any of the hydrogels and solvents identified in the above-referenced '326 patent may be employed to fill the envelope 80

The preferred woven construction of the envelope creates a plurality of small openings large enough to allow bodily fluids to interact with the hydrogel core, but small enough to prevent the hydrogel from escaping. Preferably, the openings have an average diameter of about 10 micrometers, although other dimensions are acceptable. While the fabric is described as woven, any other configuration having a semi-permeable or porous attribute can be used. The flexible material allows expansion and contraction of the hydrogel core in a controlled fashion as it imbibes and expels fluids. The hydrogel core acts as a cushion against various loads placed upon it. The hydrogel core imbibes surrounding fluids and expands as the load is decreased (e.g. when the patient reclines). To help achieve this effect, the preferred envelope fabric is substantially inelastic and has a burst strength which is greater than the swelling pressure of the hydrogel core when fully hydrated to prevent rending and loss of the hydrogel core. Suitable envelope materials include This therapeutic procedure of the present invention provides a shock absorbing functional disc replacement of the nucleus of the spinal disc and can be advantageously conducted without any injury to any ligaments, muscles and facet joints of the spinal motion segment.

Partial Discectomy:

In many instances, it is preferable to perform a partial discectomy or disc decompression where the annulus is largely intact and relief from pain caused by a rupture or swelling against the spinal cord or nerves is sought. As described above, the partial discectomy procedures conducted in the past have been done through lateral exposure of the disc that presents a number of problems that are eliminated by the present invention.

In this aspect of the present invention, the anterior or posterior TASIF axial bore 152 or 22 is formed in the manner described above and terminates within the nucleus of the disc to be treated or optionally extends into the cephalad vertebral body to facilitate fusion of the vertebral bodies. Then, instruments can be introduced through the TASIF axial bore and percutaneous tract into the nucleus to fragment or desiccate all or part of the nucleus, including any projecting into the annulus or from a fissure in the annulus, and create a void or disc cavity within the annulus and the cartilaginous endplates. Any fissures or other damage or weakening of the annulus can be treated from within the created void in a manner described in the above-referenced '149 patent, for example. In a simple decompression, the entry into the nucleus and the TASIF axial bore can then be closed with a simple elongated axial spinal implant or a shorter plug formed of a bone growth material or another bio-compatible material or bone cement. Alternatively, a disc augmentation can be performed before closure as described further below.

Figure 21:
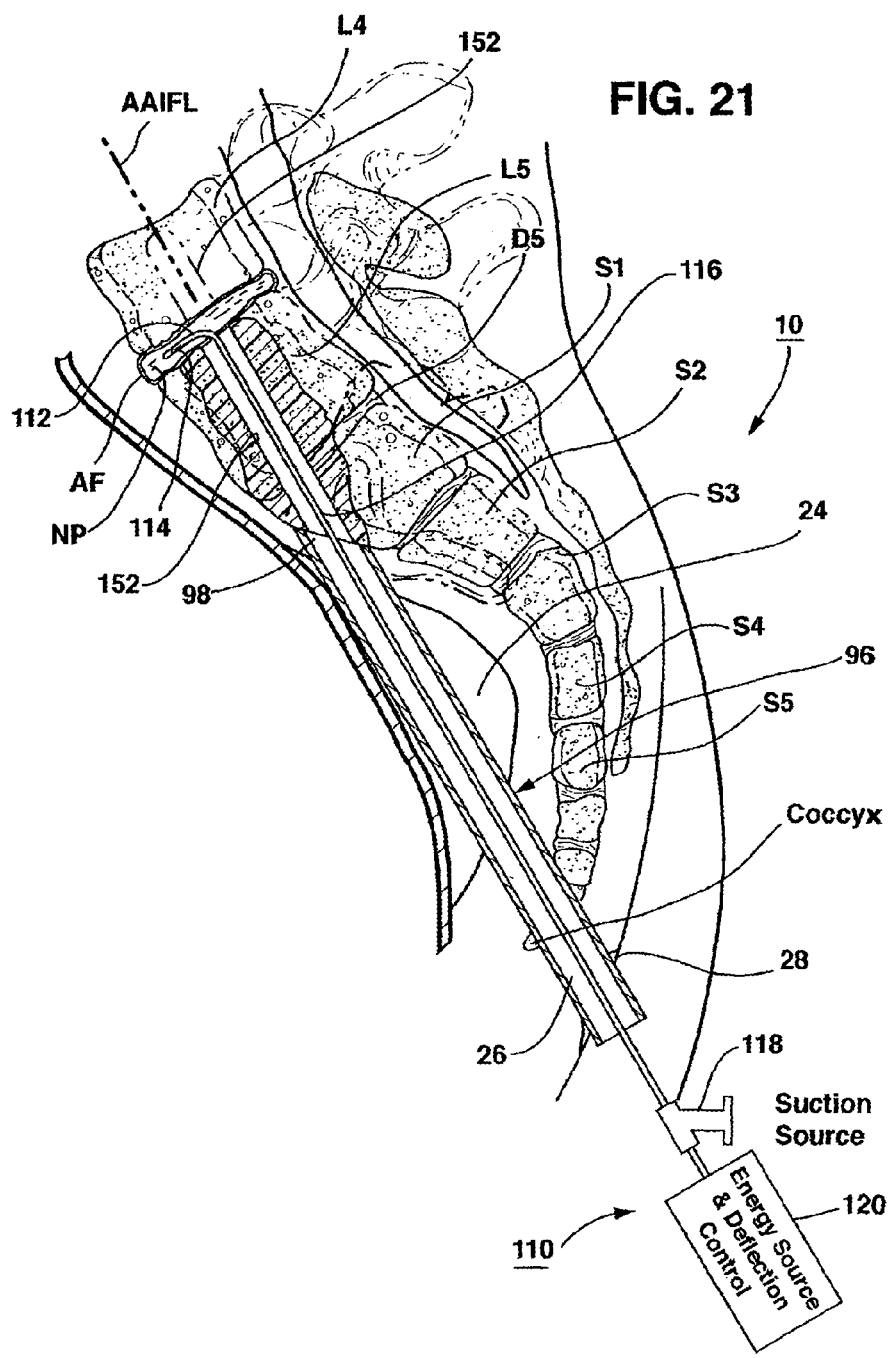
FIG. 21 illustrates, in a partial cross-section side view, one manner of performing a partial discectomy effected through a TASIF axial bore of at least a portion of the nucleus of a spinal disc while leaving the annulus intact.

FIG. 21 illustrates, in a partial cross-section side view, one manner of performing a partial discectomy of a spinal disc to remove at least a portion of the nucleus NP effected through a TASIF axial bore 152 while leaving the annulus AF intact. A discectomy tool 110 is inserted through the axially aligned anterior tract 26 defined by the lumen of the anterior tract sheath 96 and the TASIF axial bore 152. The discectomy tool 110 is formed like a flexible atherectomy catheter for fragmenting and removing obstructions in blood vessels using a cutting head 114 to fragment or desiccate the disc material and aspiration with saline flushing to remove the fragments or byproducts from the void or cavity created in the annulus. The cutting head 114 is mounted into a deflectable or steerable distal end section 112 of discectomy tool shaft 116 extending through the TASIF axial bore 152 and anterior tract 26 from an externally disposed energy source and deflection control 140.

The cutting head 114 may comprise any of the known types, e.g. mechanical cutters including rotating wire brushes, cutting blades, scissors, screws, bits, extendable/retractable rotating wires, or fluid jets or the like. Or, the cutting head 114 may be an energy emitting head, e.g., a resistive heating, electrocautery, laser energy, or ultrasonic energy head that desiccates, that is, heats up and shrinks or vaporizes the nucleus. The cutting head 114 can comprise one of various forms of cutting heads disclosed in the above-referenced patents '258 and '146, '149, '258, '597, '962, '629 and '884 patents, for example. Again, however, the tool shafts of the prior art discectomy tools are designed for the lateral access into the spinal disc and are not disclosed as being introduced axially and then into the space between the vertebral body endplates and do not have the capability of being introduced in this manner.

For example, the cutting head 114 can comprise a cutting wire that is projected from a side opening in the distal end section 112 as a loop that is rotated to slice sections of the nucleus into fragments that are aspirated through a lumen of the discectomy tool shaft 116. The distal end section 112 may be angularly deflected using a deflection mechanism, e.g., a pull wire within a pull wire lumen of the elongated, flexible, discectomy tool shaft 116 and a proximal pull wire control of the proximal guiding and cutting mechanism 120 coupled thereto. The cutting head 114 may be pulled back and forth laterally and/or swept in a 360° arc about the axial bore 152 to traverse and excise selected symptomatic portions of the spinal disc D4 including the internally disposed nucleus NP and to cut away an portion of it that is extruded through a fissure in the annulus AF by manipulation of the proximal end portion of the discectomy tool shaft 116 extending from the skin incision 28. The complete discectomy cutting head 114 and tool shaft 116 are shown schematically and not necessarily to scale to one another or to the TASIF axial bore 152.

The retractable/expandable cutting wire of exemplary cutting head 114 can be extended out of and retracted back into the cutting head 114. The distal section 112 is attached to a drive shaft extending through a drive shaft lumen of the tool shaft 116 to a drive motor included in energy source and deflection control 120 for rotating the drive shaft and cutting head 114. A deflection control for operating the pull wire or the like for deflecting the distal section 112 is also included in energy source and deflection control 120. Preferably an aspiration lumen is included within the discectomy tool body 116 with a distal opening adjacent to the cutting head 114 and terminating proximally at a side suction port 118 adapted to be coupled to a source of suction to aspirate the fragments of the nucleus from the cavity formed inside the annulus of spinal disc D4. A saline flush lumen and supply can also be incorporated within to flush excised fragments for aspiration.

The operation and movement of the cutting head 114 about the interior of spinal disc D4 is preferably observed employing fluoroscopy or other radiographic visualization techniques. An endoscopic visualization or discoscopy of the cavity formed within the annulus AF could also be employed using a separate or incorporated deflectable tip endoscope for illumination and observation of the site. Weakened or damaged sections or fissures in the annulus AF can be visually detected in this way.

In addition, further instruments and materials can be introduced into the cleared space to maintain distraction spacing of the vertebral bodies D4 and D5 and to make repairs to weakened or damaged sections or fissures of annulus AF.

Such repairs can be made by heat treatment or by the application of a biocompatible patching material, such as a fibrin glue, against the interior surface of the annulus AF by inflation of a balloon within the cavity as described in the above-referenced '149 patent.

This therapeutic procedure of the present invention allows the partial discectomy to be advantageously conducted without any injury to any ligaments, muscles and facet joints of the spinal motion segment.

Disc Augmentation and Fusion:

In addition, it is also possible to augment a spinal disc by introducing one or more artificial spinal disc implant or other biomaterials to provide a functional disc replacement implant or bone growth materials to effect fusion into the void or cavity that is made within the annulus AF, thereby employing the annulus AF to retain the introduced implants or biomaterials or fusion enhancing materials in place. The annulus AF can itself be used as an envelope to contain the delivered disc augmentation materials comprising spinal disc implant(s), bone growth material or other biomaterials. Optionally, means are provided to contain the disc augmentation materials within the desired space, e.g., by delivering the disc augmentation materials into an additional envelope within the cavity as described above with reference to FIGS. 17-20. To effect fusion, the TASIF axial bore 152 may be extended into the cephalad vertebral body and axial spinal implants and/or bone growth material dispensed within the cavity and the TASIF axial bore 152 as described above with reference to FIGS. 19-20. Or a portion of the caudal and cephalad cartilaginous endplates and vertebral body endplates can be removed in the partial discectomy to expose vertebral bone to promote fusion with the bone growth materials dispensed into the cavity.

Figure 22:
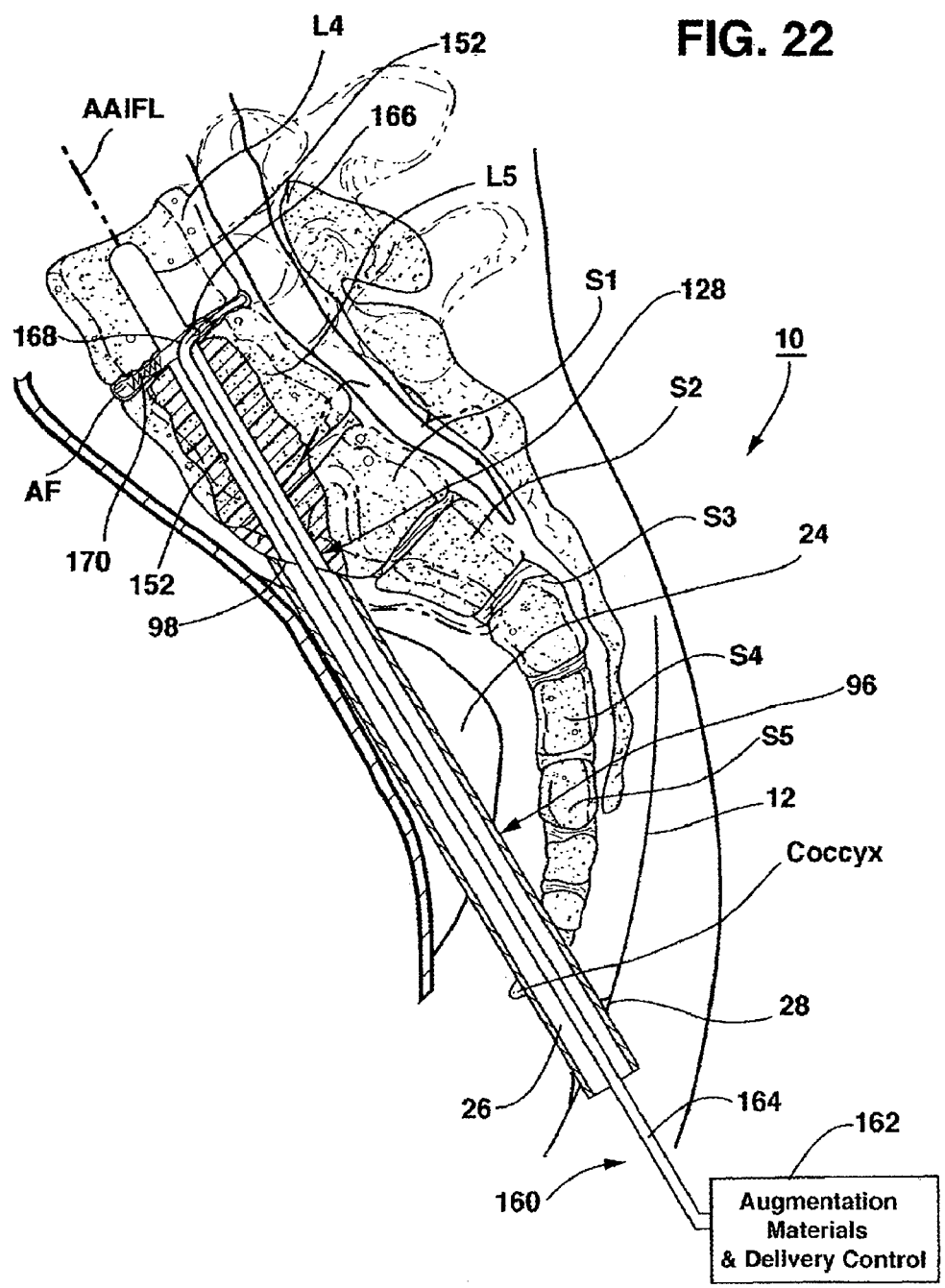
FIG. 22 illustrates, in a partial cross-section side view, one manner of filling the annulus emptied in FIG. 21 with a disc augmentation material selected from bone growth materials and other biomaterials effected through a TASIF axial bore.
Figure 23:
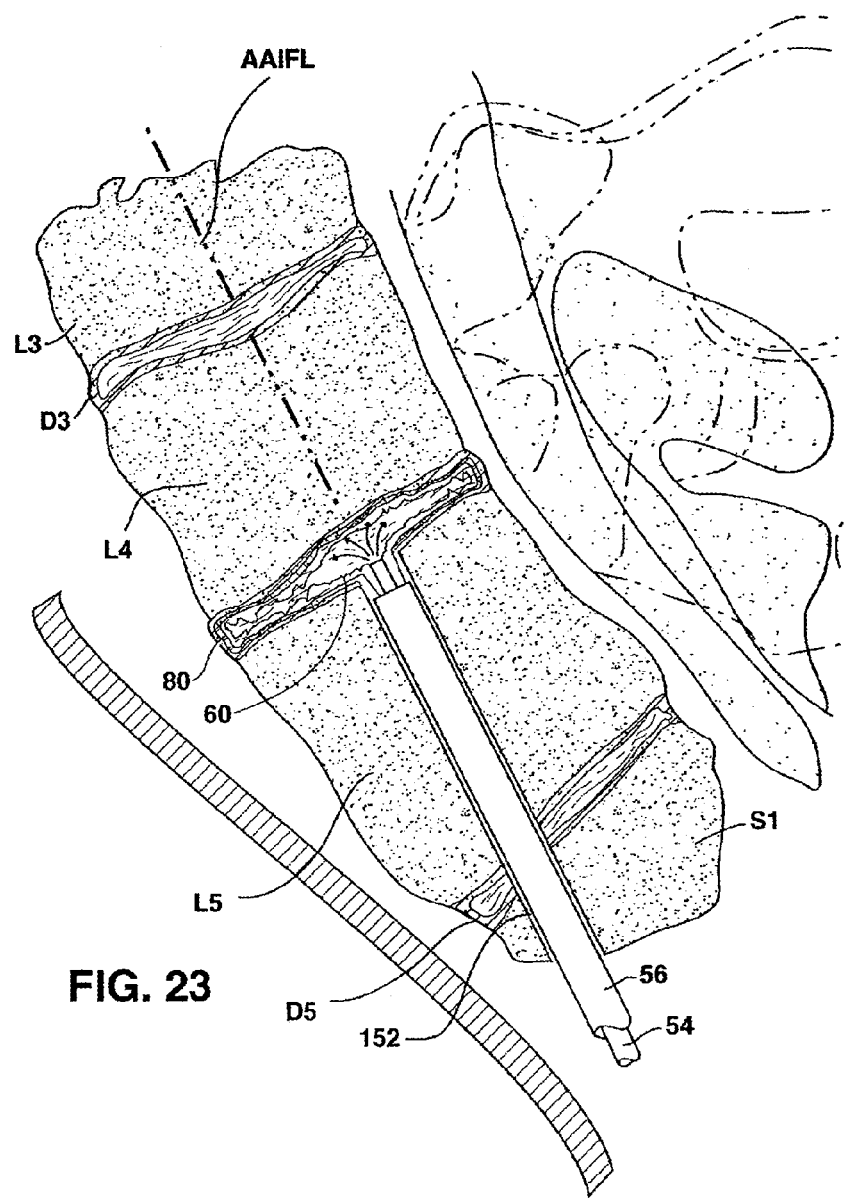
FIG. 23 is an enlarged partial cross-section view illustrating a disc augmentation of a disc involving inflating a balloon with material injected into the balloon within the empty disc space formed in FIG. 21.
Figure 24:
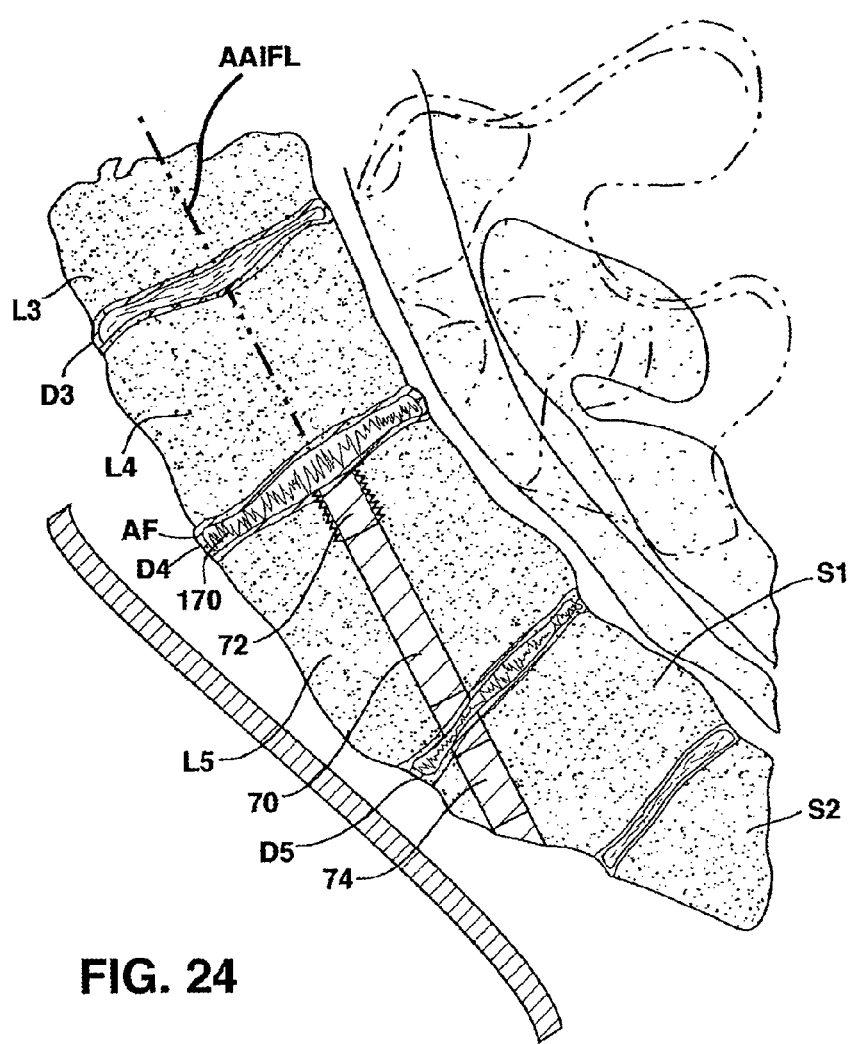
FIG. 24 is an enlarged partial cross-section view illustrating closure of the TASIF axial bore following the partial discectomy of FIG. 21 or the disc augmentation of FIG. 22 or 23.

Dispensing of bone growth or other biomaterials directly into the prepared cavity or into an envelope within the prepared cavity is illustrated, for example, in FIGS. 22-24. FIG. 22 depicts a disc augmentation tool 160 having a proximal source of augmentation materials 162 coupled to an augmentation tool shaft 164 for delivering augmentation materials to distal exit port 166 in a deflectable distal section 168 of the augmentation tool shaft 164. The augmentation procedure is illustrated in FIG. 22 in the context of employing the anterior TASIF axial bore 152 or pilot hole 150, but FIG. 22 is intended to convey how the same procedure would be employed using augmentation tool 160 to augment discs accessed via the posterior TASIF axial bore or pilot hole.

The disc augmentation procedure employs augmentation material 170, e.g., a solid particulate material or a biomaterial or a bone growth material of the types described above introduced in a fluid form to solidify in situ within the annulus AF to provide support as a spinal disc implant between the opposed vertebral bodies. The disc augmentation materials 170 can be pumped or otherwise delivered directly into each disc cavity through the distal exit port 166 located within the cavity. Then, the caudal opening into the spinal disc is closed with an artificial plug 72 inserted into the TASIF axial bore 152 and fixed in place as shown in FIG. 24. The plug 72 is threaded into or otherwise attached to vertebral bone with sufficient holding force to resist the pressure on the disc augmentation material 170 when an axial load is placed on the spinal column to thereby prevent its expulsion into the TASIF axial bore. The plug 72 can be of any suitable length and could extend all the way to the anterior target point. As illustrated in FIG. 24, the remaining caudal length of the TASIF axial bore is preferably filled with one or more axial spinal implant 70 and 74 or with bone growth material.

Alternatively, the disc augmentation materials can be pumped or otherwise delivered directly into the TASIF axial bore 152 as the augmentation tool is withdrawn to fill the disc cavity and the TASIF axial bore, particularly if the therapy comprises fusion of the cephalad and caudal vertebral bodies. Then, the plug 72 may be inserted in more caudally in the vertebral body L5. Moreover, the TASIF axial bore 152 may extend in the cephalad direction in vertebral body L4 as shown in the broken lines of FIG. 21, and the elongated TASIF axial bore can be filled with bone growth material and/or an axial spinal implant bridging the augmented spinal disc D4 in the manner shown in FIG. 19, for example.

FIG. 23 illustrates the implantation and filling of an envelope 80 within the disc cavity. The envelope 80 may be implanted, filled with a variety of bone growth or biomaterials and closed in the same manner as described above in reference to FIGS. 17-20. In this case, the envelope 80 is confined and maintained in place by the annulus AF, and the closure of the TASIF axial bore 152 can be effected in the manner described above to prevent caudal expulsion of the filled envelope 80. In addition, the envelope 80 or other axial spinal implant fitted into the annulus AF may be shaped as described above as a toroidal or planar spiral form as described above with reference to FIGS. 19 and 20.

These therapeutic procedures of the present invention can be advantageously conducted without any injury to any ligaments, muscles and facet joints of the spinal motion segment.

Vertebroplasty:

As described above, the vertebroplasty procedure involves forcing vertebral body repairing or reinforcing material comprising bone growth material or bone cement for repairing or reinforcing the vertebral body into the cancellous bone of the fractured vertebral body. In the past, vertebroplasty has been done through a lateral exposure and penetration of the cortical bone of a side surface of the vertebral body. As noted above, the lateral approach presents a number of problems that are eliminated by the present invention.

One approach to performing a vertebroplasty in accordance with the present invention is to simply bore one or more small diameter TASIF axial bore into the fractured cancellous bone, introduce a catheter into the TASIF axial bore, and to pump in the bone growth material or bone cement so that it penetrates and fills the fissures in the cancellous bone. Then, the caudal end of the TASIF axial bore is closed where it passes through the harder cortical bone forming the caudal vertebral endplate, e.g., by use of a threaded plug as described above. This procedure may be repeated at several different angles.

Figure 25:
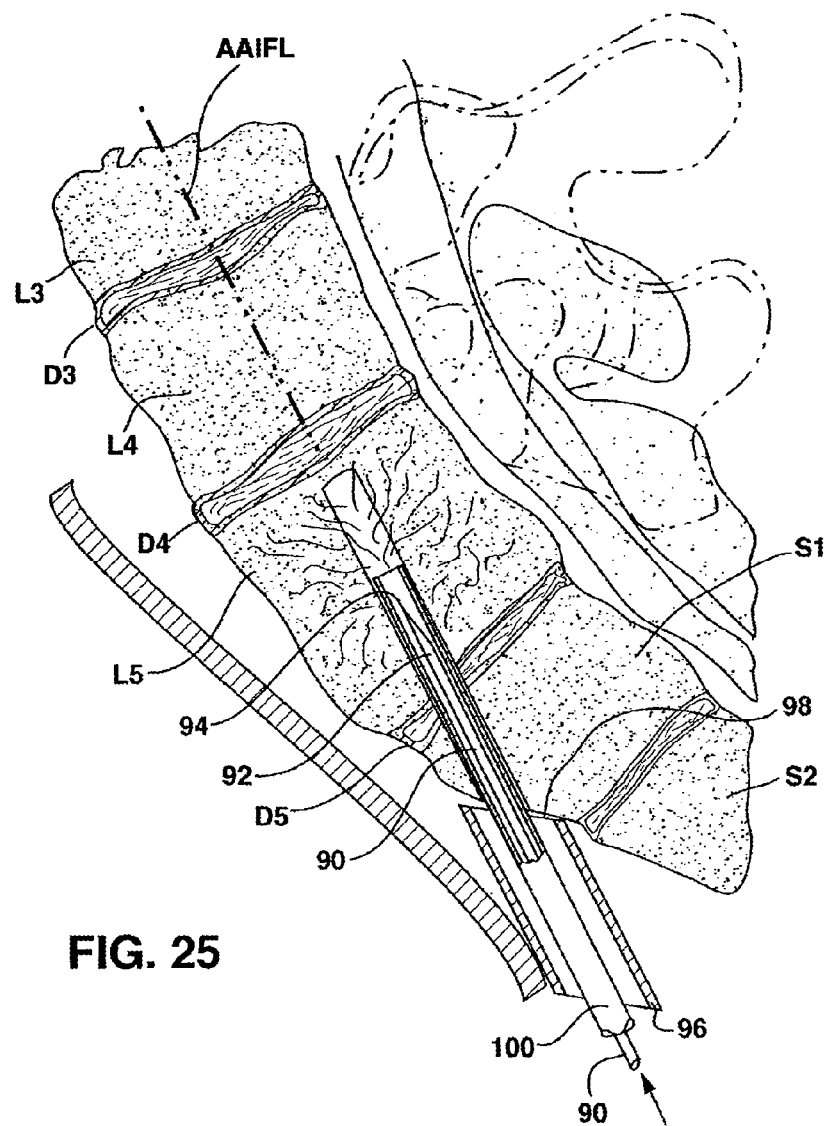
FIG. 25 illustrates, in a partial cross-section side view, one manner of performing a vertebroplasty through direct injection of bone growth material into a fractured vertebral body through at least one TASIF axial bore.
Figure 26:
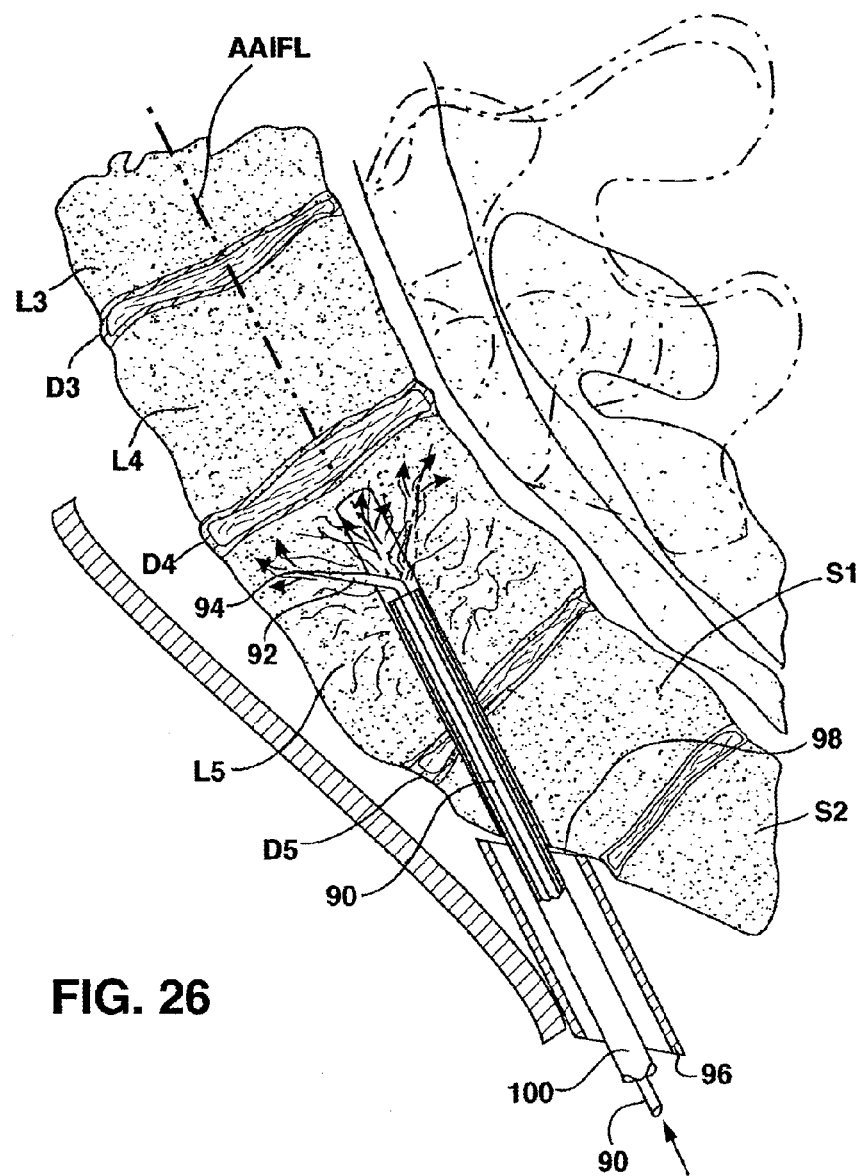
FIG. 26 is a cross-section view, taken along lines 21-21 of FIG. 20, illustrating the direct injection of the bone growth material into various locations within the fractured vertebral body of FIG. 20.

FIGS. 25 and 26 illustrate steps of performing a vertebroplasty through direct injection of a bone growth material of one of the types described above into a fractured vertebral body L4 through at least one TASIF axial bore 152, although several, small diameter diverging TASIF axial bores could be advantageously employed in performing this therapy. It will be assumed that the vertebral body L4 may also be somewhat collapsed.

A preferred vertebroplasty procedure of the present invention is performed via a posterior or anterior TASIF axial bore(s) using an elongated catheter 90 having a deflectable distal end portion 92 and exit port 94 that is introduced through the lumen of an elongated introducer 100. The distal end portion 92 straightens when confined within the lumen of the stiffer catheter 90 as shown in FIG. 25 and is curved upon release as shown in FIG. 26. The distal end portion 92 and exit port 94 can be aimed somewhat laterally toward the cortical bone and then advanced in any direction away from the TASIF axial bore 152 by retracting introducer 100 and/or advancing catheter 90. The tapered end of the catheter 90 enables its advancement into the soft, fractured cancellous bone where the bone growth material is pumped in under pressure. The process is repeated several times to distribute the bone growth material. Bone growth material is also dispensed as the catheter and sheath are withdrawn. Then, the caudal end of the TASIF axial bore where it passes through the harder cortical bone forming the caudal vertebral endplate is closed, e.g., by use of a threaded plug as described above.

It should also be noted that the vertebroplasty procedure of the present invention can be advantageously conducted in conjunction with a discectomy, fusion of a spinal motion segment or disc augmentation employing the same TASIF axial bore and optionally including implantation of an elongated axial spinal implant into the TASIF axial bore to maintain alignment, strengthen and stabilize the spinal motion segment. This therapeutic procedure of the present invention can be advantageously conducted without any injury to any ligaments, muscles and facet joints of the spinal motion segment.

Balloon-Assisted Vertebroplasty:

As described above, the balloon-assisted vertebroplasty procedure involves forming an enlarged vertebral body cavity within a fractured and often collapsed vertebral body by introducing and inflating an elastic balloon or an inelastic, shaped balloon under pressure sufficient to compress the cancellous bone toward the cortical bone and to restore the shape of a compressed vertebral body. Then, the balloon is deflated, and either withdrawn so that the vertebral body cavity can be filled with vertebral body reinforcing material for reinforcing the vertebral body or left in place and filled with vertebral body reinforcing material. In the past, the balloon and bone growth material have been introduced through a lateral exposure and penetration of the cortical bone of a side surface of the vertebral body. As noted above, the lateral approach presents a number of problems that are eliminated by the present invention.

Figure 27:
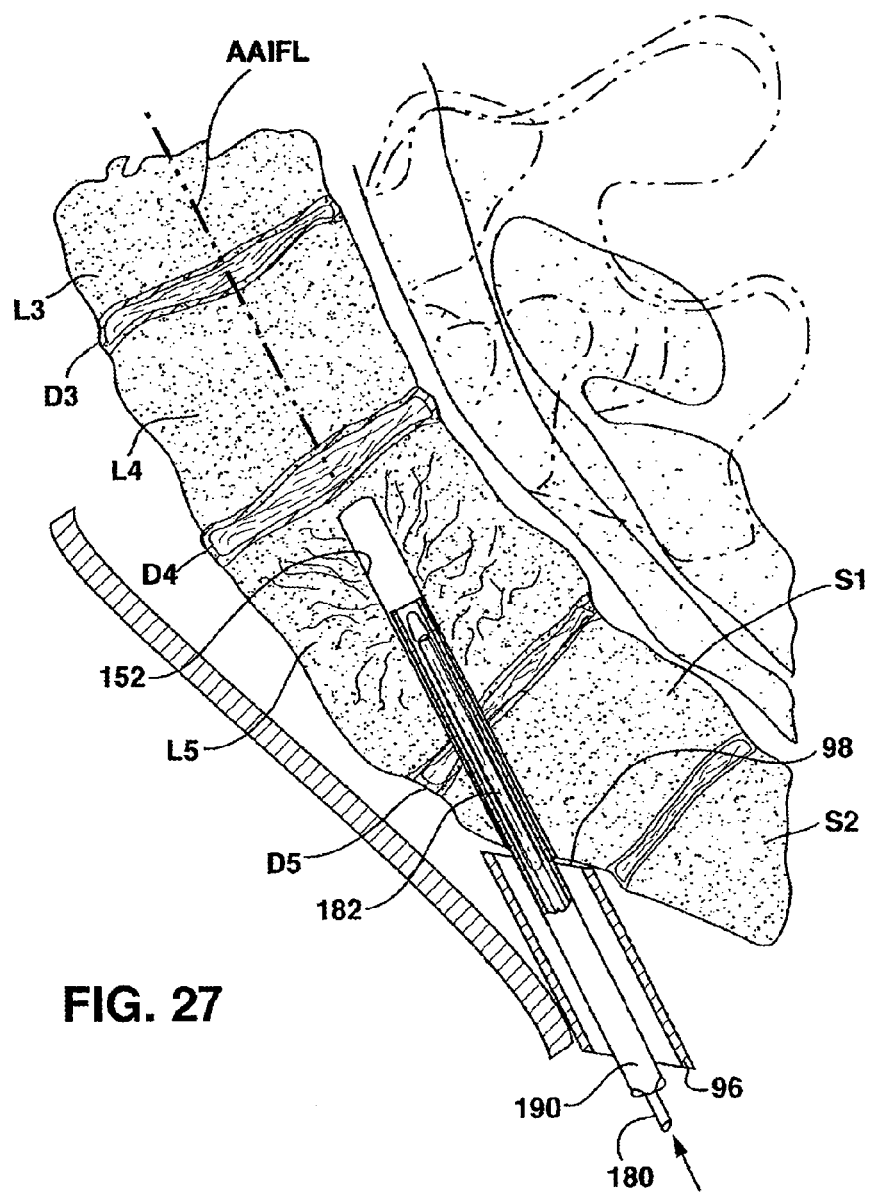
FIG. 27 illustrates, in a partial cross-section side view, an initial step of one manner of performing a balloon-assisted vertebroplasty comprising introducing and inflating a shaped balloon within a TASIF axial bore to compress the cancellous bone and form a vertebral bone cavity.
Figure 28:
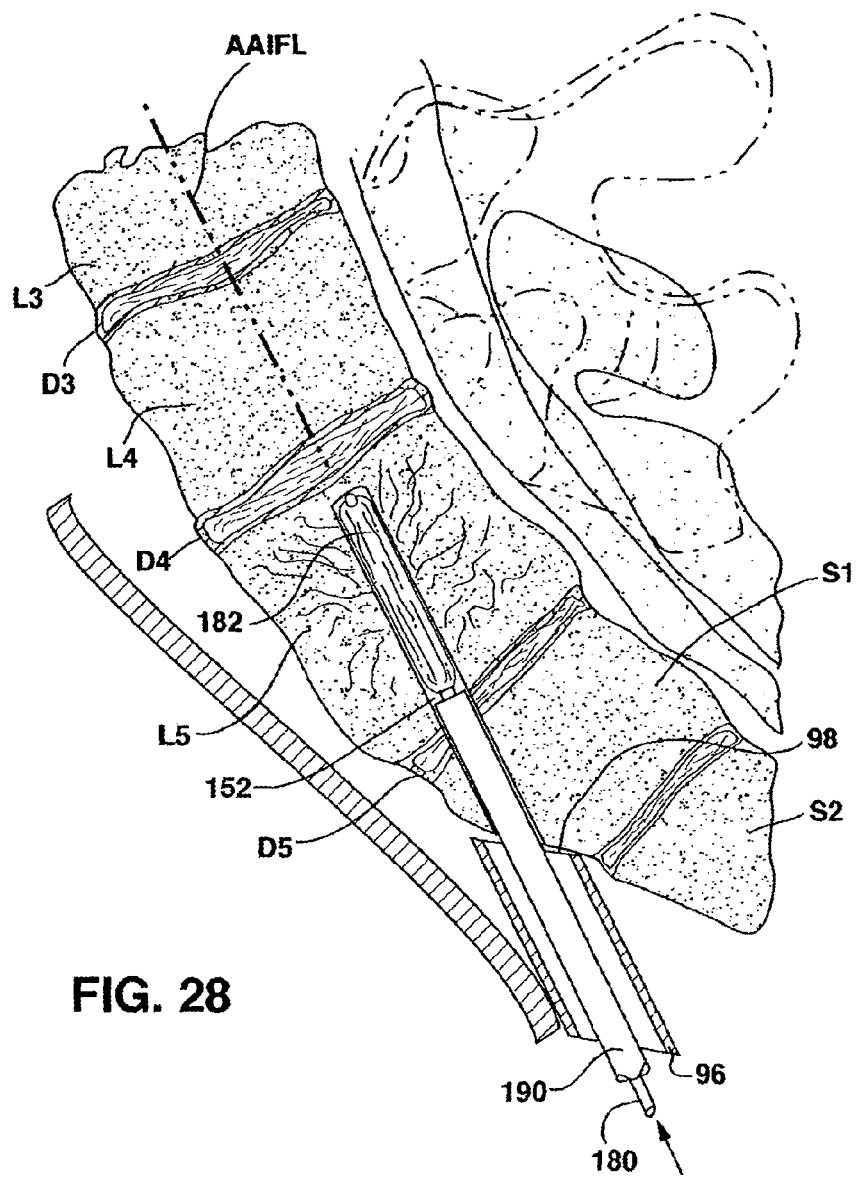
FIG. 28 illustrates, in a partial cross-section side view, an initial step of inflating the balloon within the cancellous bone of the fractured vertebral body.

FIGS. 27-31 illustrate one manner of performing a balloon-assisted vertebroplasty of a fractured vertebral body L5 in accordance with this aspect of the present invention. A balloon catheter 180 bearing a deflated, inelastic, symmetric or asymmetric, shaped balloon 182 is introduced either within the lumen of an introducer 190 or over a guidewire (not shown) or by itself through the lumen of anterior tract sheath 96 and the TASIF axial bore 152 into the vertebral body D5 in FIG. 27. The cavity forming balloon 182 can either be formed over a distal end segment of the balloon catheter body to expand outward therefrom as shown in FIGS. 27 and 28 or extends distally from the distal end of the balloon catheter body. In the former case, if the balloon is asymmetric, the balloon catheter 180 is rotated to orient the asymmetric balloon 182 in the proper relation to the vertebral body employing markers on the proximal balloon catheter body. In the latter case, the deflated balloon is deployed through the length of the axial bore 152 within the vertebral body in the desired orientation employing markers on the proximal balloon catheter body.

Figure 29:
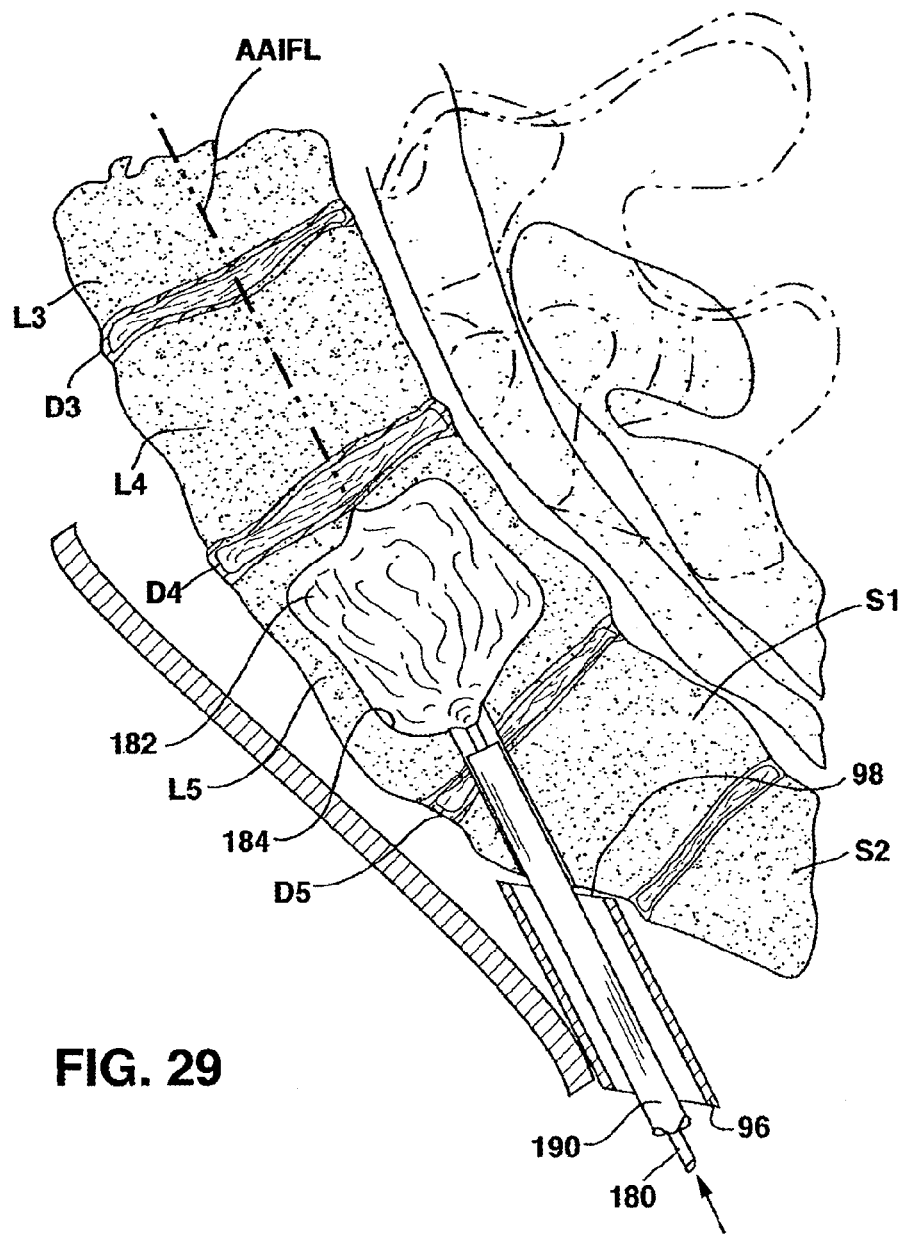
FIG. 29 illustrates, in a partial cross-section side view, the full inflation of the balloon within the cancellous bone of the fractured vertebral body.
Figure 30:
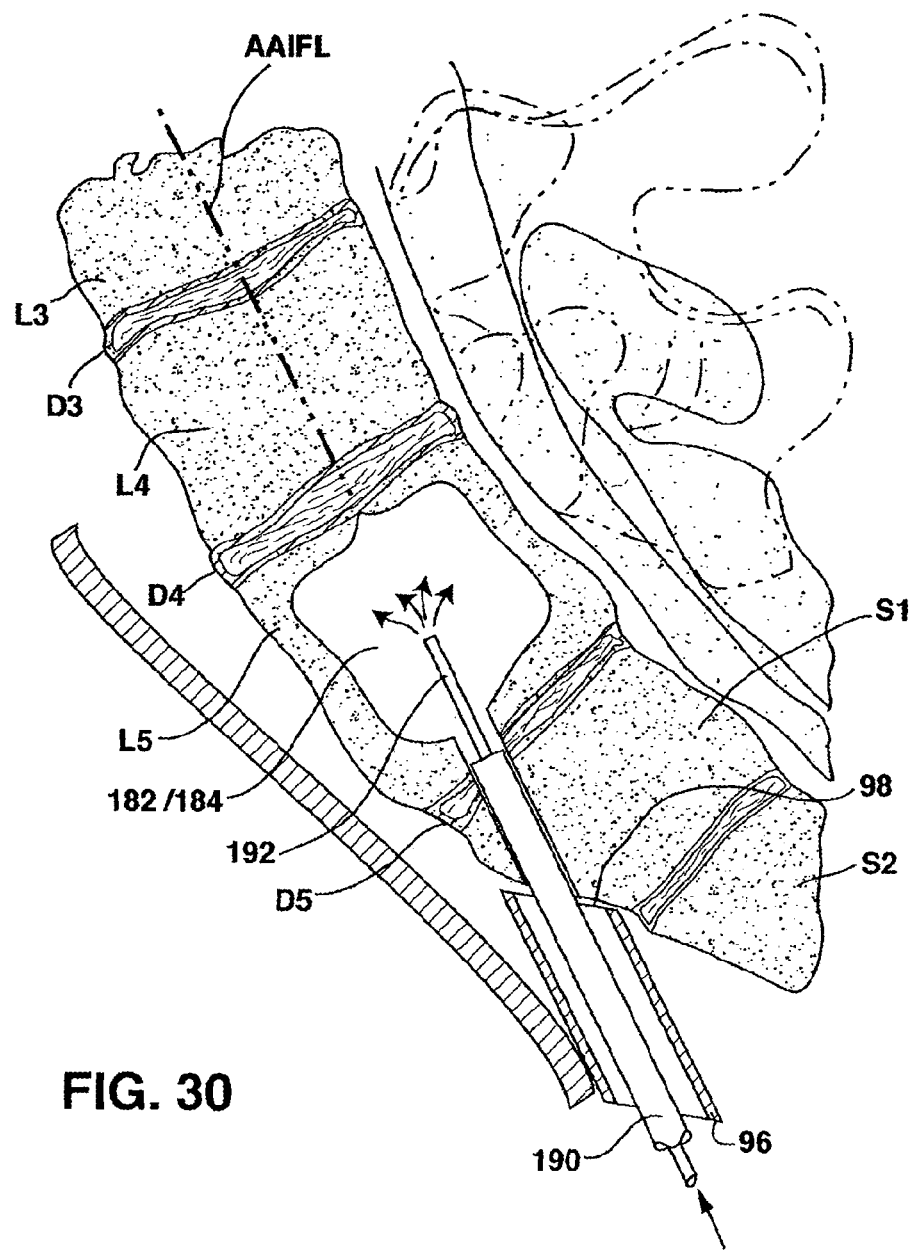
FIG. 30 illustrates, in a partial cross-section side view, a further step of performing the balloon-assisted vertebroplasty comprising introducing bone growth material through the TASIF axial bore into the vertebral bone cavity formed by the shaped balloon or into the balloon itself.
Figure 31:
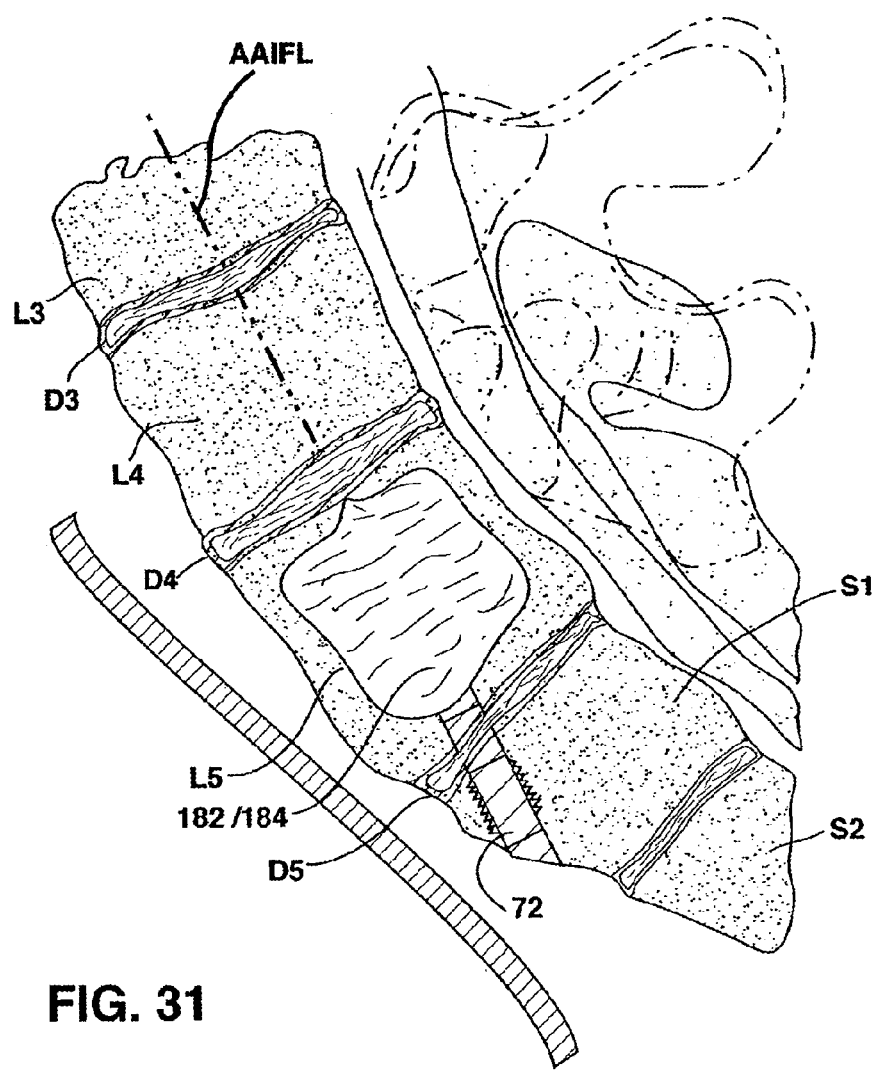
FIG. 31 illustrates the filled cavity of the vertebral body and a plug closing the TASIF axial bore.

Then, in FIGS. 28 and 29, the introducer 190 is retracted and the balloon 182 is inflated with a radiographic fluid enabling fluoroscopic visualization to compress the cancellous bone toward the cortical bone, thereby forming a vertebral bone cavity 184 shaped by the balloon shape and the resistance to deformation. Then, the balloon 182 is deflated and is withdrawn so that the cavity 184 can be filled with bone growth material by itself as shown in FIG. 30. In FIG. 30, a dispensing catheter 192 is inserted through introducer 190 or directly through the axial bore 152, and either an empty balloon 182 or the vertebral bone cavity 184 is filled with a bone growth or bone cement. Or the cavity forming balloon 182 can be filled with a biomaterial that cures and solidifies in situ. Alternatively, bone growth material or bone cement can be confined within a further porous balloon or envelope that is closed and left in place in the cavity 184. The caudal end of the TASIF axial bore 152 is closed where the bore 152 traverses passes through the harder cortical bone forming the caudal vertebral endplate, e.g., by use of a threaded plug 72 as described above. This balloon-assisted vertebroplasty procedure may be repeated using two or more TASIF axial bores and balloon catheters introduced into different areas of the vertebral body.

In the case where a balloon or envelope is filled with bone growth material and left in the cavity 184, it is preferably porous to allow fluid transfer and bone growth through the pores. Consequently, a separate, shaped balloon than the balloon 182 is inserted into the cavity and is filled in the manner described above with respect to disc augmentation FIGS. 17 and 18, detached from a material fill catheter, and the balloon or envelope opening is closed.

It should also be noted that the balloon-assisted vertebroplasty procedure of the present invention can be advantageously conducted in conjunction with a discectomy, fusion of a spinal motion segment or disc augmentation employing the same TASIF axial bore and optionally including implantation of an elongated axial spinal implant into the TASIF axial bore to maintain alignment, strengthen and stabilize the spinal motion segment. This therapeutic procedure of the present invention can be advantageously conducted without any injury to any ligaments, muscles and facet joints of the spinal motion segment.

Distraction and Shock Absorption:

Further embodiments of posterior and anterior axial spinal implants or rods 200 and 230 of the present invention adapted to be fitted into the posterior and anterior TASIF axial bores 22 and 152 are depicted in FIGS. 32-33 which address the problems of distracting adjacent vertebrae to maintain normal separation and shock absorption of the anterior spine respectively. Distraction of the adjacent vertebrae may relieve pressure on nerves and relieve pain and immobility. The shock absorption of stresses placed on the anterior spine also relieves pain and restores more normal anterior spine loading function. The implantation of these TASIF axial spinal implants 200 and 230 in a TASIF axial bore 152 is depicted in FIG. 34. It is necessary to extend the TASIF axial bore through a spinal disc, and a disc augmentation with a toroidal or spiral artificial disc implant as described above may be performed prior to implantation of these axial spinal implants or rods 200 and 230.

The TASIF axial spinal implant 200 illustrated in FIGS. 32 and 34 comprises a threaded rod 202 extending between a caudal bore engaging body 204 and a cephalad axial bore engaging body 206. The center portion of the threaded rod 202 may be straight as shown for insertion into an anterior TASIF axial bore 152 or curved for insertion of implant 200 into a posterior TASIF axial bore 22. In use, after the cephalad axial bore engaging body 206 is fully seated into the TASIF axial bore, the caudal bore engaging body 204 and the threaded rod are rotated with respect to one another to cause the caudal bore engaging body 204 and a cephalad axial bore engaging body 206 to separate from one another as shown by arrow 216. If the caudal bore engaging body 204 grips the TASIF axial bore traversing the caudal vertebrae sufficiently, then the caudal and cephalad vertebrae will be distracted as the caudal bore engaging body 204 and cephalad axial bore engaging body 206 to separate from one another.

This may be accomplished in several ways. As shown in FIG. 32, the threaded rod 204 has a male threaded caudal rod end 208 that is clockwise threaded to engage the female threaded bore of the caudal bore engaging body 204 and a male threaded cephalad rod end 210 that is counter-clockwise threaded to engage the female threaded bore of the cephalad bore engaging body 206. The caudal bore engaging body 204 is formed with exterior engaging threads or flanges 212 adapted to bite into the caudal vertebrae by rotating it as the TASIF axial spinal implant 200 is seated into the TASIF axial bore. The threaded rod 204 can then be rotated by engagement of its caudal end and rotation with a distraction tool 220 to thereby increase the distance between the caudal bore engaging body 204 from the cephalad axial bore engaging body 206. Alternatively, cephalad end of the threaded rod 202 could be fixed to the cephalad axial bore engaging body 206, although it would then also be rotated with rotation of the threaded rod 202.

The TASIF axial spinal implant 230 of FIG. 33 possesses a shock absorbing function, two forms of which are illustrated, namely a hydraulic or a spring based, shock absorbing function. A plunger rod 232 extends between a caudal bore engaging body 234 and a cephalad axial bore engaging body 236. The center portion of the plunger rod 232 may be straight as shown for insertion into an anterior TASIF axial bore 152 or curved for insertion of implant 200 into a posterior TASIF axial bore 22. The caudal bore engaging body 234 is formed with exterior engaging threads or flanges 242 adapted to bite into the caudal vertebrae by rotating it as the TASIF axial spinal implant 230 is seated into the TASIF axial bore. For simplicity of illustration, the caudal bore engaging body 234 is shown and described below incorporating a spring-based shock absorbing function and the cephalad axial bore engaging body 236 is shown and described below incorporating a hydraulic fluid based shock absorbing function. It will be understood that one or the other shock absorbing function could be incorporated in a given TASIF axial spinal implant or rod.

The caudal bore engaging body 234 is formed with an interior cavity 248 retaining a spring 240 and the caudal end of the plunger rod 232. A fluid barrier gasket is also employed surrounding the caudal end of the plunger rod 232 to inhibit ingress of body fluids into the interior cavity 248. The cephalad bore engaging body 236 is formed with an interior cavity 238 retaining a shock absorbing fluid and the cephalad end of the plunger rod 232. A fluid barrier gasket is also employed surrounding the cephalad end of the plunger rod 232 to inhibit ingress of body fluids into the interior cavity 238.

In use, after the cephalad axial bore engaging body 236 is fully seated into the TASIF axial bore, the caudal bore engaging body 234 and the rod is rotated with respect to one another using the insertion tool 250 to cause the threads 242 of the caudal bore engaging body 234 to screw into the TASIF axial bore wall. If the caudal bore engaging body 234 grips the TASIF axial bore sufficiently, then the caudal and cephalad vertebrae will be distracted by the length of the plunger rod 232 maintained by the spring force in a resting state. The distance between the cephalad axial bore engaging body 236 and the caudal bore engaging body 234 will shorten and lengthen in the direction of arrow 246 as force or load is exerted between the lumbar vertebrae bodies by spinal movement due to patient activity against spring 240 and then abates, restoring spring length. Other forms of shock absorbing mechanisms can be employed to retain and allow the plunger rod to work against spring forces and/or hydraulic forces.

The caudal and cephalad bore engaging bodies of the axial spinal implants or rods 200 and 230 can be affixed using bone cement or one of the affixation mechanisms disclosed in the above-referenced provisional '748 application and '620 patent application. Bone cement material placed in the TASIF axial bore with the TASIF axial spinal implant cures therein such that fixation occurs between the elongated axial spinal implant and adjacent vertebral bone of sufficient strength to withstand physiological loads until fixation occurs by osteogenic growth between the bone and the caudal and cephalad ends of the TASIF axial spinal implant.

Figure 37:
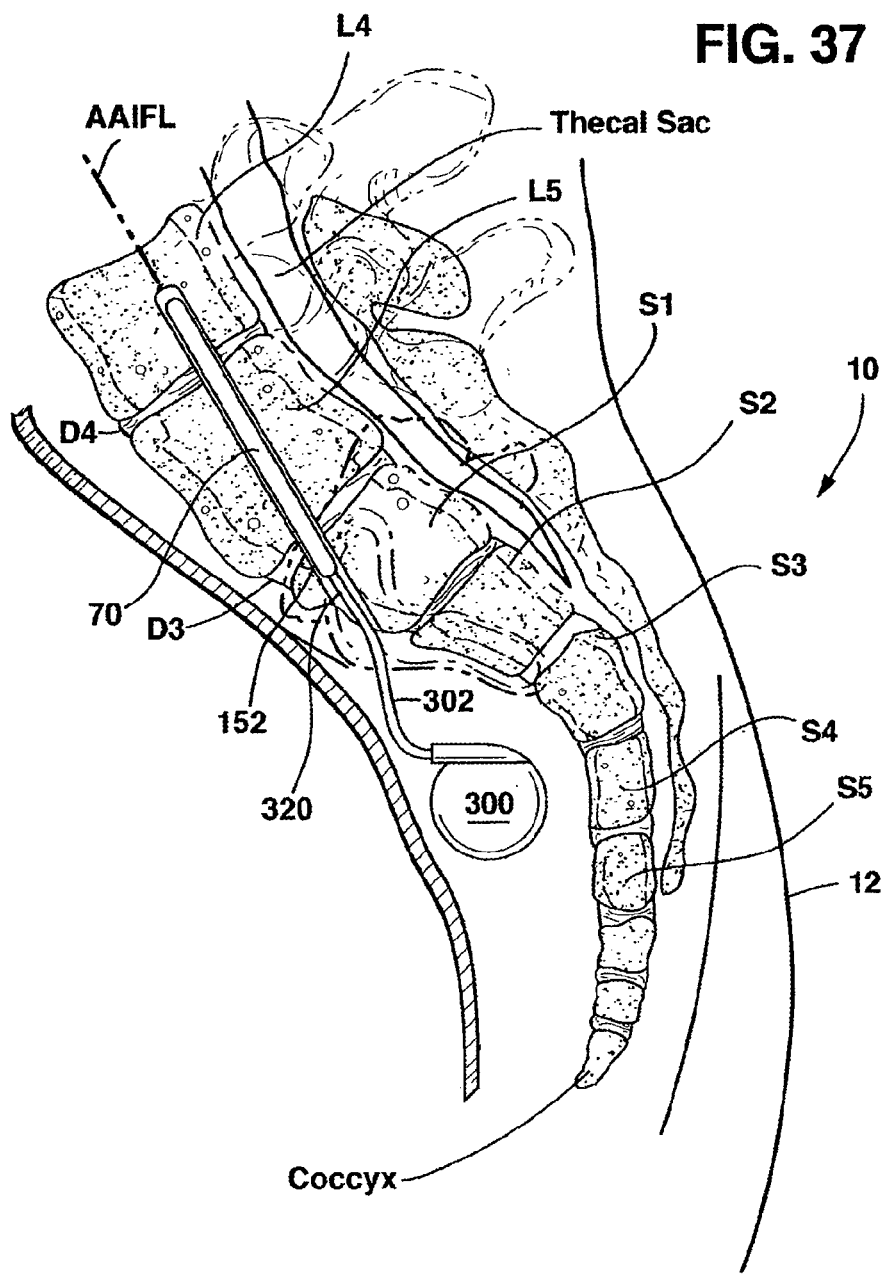

This therapeutic procedure of the present invention can be advantageously conducted without any injury to any ligaments, muscles and facet joints of the spinal motion segment.
Electrical Stimulation:

FIGS. 35-37 illustrate embodiments of a further electrical stimulation therapy that can be delivered in relation to a spinal structure of interest for electrical stimulation, e.g., to a vertebral body or spinal disc or to adjoining nerves. tissues, and the spinal column through one or more TASIF axial bore. The stimulation electrodes can take any known form including unipolar, bipolar or multi-polar electrodes located on an electrical medical lead extended through the TASIF axial bore(s) to position the electrode(s) within one or more vertebral body or spinal disc or extending outward from a vertebral body or spinal disc into operative relation to the spinal cord or a nerve. Or, the electrode(s) can constitute an electrically conductive portion(s) or all of an electrically conductive spinal disc implant or elongated axial spinal implant implanted in various locations as described above. The lead(s) may be connected to a permanently implanted electrical stimulator or may extend through the closed skin incision or a transdermal electrical connector for connection with an external electrical stimulator for temporary electrical stimulation. The permanent implanted electrical stimulator (IES) may be battery powered, e.g., the Itrel 3™ neurostimulation system or powered transdermally receiving power from an external power transmitter, e.g., the Mattrix™ neurostimulation system, both available from Medtronic, Inc., Minneapolis, Minn. Or a bone growth stimulator of the type described in the above-referenced '502 patent or of the type available from EBI Medical Systems, Inc., Parsippany, N.J., can be employed. Certain of these variations are illustrated, for example, in FIGS. 35-37.

In FIG. 35, an IES 300 is coupled through a lead 302 extending through the anterior TASIF axial bore 152 to two active electrodes 304 and 306, for example. The IES 300 provides continuous, negative polarity, electrical stimulation of the type described in the above-referenced '502 patent to the vertebral bodies L4 and L5 to promote bone growth. Or, the IES 300 provides pulsed electrical stimulation to nearby nerves that suppresses pain. The patient may be provided with a limited function programmer for commanding the IES 300 to deliver a drug bolus when symptoms are felt.

The electrodes 304 and 306 are preferably cylindrical and have the same diameter as the diameter of the lead 302. The axial bore diameter may be just large enough to receive the lead 302, so that the lead may be cemented into the TASIF axial bore 152. The conductive housing of the IES 300 provides a return, positive, electrode. The electrodes 304 and 306 may take any shape and be replaced by a single elongated electrode.

In FIG. 36, the IES 300 is coupled through first and second leads 308 and 310 that extend to a first electrode 312 and a second electrode 314 located within diverging TASIF axial bores $152_1$ and $152_2$, respectively, to locate the electrodes 312 and 314 nearer to the spinal column or a vertebral nerve branch. Again, the IES 300 provides pulsed electrical stimulation to nearby nerves that suppresses pain. The stimulation may be applied between the electrodes 312 and 314, or between the commonly connected electrodes 312 and 314 and housing of IES 300.

In FIG. 37, the IES 300 is coupled through lead 320 to the electrically conductive, elongated axial spinal implant 70. The spinal discs D4 and D3 may be fused by way of a complete or partial discectomy and augmented as described above. Again, the IES 300 provides continuous, negative polarity, electrical stimulation of the type described in the above-referenced '502 patent to the vertebral bodies L4 and L5 to promote bone growth. Or, the IES 300 provides pulsed electrical stimulation to nearby nerves that suppresses pain.

It is conceivable to extend a curved TASIF axial bore cephalad to any selected vertebral body and then through the side of a vertebral body to locate one or more of the stimulation electrodes outside the vertebral body and into closer relation with the spinal column or other nerves. A path may be cleared into the thecal sac employing a flexible endoscope and cutting tool. Then, the lead may be advanced along that path to locate the electrode(s) within the thecal sac or the epidural space.

This therapeutic procedure of the present invention can be advantageously conducted without any injury to any ligaments, muscles and facet joints of the spinal motion segment.

Drug Delivery

Figure 38:
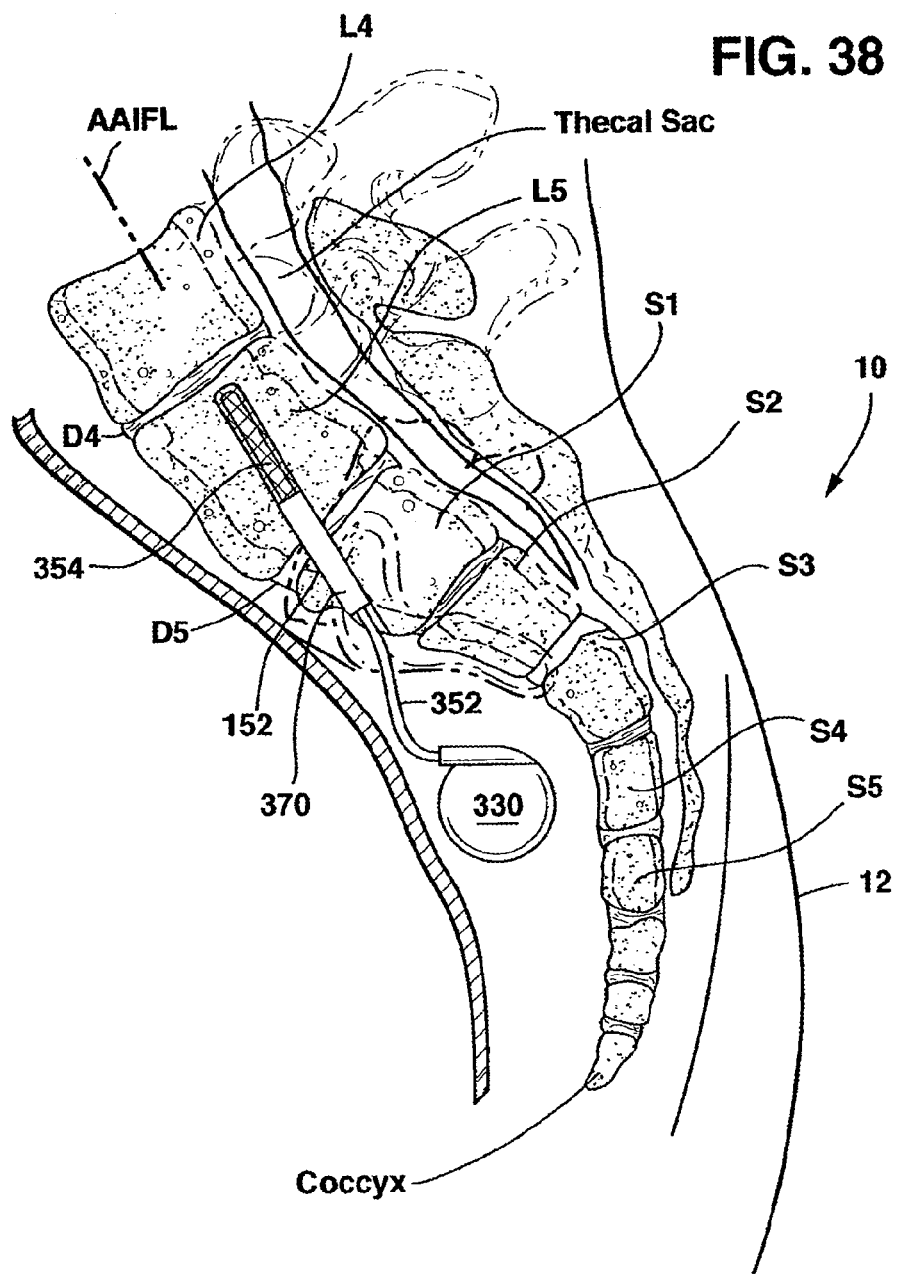
FIGS. 38-40 illustrate, in partial cross-section side views, extending a catheter from an implanted or external drug dispenser through a TASIF axial bore to dispense a drug within or between adjoining vertebral bodies or to nearby nerves and the spinal column to encourage bone growth or to counter pain or to nearby nerves and the spinal column to counter pain.
Figure 39:
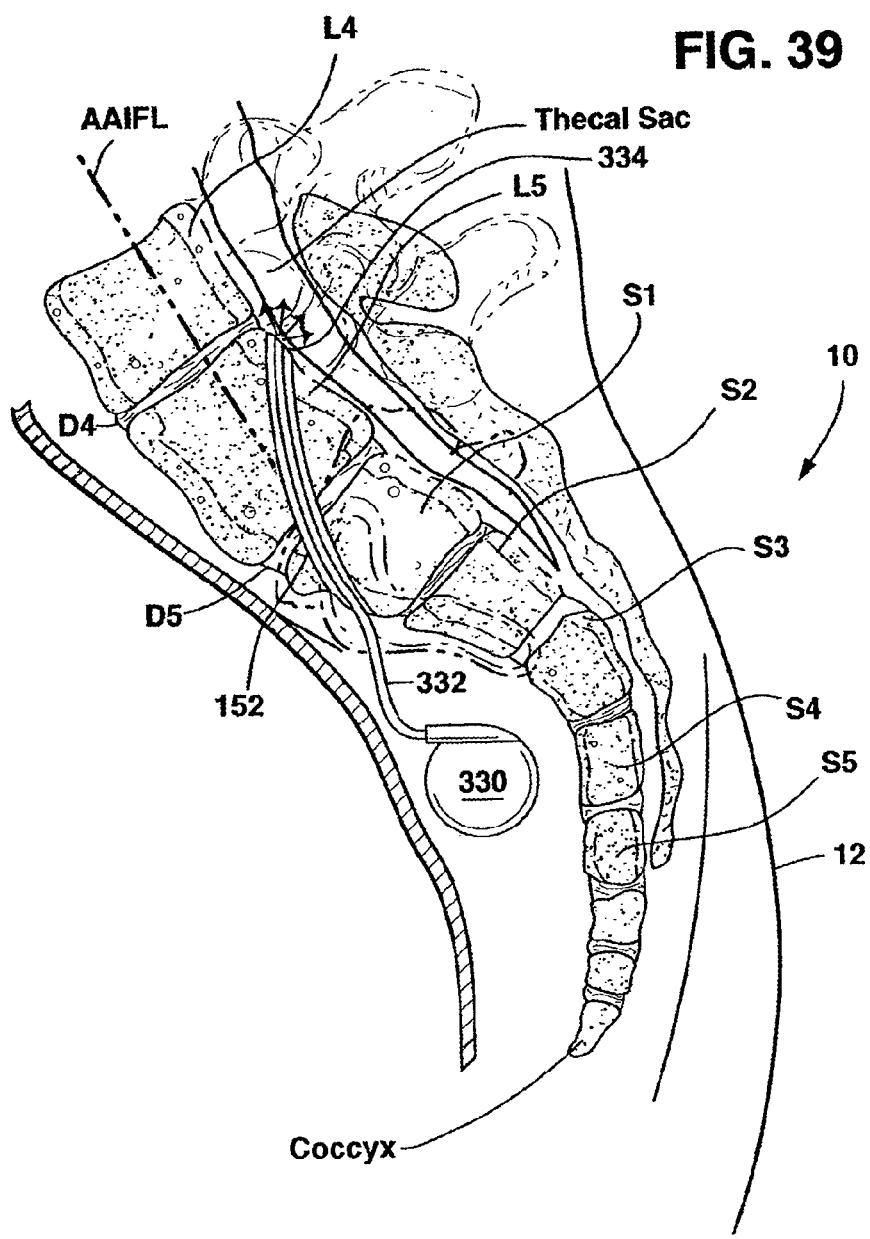
Figure 40:
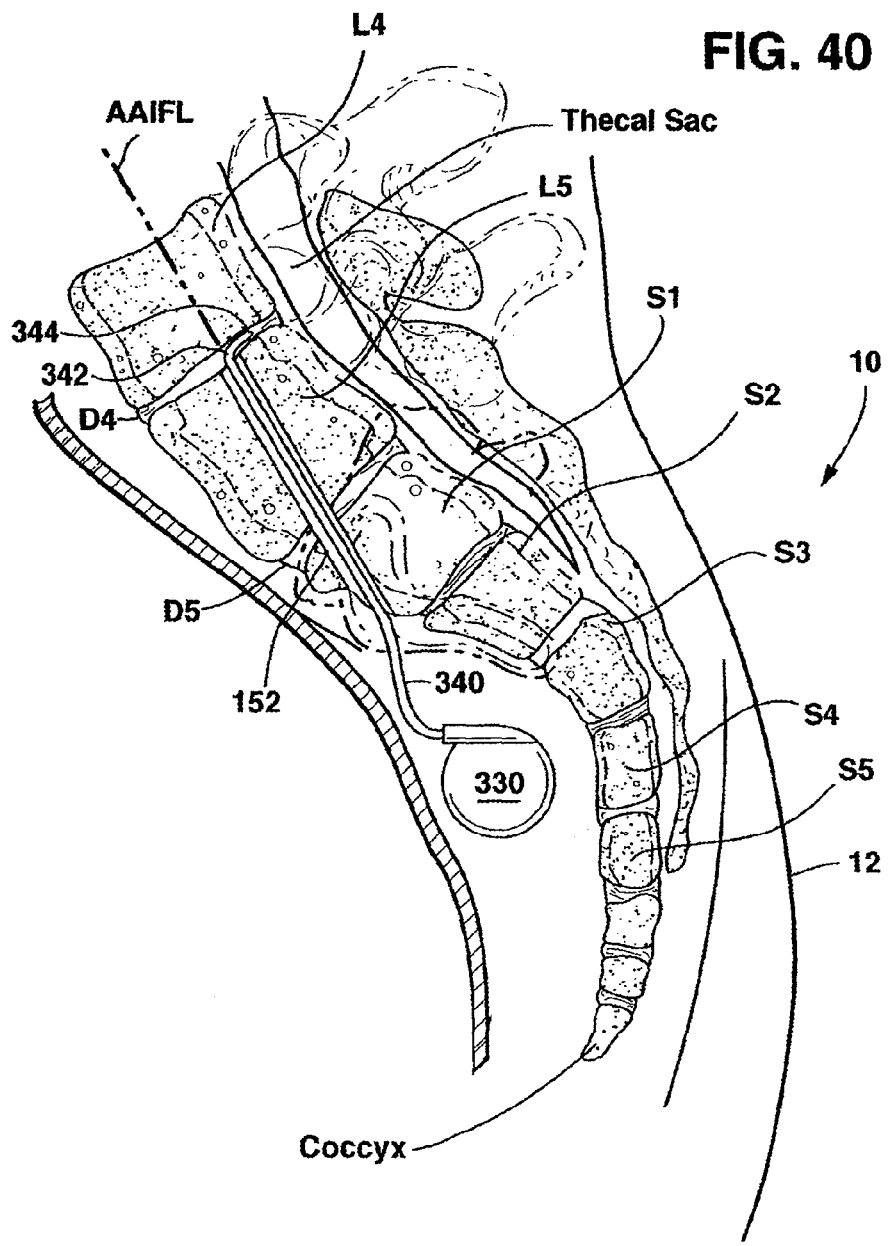

FIGS. 38-40 illustrate embodiments of a further drug delivery therapy that can be delivered through one or more TASIF axial bore to a spinal structure of interest to be treated, e.g., a vertebral body or spinal disc or to adjoining nerves, tissues, and the spinal column. The drug can take any of the known therapy forms, e.g., drugs for analgesic pain killing or for treatment of a disease or disease process or to promote bone growth. The delivery catheters can take any of the known forms, including infusion micro-catheters, infusion guidewires, and drug delivery catheters of the type sold by Medtronic, Inc., Minneapolis, Minn., together with a battery powered implantable drug dispenser, as the SynchroMed™ drug delivery system. The drug delivery catheter has one or more drug delivery port along its length and is extended through a TASIF axial bore(s) to position the delivery port within one or more vertebral body or spinal disc or extending outward from a vertebral body or spinal disc into operative relation to the spinal cord or a nerve. Or, the drug delivery can be through pores of a portion or all of an electrically conductive spinal disc implant or elongated axial spinal implant implanted in various locations as described above. The drug delivery catheter(s) may be connected to a permanently implanted drug dispenser or may extend through the closed skin incision or a transdermal electrical connector for connection with an external drug dispenser for temporary drug delivery. The permanent implanted drug dispenser (IDP) may be battery powered or may be powered transdermally receiving power from an external power transmitter. Certain of these variations are illustrated, for example, in FIGS. 38-40.

In FIG. 38, an IDP 330 is coupled to a drug delivery catheter 352 extending through the anterior TASIF axial bore 152 to a drug delivery port section of the catheter or a porous axial spinal implant 354 located within the vertebral body L5. The housing of the IDP 330 may contain a fill port oriented toward the patient's skin so that the internal drug reservoir can be percutaneously refilled in a manner well known in the art. The IDP 330 provides continuous or periodic delivery of doses of the drug. The patient may be provided with a limited function programmer for commanding the IDP 330 to deliver a drug bolus when symptoms are felt.

The drug delivery section or porous axial spinal implant 354 is preferable cylindrical, and the axial bore diameter may be just large enough to receive the drug delivery catheter or porous axial spinal implant 354, so that it may be cemented into the TASIF axial bore 152 at least at the caudal end thereof by a cement plug 370 bridging the disc D5 and vertebral body S1 in this case. More than one such TASIF axial bore 152 may be formed and more than one drug delivery catheter 352 may be provided to distribute the delivered drug more widely in a single vertebral body or in multiple vertebral bodies.

In FIG. 39, the TASIF axial bore 152 diverges from the anterior sacral starting point in a posterior direction to a cephalad opening in vertebral body L5, and a drug delivery catheter 332 extends from the IDP 330 through the TASIF axial bore 154 to locate at least one drug delivery port 334 adjacent to the thecal sac. A distal portion of the drug delivery catheter 332 can be extended from the cephalad opening to locate the distal port or an array of such ports 334 alongside a nerve or portion of the spinal cord of interest. The TASIF axial bore 152 may be extended through any number of vertebral bodies and through the cortical bone of the side wall of any of the vertebral bodies to locate the drug delivery port(s) 334 in proximity to the nerve or portion of the spinal cord of interest. More than one such TASIF axial bore 152 can be formed and more than one drug delivery catheter 332 inserted therethrough and coupled with the IDP 330 to deliver drug therapy over a wider area. A path may be cut into the thecal sac or more cephalad into the epidural space of the spinal column employing a flexible endoscope and cutting tool. Then, the drug delivery catheter distal portion may be advanced along that path to locate the drug delivery port(s) within the thecal sac or the epidural space.

In FIG. 40, the TASIF axial bore 152 terminates within the spinal disc D4 or a disc space created there by a discectomy, and a drug delivery catheter 340 extends from the IDP 330 through the TASIF axial bore 154 to locate a distal portion 342 and at least one drug delivery port 344 within the spinal disc or disc space. The drug can be delivered into the spinal disc or disc space. Or, the distal portion of the drug delivery catheter 332 can be extended through the annulus, if present, and toward any nerve or interest or the spinal column to deliver drug alongside a nerve or portion of the spinal cord of interest. The TASIF axial bore 152 may be extended through any number of vertebral bodies and spinal discs to locate the drug delivery port(s) 344 in proximity to a spinal disc or disc space or a nerve or portion of the spinal cord of interest. More than one such TASIF axial bore 152 can be formed and more than one drug delivery catheter 340 inserted therethrough and coupled with the IDP 330 to deliver drug therapy to a number of spinal discs, disc spaces or nerves or portions of the spinal cord of interest It is conceivable to extend a curved TASIF axial bore cephalad to any selected intervertebral spinal disc and then through the annulus to locate the drug delivery port(s) outside the spinal disc and into closer relation with the spinal column or other nerves. A path may be cleared into the thecal sac or more cephalad into the epidural space of the spinal column employing a flexible endoscope and cutting tool. Then, the drug delivery catheter distal portion may be advanced along that path to locate the drug delivery port(s) within the thecal sac or the epidural space.

This therapeutic procedure of the present invention can be advantageously conducted without any injury to any ligaments, muscles and facet joints of the spinal motion segment.

Figure 41:
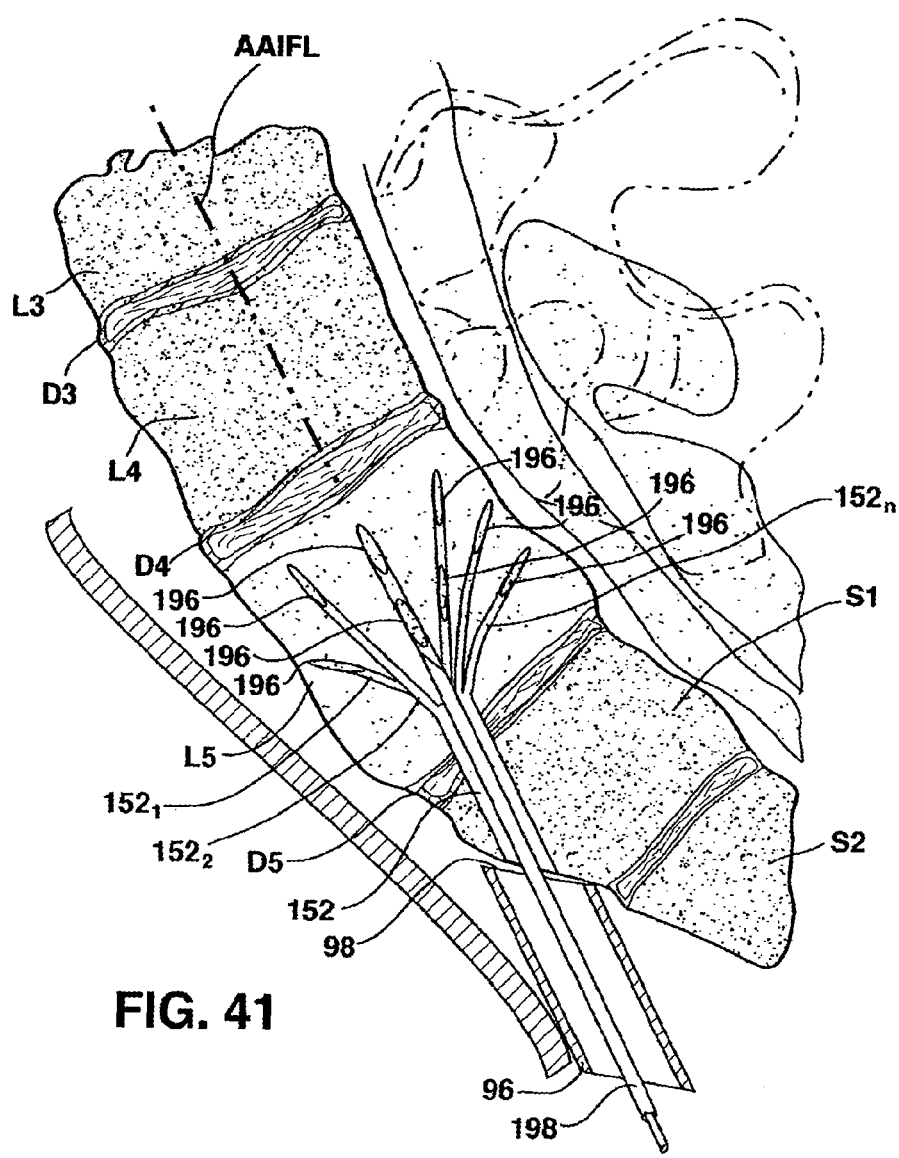
FIG. 41 illustrates, in a partial cross-section side view, the insertion of a plurality of radioactive therapeutic seeds about the interior of a lumbar vertebral body for brachytherapy of a sarcoma.

Brachytherapy of a Vertebral Body:

FIG. 41 illustrates, in a partial cross-section side view, the insertion of a plurality of radioactive therapeutic seeds about the interior of a lumbar vertebral body for brachytherapy to treat metastatic disease in the spine or adenopathy in the retroperitoneum. Radioactive seed therapy is a well known and well accepted medical procedure for the treatment of various oncological and other medical conditions. Seed therapy, also known as brachytherapy, typically involves the implantation of fifty to one hundred tiny capsules (seeds) into or around a treatment site. The capsules contain a radioactive isotope which irradiates the treatment site at close range without adversely affecting other parts of the body. Brachytherapy has been used successfully in the treatment of various types of cancers such as prostate cancer. It has also been used to prevent the growth or re-growth of tissues in the treatment of various occlusive diseases such as arteriosclerosis and arthrosclerosis subsequent to balloon angioplasty.

Radioactive therapeutic seeds are carefully designed to possess several important qualities. First, they must be relatively small, approximately 0.025 inch in diameter and approximately 0.16 inch long so that they may be implanted using minimally invasive instruments and techniques. Second, the radioactive isotope must be enclosed in a bio-compatible protective package since the seeds are typically not removed and will remain in the body for many years. Third, each seed preferably includes a radiopaque (e.g. high Z material) marker so that it can be located at the treatment site with the aid of fluoroscopy. Fourth, the protective package and the radiopaque marker preferably do not cast "shadows" in the irradiation pattern of the isotope. Fifth, the isotope should be evenly distributed within the protective package so as to avoid any "hot spots" of radiation. The state of the art of such radioactive therapeutic seeds is disclosed in U.S. Pat. No. 6,080,099 and patents referenced therein.

In FIG. 41, a plurality n of small diameter, anterior TASIF axial bores $152_1$, $152_2$, ... $152_n$ that diverge apart from a common axial bore 152 are bored from the anterior sacral position accessed via the anterior tract sheath 96 into vertebral body L5 and a further plurality N of radioactive seeds 196 are deposited in the bores. Each radioactive seed 196 is deposited into an axial bore through a small bore catheter or needle 198, optionally using a wire stylet to push the seed from the needle lumen. More than one radioactive seed separated apart by a separator can be inserted into each axial bore.

In this way, the radioactive seeds can be distributed within a vertebral bore in an optimal pattern that cannot be accomplished as atraumatically by a lateral laparascopic approach and penetration of the vertebral body.

Figure 42:
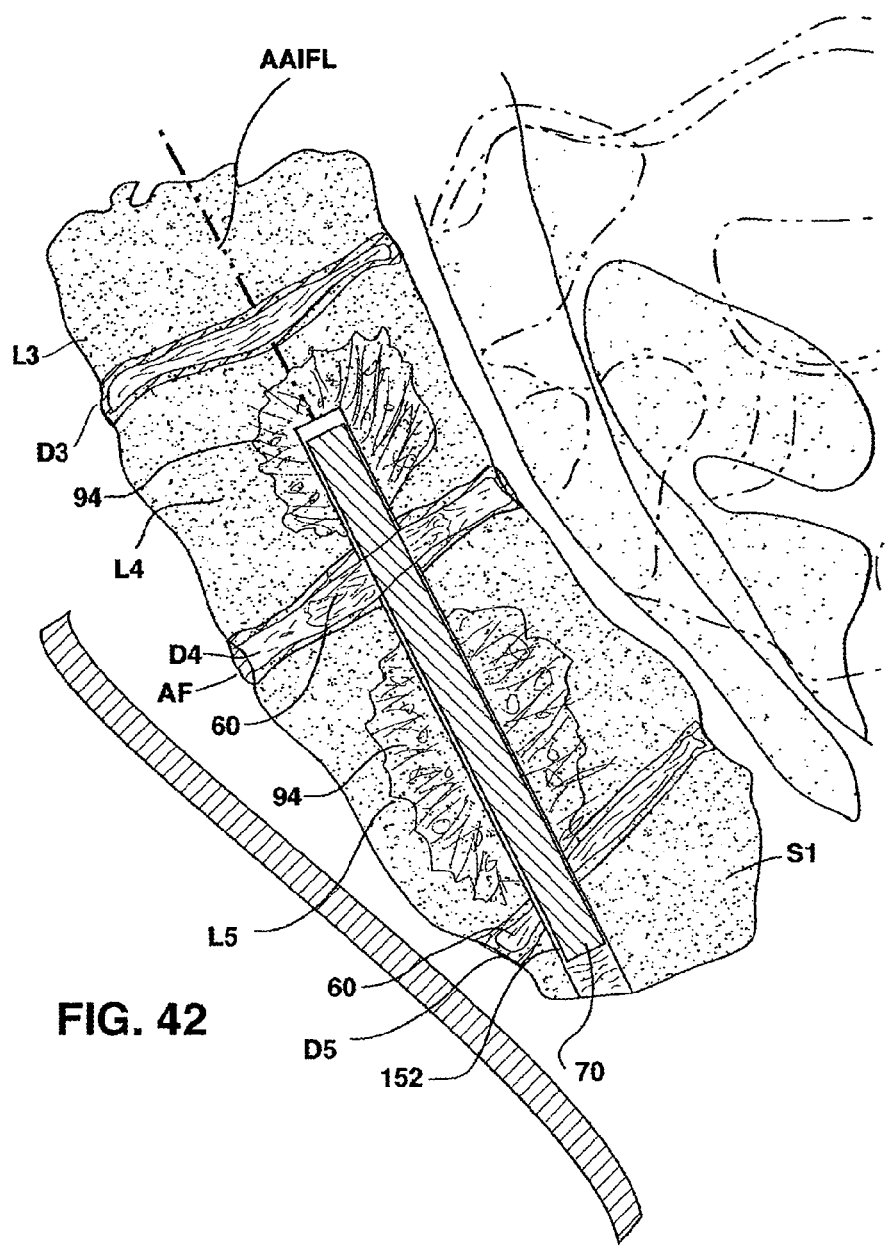
FIG. 42 illustrates, in a partial cross-section side view, a combination of above described therapies comprising the injection of bone growth materials or bone cement through an axial bore into cancellous bone of two vertebral bodies and intervertebral disc cavities and the insertion of an elongated axial spinal implant into the axial bore to effect a fusion with reinforcement of the vertebral bodies.

Combined Therapies:

The above-described therapies can be combined to treat a given patient. FIG. 42 illustrates, in a partial cross-section side view, a combination of certain of the above described therapies particularly for effecting spinal fusion, and alignment, and reinforcement. In this illustrated combined therapy, the anterior TASIF axial bore 152 is formed as described above via the tract sheath 96 extending through vertebral bodies S1, L5 and into L4. Partial discectomies are performed of the intervertebral discs D5 and D4 to form respective disc cavities. A bolus of bone growth material or bone cement 60 is injected into the disc cavities of intervertebral discs D4 and D5 through the axial bore. Vertebroplasty procedures of the type shown in FIG. 26 are then performed to inject a bone growth material or bone cement mass 94 into the gaps and fissures of cancellous bone of the two vertebral bodies L4 and L5, which may or may not be fractured or collapsed. An elongated axial spinal implant 70 is inserted into the axial bore 152 and through the injected bone growth material or bone cement 94 and 60 to effect a fusion with reinforcement of the vertebral bodies L4 and L5.

In this case, the elongated axial spinal implant 70 is preferably a 4.0 mm by 60.0 mm carbon fiber rod having a spiral screw thread or other affixation mechanism extending along its length. This therapy may advantageously be performed using three such elongated axial spinal implants implanted in this way into three diverging axial bores to maximize the strength of the fusion.

Summary

All patents and other publications identified above are incorporated herein by reference.

In all of the above-described procedures, the visualization of the spine and the introduction of instruments employed to form the anterior or posterior axial bore(s) or to perform therapies, and any spinal disc implants or axial spinal implants or other implanted medical devices is effected employing conventional imaging techniques including open MRI, fluoroscopy or ultrasound through the patient's body or using endoscopic techniques through an axial bore.

While the present invention has been illustrated and described with particularity in terms of preferred embodiments, it should be understood that no limitation of the scope of the invention is intended thereby. The scope of the invention is defined only by the claims appended hereto. It should also be understood that variations of the particular embodiments described herein incorporating the principles of the present invention will occur to those of ordinary skill in the art and yet be within the scope of the appended claims.

What is claimed is:

1. A method for correcting a deformity in the spine by realigning vertebral bodies, the method comprising:
    aligning vertebral bodies to correct a spinal deformity;
    accessing an anterior sacral position of a sacral vertebral body; from the accessed sacral position, boring a trans-sacral bore through or into one or more cephalad vertebra;
    and advancing a spinal implant into the trans-sacral bore, the spinal implant comprising:
    a preformed elongated body having a curvature along a longitudinal axis of the body configured to correct the deformity in the spine;
    a caudal body comprising an external thread along the longitudinal axis of the body configured to engage bone inside a caudal vertebra;
    a cephalad body configured for placement inside a cephalad vertebra; and
    a flexible center portion extending between said caudal body and said cephalad body configured to span a vertebral disk space.

2. The method of claim 1, wherein the elongated body is surface roughened for promoting bony ingrowth.

3. The method of claim 1, wherein the elongated body forms a porous tube for promoting bony ingrowth.

4. The method of claim 1, further comprising actuating a spring in the elongated body configured for bending along the longitudinal axis of the elongated body.

5. The method of claim 1, further comprising absorbing shock with the elongated body with a spring configured for a shock absorbing function.

6. The method of claim 1, further comprising absorbing shock with the elongated body with a hydraulic fluid configured for a shock absorbing function.

7. The method of 1, further comprising maintaining an instantaneous center of rotation of adjacent vertebral bodies with the elongated body.

8. The method of claim 1, further comprising changing a distance between the caudal body and the cephalad body through rotation by a distraction tool of a threaded rod in the center portion.

9. A method for correcting a deformity in the spine by realigning vertebral bodies, the method comprising:

aligning vertebral bodies to correct a spinal deformity; accessing an anterior sacral position of a sacral vertebral body;

from the accessed sacral position, boring a trans-sacral bore through or into one or more cephalad vertebra; and advancing a spinal implant into the trans-sacral bore, the spinal implant comprising:

an elongated body having a curvature along a longitudinal axis of the body configured to absorb shock of stresses placed on the spine to relieve pain and restore spine loading function, the elongated body comprising:

a caudal body comprising an external thread along the longitudinal axis of the body configured to engage bone inside a caudal vertebra;

a cephalad body configured for placement inside a cephalad vertebra; and a center portion extending between said caudal body and said cephalad body configured to span a vertebral disk space, the center portion configured to bend.

10. The method of claim 9, further comprising actuating a spring in the elongated body configured for bending along the longitudinal axis of the elongated body.

11. The method of 9, further comprising maintaining an instantaneous center of rotation of adjacent vertebral bodies with the elongated body.

12. The method of claim 9, further comprising changing a distance between the caudal body and the cephalad body through rotation by a distraction tool of a threaded rod in the center portion.

* * * * *

UNITED STATES PATENT AND TRADEMARK OFFICE
CERTIFICATE OF CORRECTION

| | |
|---|---|
| PATENT NO. | : 8,317,867 B2 |
| APPLICATION NO. | : 13/342868 |
| DATED | : November 27, 2012 |
| INVENTOR(S) | : Cragg |

It is certified that error appears in the above-identified patent and that said Letters Patent is hereby corrected as shown below:

Title Page

In column 2 (page 4 item 56) at line 2, Under Other Publications, change "Urogrpahy-" to --Urography--.

In column 2 (page 4 item 56) at line 4, Under Other Publications, change "Phneumography" to --Pneumography--.

In column 2 (page 4 item 56) at line 7, Under Other Publications, change "Pelvix,"" to --Pelvis,"--.

In the Specifications

In column 2 at line 24, Change "micropolysacharides" to --micropolysaccharides--.

In column 4 at line 67, Change "laparascopic" to --laparoscopic--.

In column 5 at line 26, Change "artiroscopic" to --arthroscopic--.

In column 5 at line 65, Change "posteriolateral" to --posterolateral--.

In column 10 at line 29 (approx.), Change "posteriolateral" to --posterolateral--.

In column 14 at line 38, Change "body:" to --body;--.

In column 14 at line 41, Change "body:" to --body;--.

In column 17 at line 6, Change "(Radiology;" to --(Radiology 1999;--.

In column 17 at line 27, Change "vetebral" to --vertebral--.

In column 19 at line 1, Change "Diver in" to --Diverging--.

In column 24 at line 56-57, Change "polyolefine," to --polyolefin,--.

In column 24 at line 57, Change "terepthalate," to --terephthalate,--.

In column 25 at line 3, Change "torqueing" to --torquing--.

In column 25 at line 57, Change "o" to --to--.

Signed and Sealed this
Fourteenth Day of May, 2013

Teresa Stanek Rea
*Acting Director of the United States Patent and Trademark Office*

CERTIFICATE OF CORRECTION (continued)
U.S. Pat. No. 8,317,867 B2

In column 27 at line 2, Change "80" to --80.--.

In column 27 at line 20, Change "include" to --include.--.

In column 34 at line 19, Change "nerves." to --nerves,--.

In column 34 at line 38, Change "Mattrix™" to --Matrix™--.

In column 36 at line 51, Change "interest" to --interest.--.

In column 37 at line 45, Change "laparascopic" to --laparoscopic--.

In the Claims

In column 38 at line 65, In Claim 7, change "1," to --claim 1,--.

In column 40 at line 12 (approx.), In Claim 11, change "9," to --claim 9,--.